United States Patent
Morales et al.

(10) Patent No.: US 9,550,790 B2
(45) Date of Patent: *Jan. 24, 2017

(54) THIENOPYRANONES AS KINASE INHIBITORS

(71) Applicant: SignalRx Pharmaceuticals, Inc., San Diego, CA (US)

(72) Inventors: Guillermo A. Morales, Oro Valley, AZ (US); Kevin Weber, Carmel, IN (US); Jessica Newblom, Indianapolis, IN (US); Joseph R. Garlich, Hawaii National Park, HI (US)

(73) Assignee: SignalRx Pharmaceuticals, Inc., San Diego, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 14/041,279

(22) Filed: Sep. 30, 2013

(65) Prior Publication Data

US 2014/0073584 A1    Mar. 13, 2014

Related U.S. Application Data

(63) Continuation of application No. 12/735,309, filed as application No. PCT/US2009/031864 on Jan. 23, 2009, now Pat. No. 8,857,807.

(60) Provisional application No. 61/023,320, filed on Jan. 24, 2008, provisional application No. 61/110,745, filed on Nov. 3, 2006.

(51) Int. Cl.
| | | |
|---|---|---|
| C07D 495/04 | (2006.01) |
| A61K 31/381 | (2006.01) |
| A61K 31/5377 | (2006.01) |
| A61K 31/69 | (2006.01) |
| A61K 45/06 | (2006.01) |
| A61K 47/48 | (2006.01) |
| C07K 5/11 | (2006.01) |
| A61K 31/538 | (2006.01) |
| C07F 5/02 | (2006.01) |

(52) U.S. Cl.
CPC ........... *C07D 495/04* (2013.01); *A61K 31/381* (2013.01); *A61K 31/538* (2013.01); *A61K 31/5377* (2013.01); *A61K 31/69* (2013.01); *A61K 45/06* (2013.01); *A61K 47/48238* (2013.01); *A61K 47/48246* (2013.01); *C07F 5/025* (2013.01); *C07K 5/1019* (2013.01)

(58) Field of Classification Search
None
See application file for complete search history.

(56) References Cited

U.S. PATENT DOCUMENTS

| | | |
|---|---|---|
| 5,095,032 A | 3/1992 | Bertram et al. |
| 6,486,163 B1 | 11/2002 | Leonardi et al. |
| 6,894,055 B2 | 5/2005 | Melese et al. |
| 6,949,537 B2 | 9/2005 | Garlich et al. |
| 7,396,828 B2 | 7/2008 | Garlich et al. |
| 7,662,977 B2 | 2/2010 | Garlich et al. |
| 2010/0310466 A1 | 12/2010 | Morales et al. |

OTHER PUBLICATIONS

J. Hollick et al. "Pyranone, Thiopyranone and Pyridone Inhibitors . . . Kinase", J. Med. Chem. 2007, 50, 1958-1972.
Volovenko et al. "Structure of Condensed 2-amino-3-aryl(het)areno[b]pyran-4-ones." Ukr. Khim. Zhurn., 1989, 55, 1061-1064. (English translation from Russian).

*Primary Examiner* — Samantha Shterengarts
(74) *Attorney, Agent, or Firm* — TDW Patents & Consulting; Thomas D. Webster

(57) ABSTRACT

The invention relates to compounds of formula I (or pharmaceutically acceptable salts thereof) as defined herein, pharmaceutical compositions thereof, and their use in manufactures and methods for modulating biological processes including inhibition of kinase activity such as PI-3 kinase.

1 Claim, No Drawings

THIENOPYRANONES AS KINASE INHIBITORS

CROSS REFERENCE TO RELATED APPLICATIONS

The present application is a continuation of U.S. application Ser. No. 12/735,309 filed Jul. 1, 2010, which is a national stage entry of PCT/US09/31864, filed Jan. 23, 2009, which claims priority to U.S. Provisional Application Nos. 61/023,320 and 61/110,745, filed Jan. 24, 2008 and Nov. 3, 2008, respectively. The entire contents of each of the foregoing applications is herein incorporated by reference.

FIELD OF THE INVENTION

The present invention relates to new thienopyranone compounds and conjugates thereof that demonstrate activity as inhibitors of kinases including PI-3 kinase, useful as anti-tumor agents in mammals.

BACKGROUND

This invention relates to thienopyranone compounds that demonstrate activity as kinase inhibitors including PI-3 kinase. In particular, the invention relates to new thienopyranone compounds, conjugates thereof, pharmaceutical compositions containing the thienopyranones or conjugates thereof as active ingredients, and use of the thienopyranone compounds as therapeutic agents including antitumor agents for the treatment of neoplasmic disorders including cancer.

Protein kinases play an important role in regulating most cellular functions including proliferation, cell cycle, cell metabolism, survival/apoptosis, DNA damage repair, cell motility, and response to the microenvironment. Not surprisingly kinases have been identified as oncogenes. For example, kinases such as c-Src, c-Abl, mitogen activated protein (MAP) kinase, phosphotidylinositol-3-kinase (PI3-K), AKT (also known as PKB), and the epidermal growth factor (EGF) receptor are commonly activated in cancer cells and are known to contribute to tumorigenesis. Many of these mutations occur in the same signaling pathway; for example, HER-kinase family members (HER1 [EGFR], HER3, and HER4) transmit signals through MAP kinase and PI-3 kinase to promote cell proliferation.

PI-3 kinases are a large family of lipid kinases comprising roughly 16 members divided into 3 classes based on sequence homology and the particular product formed by enzyme catalysis. The class I PI-3 kinases are composed of 2 subunits: a 110 kd catalytic subunit and an 85 kd regulatory subunit. Class I PI-3 kinases are involved in important signal transduction events downstream of cytokines, integrins, growth factors and immunoreceptors, and control of this pathway may lead to important therapeutic effects. Indeed, inhibition of class I PI-3 kinase induces apoptosis, blocks tumor induced angiogenesis in vivo, and increases radiosensitivity in certain tumors.

Molecular and genetic studies have demonstrated a strong correlation between the PI-3 kinase pathway (also known as PI3K-AKT pathway) and a variety of diseases in humans such as inflammation, autoimmune conditions, and cancers (P. Workman et al. *Nat. Biotechnol.* 2006, 24, 794-796). The PI-3 kinase pathway controls a number of cellular functions including cell growth, metabolism, differentiation, and apoptosis. Many types of cancer are thought to arise in response to abnormalities in signal transduction pathways of which the PI-3 kinase pathway is a major example. The PI-3 kinase pathway comprises a number of enzymes including PI-3 kinase, PTEN (Phosphatase and Tensin homolog deleted on chromosome Ten), and AKT (a serine/threonine kinase) all of which are involved in producing and maintaining intracellular levels of second messenger molecule PtdIns(3,4,5)P3 ($PIP_3$). Homeostasis in the levels of this important second messenger is maintained by the interaction between PI-3 kinase and PTEN. When either PI-3 kinase or PTEN are mutated and/or reduced in activity $PIP_3$ levels are perturbed and it is believed that this perturbation may act as a trigger in the development of cancer. Indeed, both PI-3 kinase and PTEN have been found to be mutated in multiple cancers including glioblastoma, ovarian, breast, endometrial, hepatic, melanoma, gut, lung, renal cell, thyroid and lymphoid cancer. Multiple studies have now shown that p110α, which is a Class IA isoform of the regulatory subunit of PI-3 kinase, is frequently over-expressed and mutated in many cancers including gliomas, colon, brain, breast, lung, prostate, gynecological and other tumor types (Y. Samuels et al. *Science* 2004, 304, 554). Thus, a rational approach to treating cancer relates to developing drugs that act on kinases including those of the PI-3 kinase pathway.

Another putative mechanism for cancer involving kinase dependency is through loss of a negative regulator. Perhaps the best conceptual example of this comes from tumors with mutations in the PTEN tumor suppressor gene. This gene, which is mutated or deleted in a number of different cancers, encodes a lipid phosphatase that regulates signaling through the phosphatidylinositol 3-kinase (PI-3 kinase) pathway. Specifically, PTEN dephosphorylates PIP3, the product of PI-3 kinase (for review see L. C. Cantley et al. *Proc. Natl. Acad. Sci.* 1999, 96, 4240-4245). As a consequence of PTEN loss and the resultant increase in PIP3 levels, signal propagation through downstream kinases such as AKT is constitutively elevated. Preclinical studies suggest that this indirect mode of constitutive kinase activation in tumor cells, through loss of the PTEN suppressor gene, creates a kinase dependency analogous to that seen in tumors with direct, activating mutations in the kinase itself.

Genetic and biochemical evidence from several model systems has established that constitutive levels of AKT can regulate TOR (mTOR in mammalian systems) through phosphorylation of the tuberous sclerosis complex (K. Inoki et al. *Nat. Cell Biol.* 2002, 4, 648-657). Hence, tumors with loss-of-function mutations in PTEN exhibit constitutive activation of AKT, as well as other downstream kinases such as mTOR. Many such tumors in murine models have been shown to be sensitive to mTOR inhibitors (M. S. Neshat et al. *Proc. Natl. Acad. Sci.* 2001, 98, 10314-10319).

At the cytocellular level, the induction and/or progression of cancer appears to involve a sub-population of cells within a tumor known as cancer stem cells. Within a population of cancer cells there exist a small number of cells that are capable of fully re-establishing a tumor. These cells are called cancer stem cells and are thought to be responsible for the inability to cure cancer with current drugs. These cells are characterized as having enhanced drug efflux properties, lacking in cell cycle progression (quiescent), and possessing resistance to anoikis (apoptosis upon experiencing loss of anchorage). Cancer stem cells have been described in the literature in solid tumor types for example see the review and references incorporated therein by J. E. Visvader et al. *Nat. Rev. Cancer* 2008, 8, 755-768: "Cancer Stem Cells in Solid Tumors: accumulating evidence and unresolved questions". Non-solid tumor cancer stem cells have also been reviewed recently, for example, see the review and references incorporated therein by J. E. Dick et al. *Blood* 2008, 4793-4807: "Stem cell concepts renew cancer research". To date the only documented clinical example of an approved cancer therapeutic drug decreasing cancer stem cells has been the use of Lapatinib shown to decrease the number of breast cancer stem cells in biopsies of women with breast tumors possessing high levels of HER2 protein (decreased from 11% down to 5% of cells) [C. Schmidt et al. *J. Natl. Cancer I.* 2008, 100, 694-695: "Lapatinib Study Supports Cancer Stem Cell Hypothesis, Encourages Industry Research"].

While therapeutic agents that act as modulators of signaling pathways are of clear therapeutic interest as agonists or antagonist of particular enzymes within a signaling pathway, e.g. inhibitors of PI-3 kinase, recent evidence indicates that independent mechanisms exist for providing therapeutic efficacy including, for example, oxidative stress. The generation of oxidative stress in cancer cells is a recent but well described cancer treatment approach. Examples of agents that induce such stress include clinically evaluated compounds such as buthionine sulfoximine/melphalan, imexon, arsenic trioxide, and motexafin gadolinium and the like [see for example the review and references incorporated therein by R. H. Engel et al. *Front. Biosci* 2006, 11, 300-312: "Oxidative Stress and Apoptosis: a new treatment paradigm in cancer"]. Cromenones such as LY294002 and the related analog LY3035111 have been reported to induce apoptosis in tumor cells due to intracellular hydrogen peroxide production independent of their PI3 kinase inhibition activity [T. W. Poh et al. *Cancer Res.* 2005, 6264-6274: "LY294002 and LY303511 Sensitize Tumor Cells to Drug-Induced Apoptosis via Intracellular Hydrogen Peroxide Production Independent of the Phosphoinositide 3-Kinase-Akt Pathway"]. This ability to induce oxidative stress in cancer cells is a positive attribute for an anticancer agent. Oxidative stress induction has also been demonstrated to enhance sensitivity of prostate cancer cells to nonapopototic concentrations of the chemotherapeutic agent vincristine.

LY294002 (2-(4-morpholinyl)-8-phenyl-4H-1-benzopyran-4-one) is a potent, non-selective inhibitor of PI-3 kinases with an IC50 of 1.4 µM (C. J. Vlahos et al. *J. Biol. Chem.* 1994, 269, 5241-5248). While LY294002 is an effective inhibitor of PI-3 kinase it has several undesirable attributes for clinical use including lack of aqueous solubility, poor pharmacokinetics, unacceptable toxicity, no tissue specificity, rapid metabolism in animals, and a synthetic route that involves the use of carbon disulfide, a highly toxic compound. As such, LY294002 has never been developed for clinical use.

Thus, there continues to be a need for safe and effective kinase inhibitors, including PI-3 kinase inhibitors, that are suitable for clinical use as tumor growth inhibitors and cancer stem cell inhibitors. The present invention relates to thienopyranone compounds that surprisingly provide significantly improved properties and advantages over LY294002 including unexpectedly superior potency as PI-3 kinase, cancer cell and cancer stem cell inhibitors, oxidative stress inducers, and synthetic procedures that avoid the need to use highly toxic compounds such as carbon disulfide.

SUMMARY OF THE INVENTION

The present invention relates in one aspect to thienopyranone (7H-thieno[3,2-b]pyran-7-ones) compounds of the Formula I or a pharmaceutically acceptable salt thereof:

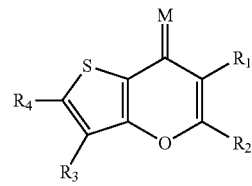

Formula I wherein M is oxygen (O) or sulfur (S);
R1 is selected from H, halogen, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is selected from R1 or

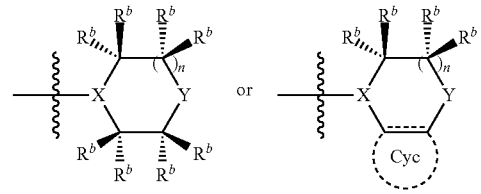

where X is C, N, P, P(O), SiR$^b$;
n is 0, 1, or 2;
Y is C—R1, O, S, NR$^a$, —C(O)(NH$_2$), —P(Z)$_m$R$^a$, SiR$^a$R$^b$, BR$^b$;
Z is O or S;
m=0 or 1;
R$^a$ is hydrogen (H) or independently at each instance any group defined in R1;
R$^b$ is hydrogen (H) or independently at each instance any group defined in R1;
R3 is selected from R1;
R4 is selected from R1; and
Cyc is an aryl, substituted aryl, heterocycle, substituted heterocycle, carbocycle, and substituted carbocycle.

As used herein, the expression "a compound of Formula X" (e.g. Formula I, II, III, etc.), or the expression "a compound of the invention" includes the compound, conjugates thereof, and any conventional prodrug thereof, as well as a pharmaceutically acceptable salt of said compound, conjugate, or prodrug. The compounds of the present invention also encompass polymorphic forms, solvates, hydrates, salts and complexes thereof.

Compounds of Formula I are useful as inhibitors of kinases including, for example and not limited to, mTOR kinase, PIM-1 kinase, PLK-1 kinase, DNA-PK kinase, and Class IA and IB PI-3 kinases. In addition, various compounds of Formula I are useful inhibitors of tumor growth and for the treatment of cancer.

Accordingly, it is an object of the present invention to provide compounds, compositions, and methods for inhibiting kinases, for example PI-3 kinases, and for inhibiting cancerous tumor growth and causing tumor reduction.

These and other objects of the invention are evidenced by the summary of the invention, the description of the preferred embodiments and the claims.

DETAILED DESCRIPTION

A. Definitions

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer.

The term "cancerous cell" as provided herein, includes a cell affected by any one of the above-identified cancers. The term "cancer stem cell" refers to a subpopulation of cells in a solid or non-solid tumor that demonstrate enhanced drug efflux properties, are lacking in cell cycle progression, and are resistant to anoikis.

As used herein, the term "branched" refers to a group containing from 1 to 24 backbone atoms wherein the backbone chain of the group contains one or more subordinate branches from the main chain. Preferred branched groups herein contain from 1 to 12 backbone atoms. Examples of branched groups include, but are not limited to, isobutyl, t-butyl, isopropyl, —CH$_2$CH$_2$CH(CH$_3$)CH$_2$CH$_3$, —CH$_2$CH (CH$_2$ CH$_3$)CH$_2$ CH$_3$, —CH$_2$CH$_2$C(CH$_3$)$_2$CH$_3$, —CH$_2$CH$_2$C(CH$_3$)$_3$ and the like.

The term "unbranched" as used herein refers to a group containing from 1 to 24 backbone atoms wherein the backbone chain of the group extends in a direct line. Preferred unbranched groups herein contain from 1 to 12 backbone atoms.

The term "cyclic" or "cyclo" as used herein alone or in combination refers to a group having one or more closed rings, whether unsaturated or saturated, possessing rings of from 3 to 12 backbone atoms, preferably 3 to 7 backbone atoms.

The term "lower" as used herein refers to a group with 1 to 6 backbone atoms.

The term "saturated" as used herein refers to a group where all available valence bonds of the backbone atoms are attached to other atoms. Representative examples of saturated groups include, but are not limited to, butyl, cyclohexyl, piperidine and the like.

The term "unsaturated" as used herein refers to a group where at least one available valence bond of two adjacent backbone atoms is not attached to other atoms. Representative examples of unsaturated groups include, but are not limited to, —CH$_2$ CH$_2$CH=CH$_2$, phenyl, pyrrole and the like.

The term "aliphatic" as used herein refers to an unbranched, branched or cyclic hydrocarbon group, which may be substituted or unsubstituted, and which may be saturated or unsaturated, but which is not aromatic. The term aliphatic further includes aliphatic groups, which comprise oxygen, nitrogen, sulfur or phosphorous atoms replacing one or more carbons of the hydrocarbon backbone.

The term "aromatic" as used herein refers to an unsaturated cyclic hydrocarbon group which may be substituted or unsubstituted having 4n+2 delocalized π(pi) electrons. The term aromatic further includes aromatic groups, which comprise a nitrogen atom replacing one or more carbons of the hydrocarbon backbone. Examples of aromatic groups include, but are not limited to, phenyl, naphthyl, thienyl, furanyl, pyridinyl, (is)oxazoyl and the like.

The term "substituted" as used herein refers to a group having one or more hydrogens or other atoms removed from a carbon or suitable heteroatom and replaced with a further group. Preferred substituted groups herein are substituted with one to five, most preferably one to three substituents. An atom with two substituents is denoted with "di," whereas an atom with more than two substituents is denoted by "poly." Representative examples of such substituents include, but are not limited to aliphatic groups, aromatic groups, alkyl, alkenyl, alkynyl, aryl, alkoxy, halo, aryloxy, carbonyl, acryl, cyano, amino, nitro, phosphate-containing groups, sulfur-containing groups, hydroxyl, alkylcarbonyloxy, arylcarbonyloxy, alkoxycarbonyloxy, aryloxycarbonyloxy, alkylcarbonyl, arylcarbonyl, alkoxycarbonyl, aminocarbonyl, alkylaminocarbonyl, dialkylaminocarbonyl, alkylthiocarbonyl, acylamino, amidino, imino, alkylthio, arylthio, thiocarboxylate, alkylsulfinyl, trifluoromethyl, azido, heterocyclyl, alkylaryl, heteroaryl, semicarbazido, thiosemicarbazido, maleimido, oximino, imidate, cycloalkyl, cycloalkylcarbonyl, dialkylamino, arylcycloalkyl, arylcarbonyl, arylalkylcarbonyl, arylcycloalkylcarbonyl, arylphosphinyl, arylalkylphosphinyl, arylcycloalkylphosphinyl, arylphosphonyl, arylalkylphosphonyl, arylcycloalkylphosphonyl, arylsulfonyl, arylalkylsulfonyl, arylcycloalkylsulfonyl, combinations thereof, and substitutions thereto.

The term "unsubstituted" as used herein refers to a group that does not have any further groups attached thereto or substituted therefore.

The term "alkyl" as used herein, alone or in combination, refers to a branched or unbranched, saturated aliphatic group. The alkyl radical may be optionally substituted independently with one or more substituents described herein. Lower alkyl refers to alkyl groups of from one to six carbon atoms. Examples of lower alkyl groups include methyl, ethyl, propyl, isopropyl, butyl, s-butyl, t-butyl, isobutyl, pentyl, and the like. Higher alkyl refers to alkyl groups containing more than seven carbon atoms. A "Co" alkyl (as in "Co—$C_6$-alkyl") is a covalent bond. Exemplary alkyl groups are those of $C_{20}$ or below. In this application, alkyl refers to alkanyl, alkenyl, and alkynyl residues (and combinations thereof); it is intended to include vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-ynyl groups; and for example, "propyl" or "$C_3$ alkyl" each include n-propyl, propenyl, and isopropyl. Representative examples of alkyl groups include, but are not limited to, methyl, ethyl, n-propyl, isopropyl, n-butyl, isobutyl, sec-butyl, tert-butyl, octyl, decyl, tetradecyl, hexadecyl, eicosyl, tetracosyl and the like. The terms "alkyl" or "alk" as used herein refer to a saturated linear or branched-chain monovalent hydrocarbon radical of one to twelve carbon atoms (C.sub.1-C.sub.12), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The terms "carbocycle", "carbocyclyl", "carbocyclic ring" and "cycloalkyl" refer to a monovalent non-aromatic, saturated or partially unsaturated ring having 3 to 12 carbon atoms (C.sub.3-C.sub.12) as a monocyclic ring or 7 to 12 carbon atoms as a bicyclic ring. The cycloalkyl radical may be optionally substituted independently with one or more substituents described herein. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "alkenyl" as used herein alone or in combination refers to a branched or unbranched, unsaturated aliphatic group containing at least one carbon-carbon double bond which may occur at any stable point along the chain. The alkenyl radical may be optionally substituted independently with one or more substituents described herein, and includes radicals having "cis" and "trans" orientations, or alternatively, "E" and "Z" orientations. Representative examples of alkenyl groups include, but are not limited to, ethenyl, E- and Z-pentenyl, decenyl and the like.

The term "alkynyl" as used herein alone or in combination refers to a branched or unbranched, unsaturated aliphatic group containing at least one carbon-carbon triple bond which may occur at any stable point along the chain. The alkynyl radical may be optionally substituted independently with one or more substituents described herein. Representative examples of alkynyl groups include, but are not limited to, ethynyl, propynyl, propargyl, butynyl, hexynyl, decynyl and the like.

The term "aryl" as used herein alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The term "alkoxy" as used herein alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy.

The term "aryloxy" as used herein alone or in combination refers to an aryl group bound through a single terminal ether linkage.

The terms "halogen", "halo" and "hal" as used herein refer to monovalent atoms of fluorine, chlorine, bromine, iodine and astatine.

The term "hetero" or "heteroatom" as used herein combination refers to a group that includes one or more atoms of any element other than carbon or hydrogen. Representative examples of hetero groups include, but are not limited to, those groups that contain heteroatoms including, but not limited to, nitrogen, oxygen, sulfur and phosphorus.

The term "heterocycle" or "heterocyclyl" or "heterocyclic ring" or "heterocyclic" as used herein refers to a cyclic group containing one or more heteroatoms. The heterocyclic radical may be optionally substituted independently with one or more substituents described herein. Representative examples of heterocycles include, but are not limited to, pyridine, piperadine, pyrimidine, pyridazine, piperazine, pyrrole, pyrrolidinone, pyrrolidine, morpholine, thiomorpholine, indole, isoindole, imidazole, triazole, tetrazole, furan, benzofuran, dibenzofuran, thiophene, thiazole, benzothiazole, benzoxazole, benzothiophene, quinoline, isoquinoline, azapine, naphthopyran, furanobenzopyranone and the like.

The term "substituent" means any group selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, halo, haloalkyl, haloalkoxy, hydroxy, oxo (valency rules permitting), lower alkanyl, lower alkenyl, lower alkynyl, alkoxy, optionally substituted cycloalkyl, optionally substituted heterocycloalkyl, optionally' substituted aryl, optionally substituted heteroaryl, alkylaminoalkyl, dialkylaminoalkyl, carboxy, carboxy ester, —C(O)NR$^5$R" (where R$^5$ is hydrogen or alkyl and R" is hydrogen, alkyl, aryl, or heterocyclyl), —NR$^5$C(O)R" (where R$^5$ is hydrogen or alkyl and R" is alkyl, aryl, or heterocyclyl), amino, alkylamino, dialkylamino, and —NHS(O)$_2$R' (where R' is alkyl, aryl, or heteroaryl).

The term "carbonyl" or "carboxy" as used herein alone or in combination refers to a group that contains a carbon-oxygen double bond. Representative examples of groups which contain a carbonyl include, but are not limited to, aldehydes (i.e., formyls), ketones (i.e., acyls), carboxylic acids (i.e., carboxyls), amides (i.e., amidos), imides (i.e., imidos), esters, anhydrides and the like.

The term "carbamate" as used herein alone or in combination refers to an ester group represented by the general structure —NH(CO)O—. Carbamate esters may have alkyl or aryl groups substituted on the nitrogen, or the amide function.

term "cyanate" "isocyanate", "thiocyanate", or "isothiocyanate" as used herein alone or in combination refers to an oxygen- or sulfur-carbon double bond carbon-nitrogen double bond. Representative examples of cyano groups include, but are not limited to, isocyanate, isothiocyanate and the like.

The term "cyano", "cyanide", "isocyanide", "nitrile", or "isonitrile" as used herein alone or in combination refers to a carbon-nitrogen triple bond.

The term "amino" as used herein alone or in combination refers to a group containing a backbone nitrogen atom. Representative examples of amino groups include, but are not limited to, alkylamino, dialkylamino, arylamino, diarylamino, alkylarylamino, alkylcarbonylamino, arylcarbonylamino, carbamoyl, ureido and the like.

The term "phosphate-containing group" as used herein refers to a group containing at least one phosphorous atom in an oxidized state. Representative examples include, but are not limited to, phosphonic acids, phosphinic acids, phosphate esters, phosphinidenes, phosphinos, phosphinyls, phosphinylidenes, phosphos, phosphonos, phosphoranyls, phosphoranylidenes, phosphorosos and the like.

The term "sulfur-containing group" as used herein refers to a group containing a sulfur atom. Representative examples include, but are not limited to, sulfhydryls, sulfenos, sulfinos, sulfinyls, sulfos, sulfonyls, thios, thioxos and the like.

The term "optional" or "optionally" as used herein means that the subsequently described event or circumstance may or may not occur, and that the description includes instances where said event or circumstance occurs and instances where it does not. For example, the phrase "optionally substituted alkyl" means that the alkyl group may or may not be substituted and that the description includes both unsubstituted alkyl and substituted alkyl.

The term "targeting agent" as used herein means any moiety whose attachment to a compound of the invention allows the increase in concentration of the compound at a site of treatment, for example, a tumor site. Examplary targeting agents include but are not limited to carbohydrates, peptides, vitamins, and antibodies.

The term "effective amount" or "effective concentration" when used in reference to a compound, product, or composition as provided herein, means a sufficient amount of the compound, product or composition to provide the desired pharmaceutical or therapeutic result. The exact amount required will vary depending on the particular compound, product or composition used, its mode of administration and the like. Thus, it is not always possible to specify an exact "effective amount." However, an appropriate effective amount may be determined by one of ordinary skill in the art informed by the instant disclosure using only routine experimentation.

The term "hydrolyzable" as used herein refers to whether the group is capable of or prone to hydrolysis (i.e., splitting of the molecule or group into two or more new molecules or groups).

The term "pharmaceutically acceptable salt" of a compound of the instant invention (e.g. Formula I) is one which is the acid addition salt of a basic compound of the invention with an inorganic or organic acid which affords a physiologically acceptable anion or which is the salt formed by an acidic compound of the invention with a base which affords a physiologically acceptable cation.

The term "prodrug" or "procompound" as used in this application refers to a precursor or derivative form of a compound of the invention that may be less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "conjugate" as used herein refers to a compound that has been formed by the joining of two or more compounds via either a covalent or non-covalent bond.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" include compounds of Formulas I-IX and stereoisomers, geometric isomers, tautomers, solvates, metabolites, and pharmaceutically acceptable salts, prodrugs, and conjugates thereof.

B. Compounds

The present invention provides in part compounds of the Formula I:

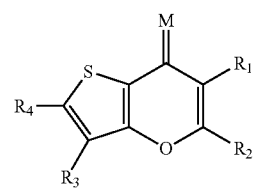

Formula I wherein M is O or S;
R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R2 is selected from R1 or

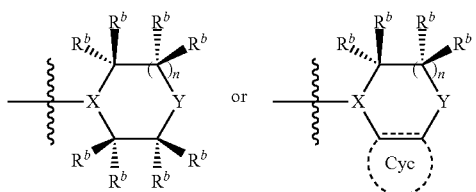

Where X is C, N, P, P(O), $SiR^b$;

n is 0, 1, or 2;

Y is C—R1, O, S, $NR^a$, —C(O)(NH$_2$), —P(Z)$_m R^a$, $SiR^a R^b$, $BR^b$;

Z is O or S;

m=0 or 1;

$R^a$ is hydrogen (H) or independently at each instance any group defined in R1;

$R^b$ is hydrogen (H) or independently at each instance any group defined in R1;

R3 is selected from R1;

R4 is selected from R1; and

Cyc is an aryl, substituted aryl, heterocycle, substituted heterocycle, carbocycle, and substituted carbocycle.

A particular compound of Formula I is one wherein a substitutent of R1 comprises a bone directing group such as, for example, amino phosphonic acid, bisphsphonate, or the like.

The present invention also provides compounds of Formulas II-IV:

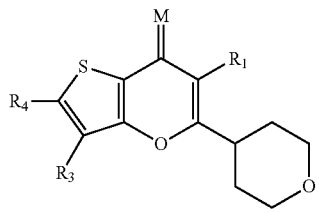

Formula II

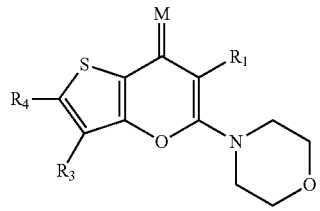

Formula III

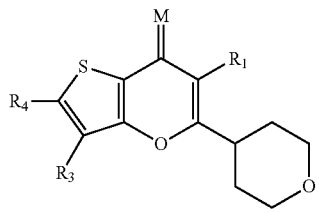

Formula IV wherein M is O or S;

R1 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;

R3 is independently, at each instance, R1; and

R4 is independently, at each instance, R1.

A particular compound of Formulas II-IV is one wherein a substitutent of R1 comprises a bone directing group such as, for example, amino phosphonic acid, bisphsphonate, or the like.

The present invention also provides compounds of Formulas V-VII:

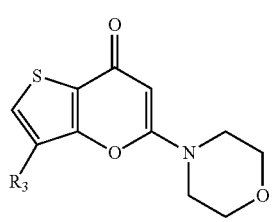

Formula V

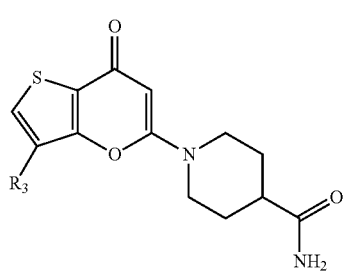

Formula VI

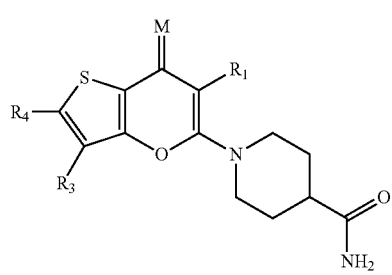

-continued

Formula VII

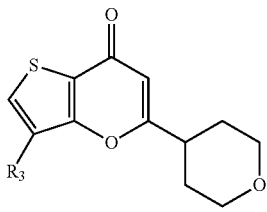

wherein R3 is selected from H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse caboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate.

A particular compound of Formulas V-VII is one wherein a substitutent of R3 comprises a bone directing group such as, for example, amino phosphonic acid, bisphsphonate, or the like. (See exemplary compounds in Table 8).

C. Conjugates

The present invention also provides conjugates of Formula I. In one embodiment conjugates are formed by alkylating a compound of Formula I with a linker group (L), the linker group optionally being substituted with a targeting agent (T). Methods for producing conjugates for this aspect of the invention include alkylation procedures disclosed in U.S. Pat. No. 6,949,537 and U.S. Pat. No. 7,396,828 the entire contents of which is herein incorporated by reference. In one embodiment of this aspect of the invention a compound of Formula I is reacted with a halomethyl ester compound of Formula Q:

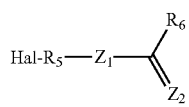

Q wherein Hal is a halogen; R5 is $CH_2$, $CH(CH_3)$, $CH(Ph)$, $C(CH_3)(COOH)$, or $CH(CH(CH_3)2)$;
Z1 and Z2 are independently S or O;
R6 is hydrogen, optionally substituted aliphatic, optionally substituted aryl, alkoxy, carboxy, amino, heterocycle, aryloxy, and optionally substituted therewith a targeting agent (T) to form R6-T.

Targeting Agent.

In another embodiment, conjugates of the present invention are those compounds wherein, $R_6$ further comprises one or more targeting agents (T) covalently attached thereto. Targeting agents allow the conjugates of the present invention to be delivered selectively to specific types of cells, tissues, organs or extracellular structures such as receptors.

In some applications it may be desirable to limit the location of a drug or prodrug to the area of treatment or at least prevent it from reaching tissues where it can cause undesirable side effects, and to ensure that at any particular time effective, but not excessive, amounts of the drug are used. The use of targeting agents may allow the conjugates of the present invention to be concentrated at the site of treatment. Once delivered to a site of treatment, the linker may be enzymatically cleaved or hydrolyzed to yield a compound of formula I. Moreover, the use of a targeting agent may limit the dosage required to achieve an effective concentration of a drug at the site of treatment. The use of targeting agents may also reduce the frequency of dosages required.

Suitable targeting agents are preferentially attached to compounds of the present invention via a covalent bond which may be formed by methods including, but not limited to, a nucleophilic or electrophilic group of the targeting agent that is covalently reacted with an electrophilic or nucleophilic group (respectively) on the linker. In one embodiment, suitable targeting agents are those disclosed in U.S. Pat. No. 6,949,537, the entire contents of which is herein incorporated by reference.

In one embodiment of the present invention, conjugates of the present invention are those compounds wherein, R6-T is selected from the group consisting of the following:

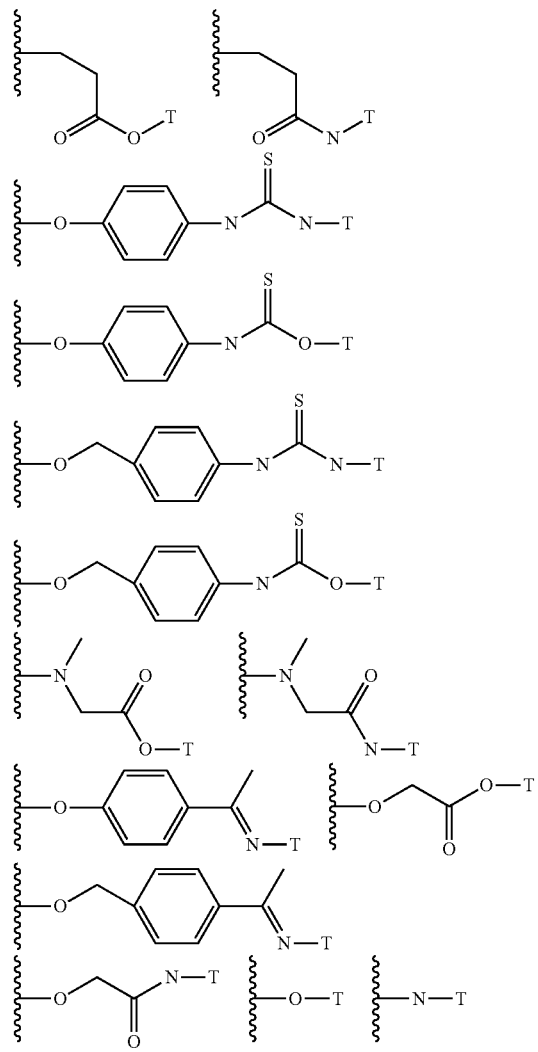

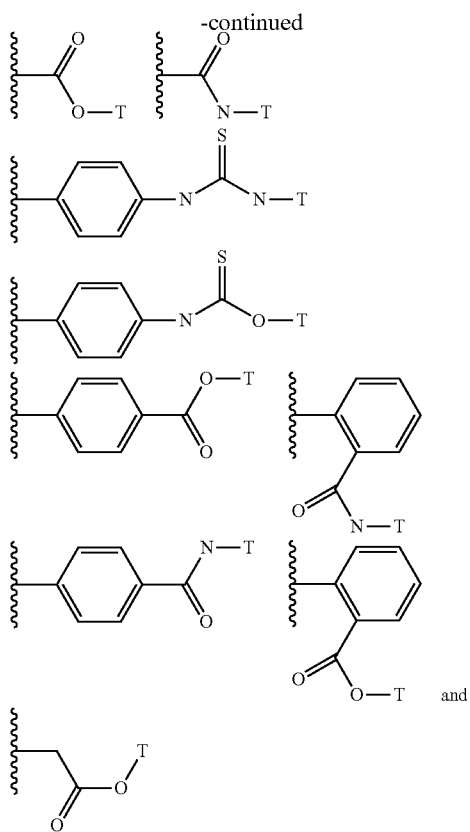

Targeting agents which may be reacted with the conjugates of the present invention include, but are not limited to, carbohydrates, vitamins, peptides, proteins, nucleosides, nucleotides, nucleic acids, liposomes, lipids, bone-seeking agents and cartilage-seeking agents. The targeting agent may also be a molecule which is bound by a receptor in a desired tissue and optionally transported into a cell by a receptor-mediated process. Representative examples of such targeting agents include, but are not limited to, diazepines that bind to peripheral benzodiazepine receptors (PBRs) present in glial cells in the brain. Representative examples of such diazepines are discussed in G. Trapani et al. *Bioconjugate Chem.* 2003, 14, 830-839 entitled "Peripheral Benzodiazepine Receptor Ligand-Melphalan Conjugates for Potential Selective Drug Delivery to Brain Tumors," the contents of which are incorporated by reference.

Representative vitamins that may be used as targeting agents include, but are not limited to, folate, vitamin B.sub.12 or vitamin C. The term "folate" encompasses folic acid derivatives with capacity to bind with folate-receptors. Representative examples of folates that may be used as targeting agents include, but are not limited to, folic acid, folinic acid, pteropolyglutamic acid, and folate receptor-binding pteridines such as tetrahydropterins, dihydrofolates, tetrahydrofolates and their deaza and dideaza analogs. Other suitable folates are folate analogs including, but not limited to, aminopterin, amethopterin (methotrexate), N.sub.10-methylfolate, 2-deamino-hydroxyfolate, deaza analogs such as 1-deazamethopterin or 3-deazamethopterin, and 3'5'-dichloro4-amino-4-deoxy-N.sub.10-methylpteroyl-glutamic acid (dichloromethotrexate). Methods of conjugating molecules to folates that are suitable for covalent attachment to compounds of the present invention are disclosed in U.S. Pat. Nos. 6,576,239, 5,820,847, 5,688,488, 5,108,921, 5,635,382, and 5,416,016 the contents of which are incorporated herein by reference. Methods of conjugating molecules to vitamin C that are suitable for covalent attachment of compounds of the present invention are disclosed in S. Manfrdini et al. *J. Med. Chem.* 2002, 45, 559-562, the contents of which are incorporated herein by reference.

Representative peptides and peptidomimetics that may be used as targeting agents include, but are not limited to, an RGD-containing peptide selected from the group consisting of RGDs, c(RGDfK), vitronectin, fibronectin, somatostatin-receptor agonists and somatostatin-receptor antagonists. Molecules that bind to the avb3 integrin receptor and act as antagonists may be used as targeting agents are described in U.S. Pat. Nos. 6,552,079, 6,426,353B, WO 2002/40505A2, and U.S. Patent Publications 2002/0055499, 2002/0061885, 2002/0065291, 2002/0072500, U.S. 2002/0072518; W. Arap et al. *Science* 1998, 279, 377-380; R. J. Kok et al. *Biojonjugate Chem.* 2002, 13, 128-135; D. A. Sipkins et al. *Nat. Med.* 1998, 4, 623-626; P. M. Winter et al. *Cancer Res.* 2003, 63, 5838-5843; and J. D. Hood et al. *Science* 2002, 296, 2404-2407; the contents of which are incorporated herein by reference. Representative proteins that may be used as targeting agents include, but are not limited to, antibodies or fragments thereof, such as a tumor-specific monoclonal antibody or fragment thereof. Representative bone-seeking agents that may be used as targeting agents include, but are not limited to, phosphonate, phosphonic acid, aminomethylphosphonic acid, phosphate, polyphosphate, and hydroxyapatite-binding polypeptides. Other peptides include chlorotoxin (U.S. Pat. No. 6,429,187B1) and tissue factor (G. M. Lanza et al. *Circulation* 2002, 106, 2842-2847).

Other suitable targeting agents include antibodies. The antibodies may be of classes IgG, IgM, IgA, IgD or IgE, or fragments or derivatives thereof, including Fab, F(ab').sub.2, Fd, and single chain antibodies, diabodies, bispecific antibodies, bifunctional antibodies and derivatives thereof. The antibody may be a monoclonal antibody, polyclonal antibody, affinity purified antibody, or mixtures thereof which exhibits sufficient binding specificity to a desired epitope or a sequence derived therefrom. The antibodies may also be a chimeric antibody. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include, but are not limited to, such antigens as are and include, but are not limited to, carcinoembryonic antigen (CEA), mucins such as TAG-72, human milk fat globule antigens, prostate serum antigent (PSA), prostate specific membrane antigen (PSMA), PS (phosphatidyl serine), and receptors including, but not limited to, the IL-2, EGF, VEGF and transferrin receptors. Other representative antigens associated with tumors include, but are not limited to, those tumor associated antigens described in J. R. Zalcberg et al. *J. Clin. Oncology* 1985, 3, 876-882, WO 01/68709A1, and U.S. Patent Publication US2004/0009122A1, the contents of which are incorporated herein by reference.

Other suitable targeting agents include glucose, galactose, mannose, mannose 6-phosphate, hormones (e.g., insulin, growth hormone, and the like), growth factors or cytokines (e.g., TGF.beta., EGF, insulin-like growth factor, and the like), YEE(GalNAcAH).sub.3 or derivatives, cobalamin, .alpha.-2 macroglobulins, asialoglycoprotein, albumin, texaphyrin, metallotexaphyrin, antibodies, antibody fragments (e.g., Fab), single-chain antibody variable region (scFv), transferrin, any vitamin and any coenzyme.

The targeting agent may also be an agent that delivers a compound of the invention to bones. Bone targeting agents include, but are not limited to, bisphosphonates, EDTMP DOTMP, and ABEDTMP, which are disclosed in U.S. Pat. Nos. 4,937,333, 4,882,142, 5,064,633 and WO-94/00143, the contents of which are incorporated herein by reference. DOTMP and EDTMP may be attached to the linker moiety by any suitable coupling method including, but not limited to, coupling chemistry where the R group can have an appropriate electrophilic or nucleophilic group that reacts with the nucleophilic or electrophilic (respectively) group of the linker moiety. Further details of the coupling chemistry are provided in *Tetrahedron* 1999, 55, 12997-13010, the contents of which are incorporated by reference. Further details of bone-targeted prodrugs and coupling chemistry are provided in *Proc. SPIE-Int. Soc. Opt. Eng.* 1999, 3600 (Biomedical Imagn. Reporters Dyes & Instrumental, 99-106; U.S. Pat. No. 5,177,054; *J. Med. Chem.* 1994, 37, 498-511; *Tetrahedron Lett.* 1989, 30. 7141-7144; T. J. Houghton et al. *J. Med. Chem.* 2008, 51, 6955-6969; and U.S. Pat. No. 5,955,453, the contents of which are incorporated by reference.

The targeting agent may be used to deliver a conjugate of the invention (or salt thereof) to bones as a slow release reservoir site for the compounds of the present invention. The targeting agent may be a bone seeking (osteotropic) moiety attached to the compounds of the present invention via an acid cleavable linker. Examples of an acid cleavable linker include, but are not limited to, an ortho acid-amide linkage. Under acidic conditions the protein-ACL-3 amide linkage is readily cleaved freeing the native amino group of the amide functionality as described in WO-94/00143 the contents of which are incorporated by reference. During osteoclastic bone resorption, which involves an acidic mediated mechanism, the attachment tethering the prodrug to bone may be cleaved releasing the compounds of the present invention. Methods and particular bone-targeting agents are disclosed in U.S. Pat. No. 6,949,537, the entire contents of which are herein incorporated by reference.

The targeting agent may also comprise an RGD peptide moiety. As discussed in F. Curnis et al. *Cancer Res.* 2004, 64, 565-571, RGD moieties target RGD fusion proteins to vasculature by interacting with cell adhesion receptors, including $\alpha v \beta_3$ integrin.

Conjugate compounds according to this aspect of the invention are depicted by Formula VIII or Formula IX wherein a hydrolyzable linker Rc is in either of two positions (as shown).

Formula VIII

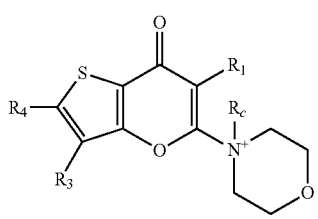

Formula IX

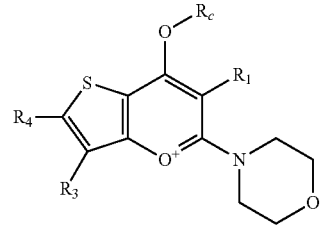

wherein R1, R3, and R4 independently represent H, F, Cl, Br, I, alkyl, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate; Rc comprises a hydrolyzable linker group (L) which is optionally substituted with a targeting agent (T).

Exemplary (but not limiting) compounds of Formula I from which conjugates according to this aspect of the invention can be made following the procedures disclosed herein are those compounds depicted in Table 8. In one embodiment, a targeted conjugate of Formula I is one in which Rc has the structure:

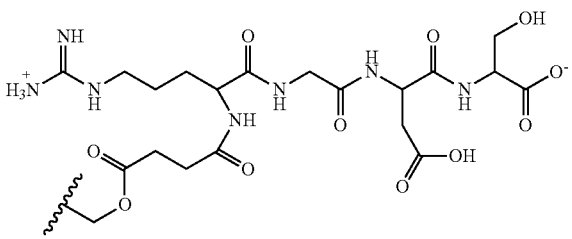 [SMILES: *COC(=O)CCC(=O)NC(CCCNC(=N)N)C(=O)NCC(=O)NC(CC(=O)O)C(=O)NC(CO)C(=O)[O-]]

A pharmaceutically acceptable salt of a compound of the instant invention is one which is the acid addition salt of a basic compound of formula I with an inorganic or organic acid which affords a physiologically acceptable anion or which is the salt formed by an acidic compound of formula I with a base which affords a physiologically acceptable cation and provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a compound of formula I, VIII, and IX (or a pharmaceutically acceptable salt thereof) as provided in any of the descriptions herein.

In addition, compounds (or salts thereof) of the present invention are useful as an active ingredient in the manufacture of a medicament for use in inhibiting kinase activity e.g. PI-3 kinase activity.

The present invention also provides a method of inhibiting kinase activity in a mammal comprising administering to a mammal in need of treatment, a kinase inhibiting dose of a compound of formula I or conjugate or prodrug thereof having any of the definitions herein.

The present invention further provides a method of inhibiting PI-3 kinase comprising administering to a mammal in need of treatment, a PI-3 kinase-inhibiting dose of a compound of formula I or conjugate or prodrug thereof having any of the definitions herein.

Further, the present invention provides a method of inhibiting tumor growth comprising administering to a mammal in need of treatment, an effective dose of a compound of formula I, or conjugate or prodrug thereof, having any of the definitions herein.

Also, there is provided a compound of formula I (or conjugate, prodrug, or salt thereof) having any of the definitions herein for use as an anticancer agent.

In addition, there is provided use of a compound of formula I having any of the definitions herein for the manufacture of a medicament, including a medicament for treatment of cancer.

As an additional feature of the invention there is provided a pharmaceutical formulation comprising in association with a pharmaceutically acceptable carrier, diluent or excipient, a conjugate of a compound of formula I (or of a pharmaceutically acceptable salt thereof) as provided in any of the descriptions herein.

The present invention also includes isotopically-labeled compounds, and pharmaceutically acceptable salts thereof, which are identical to those recited in Formulas I through IX, but replace one or more atoms by a corresponding isotope. Examples of isotopes that can be incorporated into compounds of the invention include isotopes of hydrogen, carbon, nitrogen, oxygen, phosphorous, fluorine and chlorine. Compounds of the present disclosure, conjugates thereof, and pharmaceutically acceptable salts of said compounds or of said conjugates which contain the aforementioned isotopes and/or other isotopes of other atoms are within the scope of this disclosure. Certain isotopically-labeled compounds of the present disclosure, for example those into which radioactive isotopes such as $^3$H and $^{14}$C are incorporated, are useful in drug and/or substrate tissue distribution assays for example when imaging tumors. Fluorine-18 ($^{18}$F) is particularly preferred for ease of preparation and detectability. Isotopically labeled compounds of the invention can generally be prepared by carrying out the procedures disclosed in the Schemes and/or in the Examples and Preparations below, by substituting a readily available isotopically labeled reagent for a non-isotopically labeled reagent.

It will be appreciated that certain compounds of formula I (or salts, procompounds, or conjugates etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against kinases including PI-3 kinase, it being well known in the art how to prepare or isolate particular forms and how to determine inhibitory properties against kinases by standard tests including those described herein below.

In addition, a compound of formula I (or salt, procompound or conjugate thereof, etc.) may exhibit polymorphism or may form a solvate with water or an organic solvent. The present invention also encompasses any such polymorphic form, any solvate or any mixture thereof.

As mentioned above, the invention includes a pharmaceutically acceptable salt of a compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

D.1. Synthesis of Compounds and Conjugates

The compounds of the present invention may be prepared by processes known in the chemical art. Starting materials and intermediates used to prepare a compound of the invention are either commercially available or can be prepared by one of ordinary skill in the art.

The compounds of the invention, or their pharmaceutically acceptable salts, may have asymmetric carbon atoms or quaternized nitrogen atoms in their structure. It will be appreciated that certain compounds of Formula I (or salts, conjugates, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as a mixture thereof; or as a mixture of diastereomers, as well as in the form of an individual diastereomer, and that the present invention encompasses a compound of Formula I as a mixture of entantiomers, as well as in the form of an individual enantiomer, any of which mixtures or form possesses inhibitory properties against kinases, for example PI-3 kinases. The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of the invention.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using other conventional techniques. For example, enantiomers (R- and S-isomers) may be resolved by formation of diastereoisomeric salts or complexes which may be separated, for example, by crystallization; via formation of diastereoisomeric derivatives which may be separated, for example, by crystallization; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, a specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

A compound of Formula I in which R1 and R4 are hydrogen and R2 and R3 have the meanings defined hereinabove may be synthesized as illustrated by Scheme I.

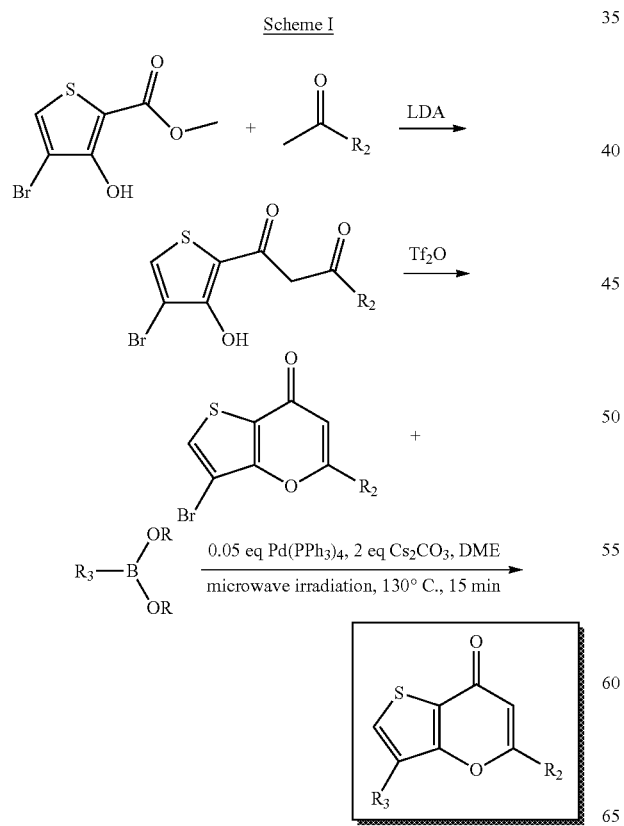

Another route to make a compound of Formula I in which R1 and R4 are hydrogen and R2 and R3 have the meanings defined hereinabove may be synthesized as illustrated by Scheme II.

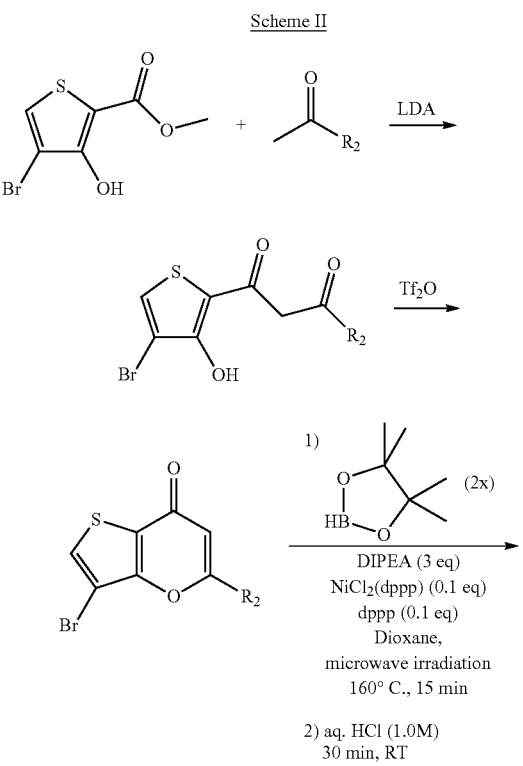

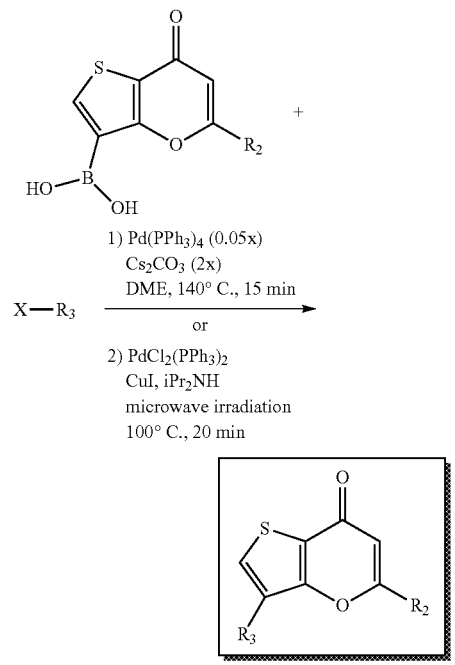

Another route to make a compound of Formula I in which R1 and R4 are hydrogen and R2 and R3 have the meanings defined herein above may be synthesized as illustrated by Scheme III.

Scheme III

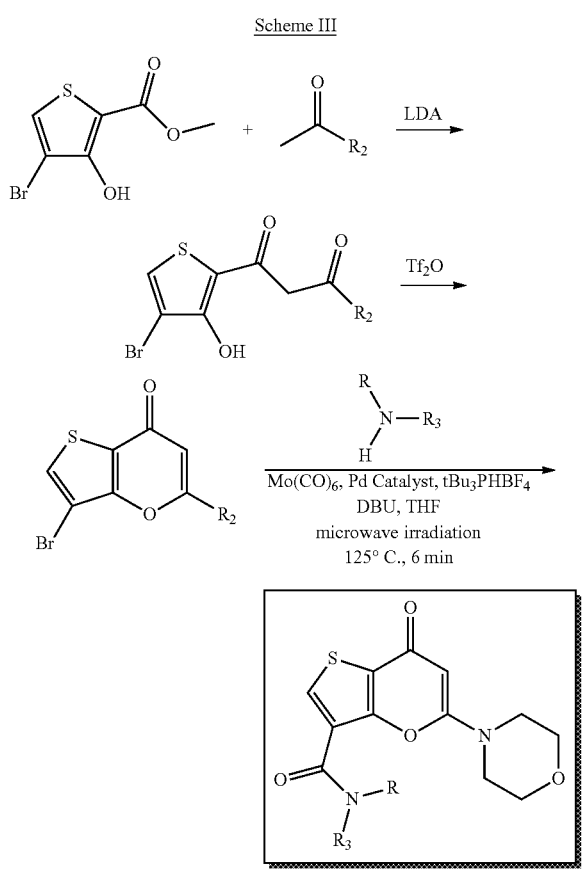

Another route to make a compound of Formula I in which R1 and R4 are hydrogen and R2 and R3 have the meanings defined hereinabove may be synthesized as illustrated by Scheme IV.

Scheme IV

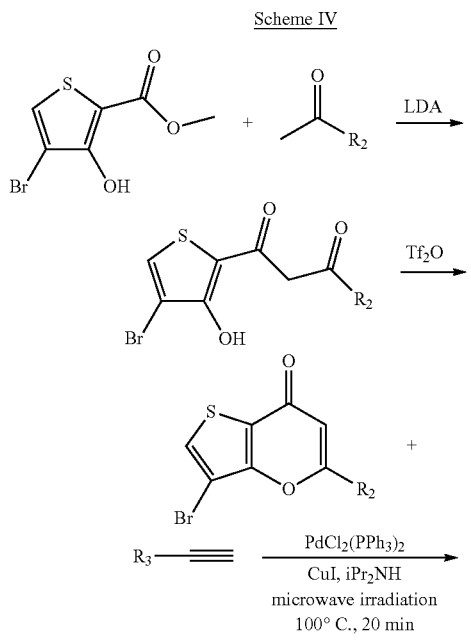

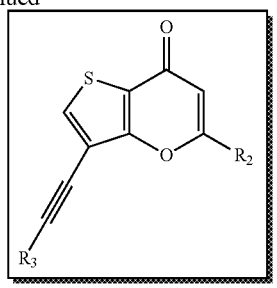

If methyl 4-bromo-3-hydroxythiophene-2-carboxylate is reacted with 1-morpholinoethanone in Scheme I compounds of Formula V are produced:

Formula V

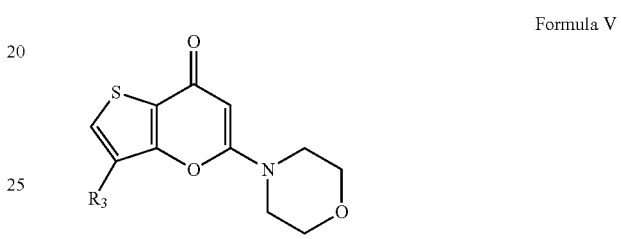

A compound of Formula I-VII wherein a substituent of R1 (R3 for Formulas V-VII) further comprises a bone-directing group such as, for example, amino phosphonic acid, bisphosphonate, or the like, can be made by procedures known in the art including, for example, the procedures disclosed in T. J. Houghton et al. J. Med. Chem. 2008, 51, 6955-6969, the entire contents of which is herein incorporated by reference.

D.2. Synthesis of Conjugates

Conjugates of the invention can be made, for example, by the procedures disclosed in U.S. Pat. Nos. 6,949,537 and 7,396,828, the entire contents of which are herein incorporated by reference.

E. Formulations

As an additional aspect of the invention there is provided a pharmaceutical formulation or composition comprising in association with a pharmaceutically acceptable carrier, diluent or excipient, a compound of the invention, e.g. Formula I (or a pharmaceutically acceptable salt or procompound or conjugate thereof) as provided in any of the descriptions herein. Compositions of the present invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

Compositions of the present invention may also be liquid formulations including, but not limited to, aqueous or oily suspensions, solutions, emulsions, syrups, and elixirs. The compositions may also be formulated as a dry product for constitution with water or other suitable vehicle before use. Such liquid preparations may contain additives including, but not limited to, suspending agents, emulsifying agents, nonaqueous vehicles and preservatives. Suspending agent include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

Compositions of the present invention may also be formulated as suppositories, which may contain suppository bases including, but not limited to, cocoa butter or glycerides. Compositions of the present invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of the present invention may also be formulated transdermal formulations comprising aqueous or nonaqueous vehicles including, but not limited to, creams, ointments, lotions, pastes, medicated plaster, patch, or membrane.

Compositions of the present invention may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of the present invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of the present invention may also be formulated as a liposome preparation. The liposome preparation can comprise liposomes which penetrate the cells of interest or the stratum corneum, and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used. Other suitable formulations can employ niosomes. Niosomes are lipid vesicles similar to liposomes, with membranes consisting largely of non-ionic lipids, some forms of which are effective for transporting compounds across the stratum corneum.

The following formulation examples are illustrative only and are not intended to limit the scope of the invention in any way. The phrase "active ingredient" refers herein to a compound according to formula I or a pharmaceutically acceptable salt, procompound, conjugate, or solvate thereof

| Formulation 1: Tablet containing the following components: | |
|---|---|
| Ingredient | Amount (mg/tablet) |
| Active ingredient | 250 |
| Dried starch | 200 |
| Magnesium stearate | 10 |
| Total | 460 mg |

| Formulation 2: Capsules containing the following components: | |
|---|---|
| Ingredient | Amount (mg/tablet) |
| Active ingredient | 60 |
| Dried starch | 44 |
| Magnesium stearate | 1.5 |
| Microcrystalline cellulose | 44 |
| Total | 150 mg |

Parenteral dosage forms for administration to patients by various routes including, but not limited to, subcutaneous, intravenous (including bolus injection), intramuscular, and intra-arterial are also contemplated by the present invention. Parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

An example parenteral composition of the invention would be intended for dilution with aqueous solution(s) comprising for example 5% Dextrose Injection, USP, or 0.9% Sodium Chloride Injection, USP, prior to administration to a patient, and is an aqueous solution that comprises irinotecan, sorbitol NF powder, and lactic acid, USP, and has a pH of from about 3.0 to about 3.8.

F. Therapeutic Use

The present invention also encompasses medical use of compounds of the present invention including methods of treatment of a patient suffering from a condition or disease associated with aberrant kinase activity including PI-3 kinase. In one aspect, kinase activity may be abnormal, excessive, or constitutively active in a patient in need of such treatment. The present invention also relates to a method for treating inflammatory disease comprising administering to a patient in need thereof a therapeutically effective amount of a compound of the present invention. Exemplary, but non-exclusive diseases and adverse health conditions attributable to kinase activity, in particular inappropriate PI-3 kinase signaling activity, have been disclosed in the art, for example U.S. 2002/0150954A1; U.S. Pat. Nos. 5,504,103; 6,518,277B1; 6,403,588; 6,482,623; 6,518,277;

6,667,300; U.S.20030216389; U.S.20030195211; U.S.20020037276 and U.S. Pat. No. 5,703,075 the contents of which are herein incorporated by reference.

The compounds of the invention can have utility in the treatment of CNS disorders, including schizophrenia, episodic paroxysmal anxiety (EPA) disorders such as obsessive compulsive disorder (OCD), post traumatic stress disorder (PTSD), phobia and panic, major depressive disorder, bipolar disorder, Parkinson's disease, general anxiety disorder, autism, delirium, multiple sclerosis, Alzheimer disease/dementia and other neurodegenerative diseases, severe mental retardation, dyskinesias, Huntington's disease, Tourett's syndrome, tics, tremor, dystonia, spasms, anorexia, bulimia, stroke, addiction/dependency/craving, sleep disorder, epilepsy, migraine; and attention deficit/hyperactivity disorder (ADHD).

In another aspect, the present invention provides a method for treating Alzheimer's Disease comprising administering to a patient in need thereof a therapeutically effective amount of a compound of the present invention. It has been reported that increasing PIP2 concentrations by, for example, inhibiting PI-3 kinase decreases levels of neurotoxins associated with Alzheimer's Disease. (US 2008/0312187; incorporated herein by reference).

In another aspect, the present invention provides a method for enhancing the chemosensitivity of tumor cells comprising administering to a patient in need thereof a therapeutically effective amount of a compound of the present invention.

In another aspect, the present invention provides a method for enhancing the radiosensitivity of tumor cells comprising administering to a patient in need thereof a therapeutically effective amount of a compound of the present invention.

In another aspect, the present invention provides a method for inhibiting or reducing tumor growth comprising administering to a patient in need thereof a therapeutically effective amount of a compound of the present invention.

In another aspect, the present invention provides a method for inducing oxidative stress in tumor cells comprising administering to a patient in need thereof a therapeutically effective amount of a compound of the present invention.

In another aspect, the present invention provides a method for inhibiting or reducing tumor growth by inhibiting cancer stem cell growth and/or proliferation comprising administering to a patient in need thereof a therapeutically effective amount of a compound of the present invention.

In another aspect, the present invention provides a method for inhibiting tumor induced angiogenesis comprising administering to a patient in need thereof a therapeutically effective amount of a compound of the present invention.

Further, the present invention provides a method for inhibiting angiogenesis associated with non-cancer diseases comprising administering to a patient in need thereof a therapeutically effective amount of a compound of the present invention.

In yet another aspect, the present invention provides a therapeutic method for increasing apoptosis in cancer cells and cancerous tumors comprising administering to a patient in need thereof a therapeutically effective amount of a compound of the present invention.

The present invention also provides a method of treating cancer comprising administering to a patient in need thereof a therapeutically effective amount of a compound of the present invention.

A variety of cancers may be treated according to the present invention including, but not limited to: carcinoma of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xeroderma pigmentosum, keratoactanthoma, seminoma, thyroid follicular cancer, and teratocarcinoma. The methods of the invention may also be used to treat accelerated or metastatic cancers of the bladder, pancreatic cancer, prostate cancer, non-small cell lung cancer, colorectal cancer, and breast cancer.

A compound of the invention may be administered simultaneously or metronomically with other anti-cancer treatments such as chemotherapy and radiation therapy. The term "simultaneous" or "simultaneously" as used herein, means that the other anti-cancer treatment and the compound of the present invention are administered within 48 hours, preferably 24 hours, more preferably 12 hours, yet more preferably 6 hours, and most preferably 3 hours or less, of each other. The term "metronomically" as used herein means the administration of the compounds at times different from the chemotherapy and at a certain frequency relative to repeat administration and/or the chemotherapy regimen.

The chemotherapy treatment may comprise administration of a cytotoxic agent or cytostatic agent, or combination thereof. Cytotoxic agents prevent cancer cells from multiplying by: (1) interfering with the cell's ability to replicate DNA and (2) inducing cell death and/or apoptosis in the cancer cells. Cytostatic agents act via modulating, interfering or inhibiting the processes of cellular signal transduction which regulate cell proliferation and sometimes at low continuous levels.

Classes of compounds that may be used as cytotoxic agents include but are not limited to the following: alkylating agents (including, without limitation, nitrogen mustards, ethylenimine derivatives, alkyl sulfonates, nitrosoureas and triazenes): uracil mustard, chlormethine, cyclophosphamide (Cytoxan®), ifosfamide, melphalan, chlorambucil, pipobroman, triethylene-melamine, triethylenethiophosphoramine, busulfan, carmustine, lomustine, streptozocin, dacarbazine, and temozolomide; antimetabolites (including, without limitation, folic acid antagonists, pyrimidine analogs, purine analogs and adenosine deaminase inhibitors): methotrexate, 5-fluorouracil, floxuridine, cytarabine, 6-mercaptopurine, 6-thioguanine, fludarabine phosphate, pentostatine, and gemcitabine; natural products and their derivatives (for example, vinca alkaloids, antitumor antibiotics, enzymes, lymphokines and epipodophyllotoxins): vinblastine, vincristine, vindesine, bleomycin, dactinomycin, daunorubicin, doxorubicin, epirubicin, idarubicin, ara-c, paclitaxel (paclitaxel is commercially available as Taxol®), mithramycin, deoxyco-formycin, mitomycin-c, l-asparaginase, interferons (preferably IFN-.alpha.), etoposide, and teniposide. Other proliferative cytotoxic agents are navelbene, CPT-11, anastrazole, letrazole, capecitabine, reloxafine, cyclophosphamide, ifosamide, and droloxafine.

Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, (1996) Science, 274:2009) estramustine, nocodazole, MAP4, and the like. Examples of such agents are also described in J. C. Bulinski et al. *J. Cell Sci.* 1997, 110, 3055-3064; D. Panda et al. *Proc. Natl. Acad. Sci. USA* 1997, 94, 10560-10564; P. F. Mühlradt et al. *Cancer Res.* 1997, 57, 3344-3346; K. C. Nicolaou et al. *Nature* 1997, 387, 268-272; R. J. Vasquez et al. *Mol. Biol. Cell.* 1997, 8, 973-985; and D. Panda et al. *J. Biol. Chem.* 1996, 271, 29807-29812.

Other suitable cytotoxic agents include but are not limited to epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Cytostatic agents that may be used according to the invention include, but are not limited to, hormones and steroids (including synthetic analogs): 17 alpha-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, zoladex. Other cytostatic agents are antiangiogenics such as matrix metalloproteinase inhibitors, and other VEGF inhibitors, such as anti-VEGF antibodies and small molecules such as ZD6474 and SU6668 are also included. Anti-Her2 antibodies from Genentech may also be utilized. A suitable EGFR inhibitor is EKB-569 (an irreversible inhibitor). Also included are Imclone antibody C225 immunospecific for the EGFR, and src inhibitors. Also suitable for use as a cytostatic agent is Casodex® (bicalutamide, Astra Zeneca) which renders androgen-dependent carcinomas non-proliferative. Yet another example of a cytostatic agent is the antiestrogen Tamoxifen® which inhibits the proliferation or growth of estrogen dependent breast cancer. Inhibitors of the transduction of cellular proliferative signals are cytostatic agents. Representative examples include but are not limited to epidermal growth factor inhibitors, Her-2 inhibitors, MEK-1 kinase inhibitors, MAPK kinase inhibitors, PI3 inhibitors, Src kinase inhibitors, and PDGF inhibitors.

The present invention also encompasses a method for treating pancreatitis comprising administering to a patient in need thereof a therapeutically effective amount of a compound of the present invention. As discussed in I. Gukovsky et al. *Gastroenterology* 2004, 126, 554-566, inhibition of PI-3 kinase may prevent pancreatitis.

The present invention also encompasses a method for treating ulcers comprising administering to a patient in need thereof a therapeutically effective amount of a compound of the present invention. The present invention also encompasses a method for treating gastric cancer, such as stomach cancer, comprising administering to a patient in need thereof a therapeutically effective amount of a compound of the present invention. As discussed in Bacon et al., Digestive Disease Week Abstracts and Itinerary Planner, Vol. 2003, Abstract No. M921 (2003) and Rokutan et al., Digestive Disease Week Abstracts and Itinerary Planner, Vol. 2003, Abstract No. 354 (2003), PI-3 kinase is involved in the adhesion of Helicobacterpylori to gastric cells.

The present invention also encompasses a method for treating age-related macular degeneration (AMD) comprising administering to a patient in need thereof a therapeutically effective amount of a compound of the present invention. As discussed in Retina, Feb. 18, 2004, inhibition of VEGF inhibits blood vessel overgrowth associated with AMD. The compounds of the present invention may treat AMD by inhibiting angiogenesis.

The present invention also encompasses a method for treating conditions associated with a mutant PTEN comprising administering to a patient in need thereof a therapeutically effective amount of a compound of the present invention. PTEN is a tumor suppressor gene located on chromosome 10q23, in which mutations have been identified in patients with Cowden disease. As discussed in A. Vega et al. *J. Invest. Dermatol.* 2003, 121, 1356-1359, mutations in PTEN have reduced ability to inhibit the activation of the proto-oncogene AKT Inhibitors of PI-3 kinase may inhibit phosphorylation of AKT, thereby reducing the deleterious effect of mutant PTEN.

G. Administration and Dosage

A compound or composition of the present invention may be administered in any manner including but not limited to orally, parenterally, sublingually, transdermally, rectally, transmucosally, topically, pulmonarily, nasally, or bucally. Parenteral administration includes but is not limited to intravenous, intraarterial, intraperitoneal, subcutaneous, intramuscular, intrathecal, and intraarticular. The compound or compositions of the invention may also be administered via slow controlled i.v. infusion or by release from an implant device.

A therapeutically effective amount of a compound of the invention required for use in therapy varies with the nature of the condition being treated, the length of treatment time desired, the age and the condition of the patient, and is ultimately determined by the attending physician. In general, however, doses employed for adult human treatment typically are in the range of 0.001 mg/kg to about 200 mg/kg per day. The dose may be about 1 µg/kg to about 100 µg/kg per day. The desired dose may be conveniently administered in a single dose, or as multiple doses administered at appropriate intervals, for example as two, three, four or more sub-doses per day. Multiple doses often are desired, or required.

A number of factors may lead to the compounds of the present invention being administered over a wide range of dosages. When given in combination with other therapeutic agents, the dosage of the compounds of the present invention may be given at relatively lower dosages. In addition, the use of targeting agents on a conjugate of the invention is expected to lower the effective dosage required for treatment. As a result, the daily dosage of a compound of the present invention may be from about 1 ng/kg to about 100 mg/kg. The dosage of a compound of the present invention may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400

μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, or 100 mg/kg.

The present invention has multiple aspects, illustrated by the following non-limiting examples. The examples are merely illustrative and do not limit the scope of the invention in any way.

H. Preparation of Compounds

Synthesis of 1-(4-bromo-3-hydroxythiophen-2-yl)-3-morpholinopropane-1,3-dione

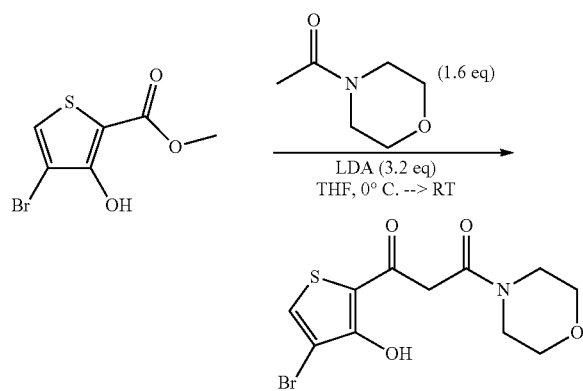

An oven-dried 100 mL round-bottom flask was charged with a magnetic stirring bar, tetrahydrofuran (5 mL) and lithium diisopropylamide (2.0M in hexanes, 6.7 mL, 13.5 mmol). The reaction mixture was magnetically stirred and cooled to 0° C. under argon gas. A solution of N-acetylmorpholine (6.75 mmol) in tetrahydrofuran (1 mL) was added, and the reaction was stirred at 0° C. for 1 hour. A solution of methyl 4-bromo-3-hydroxythiophene-2-carboxylate (4.22 mmol) in tetrahydrofuran (2 mL) was added dropwise over 5 minutes and the reaction was allowed to warm to room temperature overnight. The reaction was quenched by the addition of aqueous 10% hydrochloric acid solution (20 mL). The resulting solution was transferred to a separatory funnel, diluted with water (80 mL), and extracted three times with dichloromethane (100 mL). The organic layers were combined, dried over magnesium sulfate, filtered, and concentrated in vacuo to give 1-(4-bromo-3-hydroxythiophen-2-yl)-3-morpholinopropane-1,3-dione (1.95 g, 5.83 mmol, 138% yield) as a brown solid.

Synthesis of 3-bromo-5-morpholino-7H-thieno[3,2-b]pyran-7-one

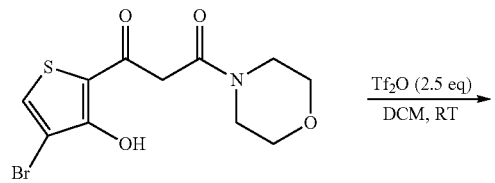

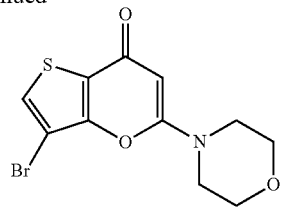

103

An oven-dried 100 mL round-bottom flask was charged with a magnetic stirring bar, 1-(4-bromo-3-hydroxythiophen-2-yl)-3-morpholinopropane-1,3-dione (1.95 g, 5.83 mmol) and dissolved in dichloromethane (30 mL) under magnetic stirring. Trifluoromethanesulfonic anhydride (2.45 mL, 14.6 mmol) was added portionwise over 2 minutes, and the reaction was stirred at room temperature. After stirring overnight, the reaction was concentrated in vacuo and redissolved in methanol (10 mL). After stirring for 4 hours, the reaction was concentrated in vacuo and diluted with aqueous 5% sodium bicarbonate solution (100 mL). The reaction was transferred to a separatory funnel and extracted three times with dichloromethane (100 mL). The organic layers were combined, dried over magnesium sulfate, filtered, and concentrated in vacuo to give 3-bromo-5-morpholino-7H-thieno[3,2-b]pyran-7-one (103) (1.52 g, 4.81 mmol, 82%) as a brown solid.

Suzuki Coupling Reaction Procedure A

Synthesis of 5-morpholino-3-phenyl-7H-thieno[3,2-b]pyran-7-one (6)

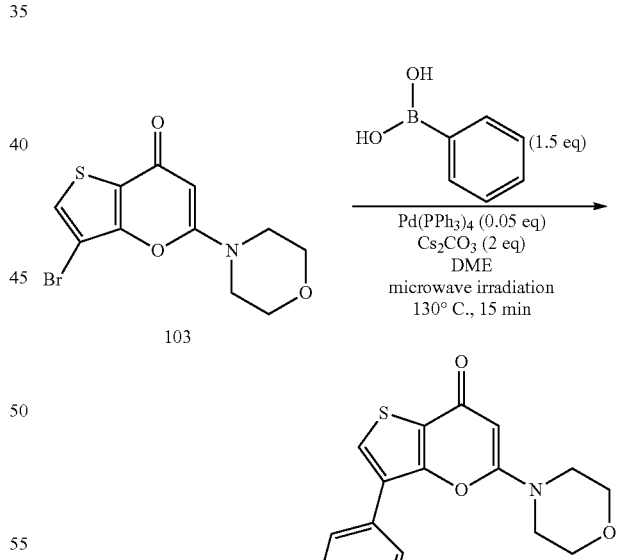

A 2 mL conical microwave vial was charged with a magnetic stirring bar, 3-bromo-5-morpholino-7H-thieno[3,2-b]pyran-7-one (103) (50 mg, 0.16 mmol), phenylboronic acid (29 mg, 0.24 mmol), cesium carbonate (103 mg, 0.32 mmol), tetrakis(triphenylphosphine)palladium(0) (9 mg, 0.008 mmol), and dimethoxyethane (1 mL). The reaction mixture was magnetically stirred and heated via microwave irradiation for 15 minutes at 130° C. Upon cooling to room temperature, the reaction was concentrated in vacuo and purified using high-pressure liquid chromatography to give 5-morpholino-3-phenyl-7H-thieno[3,2-b]pyran-7-one (6) (10 mg, 3.2 µmol) as a white solid.

Suzuki Coupling Reaction Procedure B

Synthesis of 5-morpholino-3-(pyridin-3-yl)-7H-thieno[3,2-b]pyran-7-one (3)

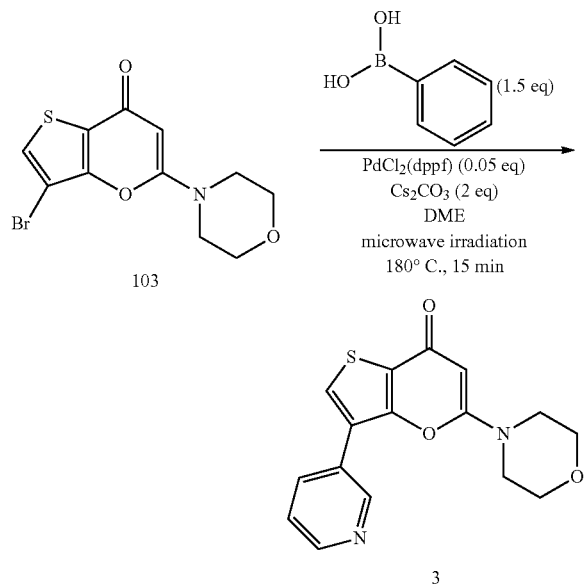

A 2 mL conical microwave vial was charged with a magnetic stirring bar, 3-bromo-5-morpholino-7H-thieno[3,2-b]pyran-7-one (103) (50 mg, 0.16 mmol), 3-pyridylboronic acid (29 mg, 0.24 mmol), cesium carbonate (103 mg, 0.32 mmol), dichloro[1,1'-bis(diphenylphosphino)ferrocene]palladium(II) dichloromethane adduct (9 mg, 0.008 mmol), and dimethoxyethane (1 mL). The reaction mixture was magnetically stirred and heated via microwave irradiation for 15 minutes at 180° C. Upon cooling to room temperature, the reaction was concentrated in vacuo and purified using high-pressure liquid chromatography to give 5-morpholino-3-(pyridin-3-yl)-7H-thieno[3,2-b]pyran-7-one (3) (6 mg, 1.9 µmol) as a white solid.

Sonogashira Coupling Reaction Procedure C 5-morpholino-3-(phenylethynyl)-7H-thieno[3,2-b]pyran-7-one (31)

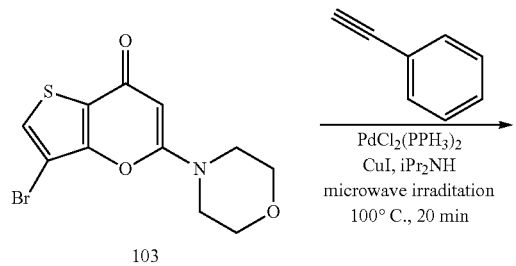

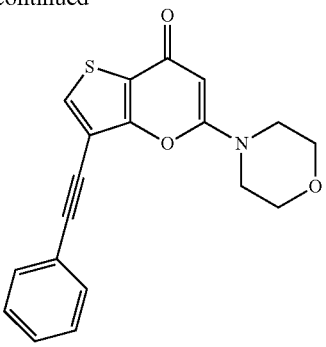

A microwave vial was charged with a magnetic stirring bar, 3-bromo-5-morpholino-7H-thieno[3,2-b]pyran-7-one (103) (50 mg, 158.1 µmol), phenylacetylene (32.0 mg, 316.2 µmol), trans-dichlorobis(triphenylphosphine)palladium (II) (5.6 mg, 7.9 µmol), copper (I) iodide (1.6 mg, 7.9 µmol) and diisopropylamine (1.0 mL). The mixture was magnetically stirred and heated via microwave irradiation to 100° C. for 20 minutes. The mixture was cooled to room temperature, and then concentrated in vacuo resulting in a brown solid. The solid was dissolved in methanol (1.0 mL) and loaded onto Isolute functionalized silica column (PE-AX/SCX-2). The column was washed with methanol and 7N methanolic ammonia. The methanolic ammonia fractions were combined and concentrated in vacuo. The resulting solid was purified using preparative high-pressure liquid chromatography to give 5-morpholino-3-(phenylethynyl)-7H-thieno[3,2-b]pyran-7-one (31) (24.0 mg, 71.1 µmol) as an orange solid.

Aminocarbonylation Reaction Procedure D 5-morpholino-7-oxo-N-phenyl-7H-thieno[3,2-b]pyran-3-carboxamide (51)

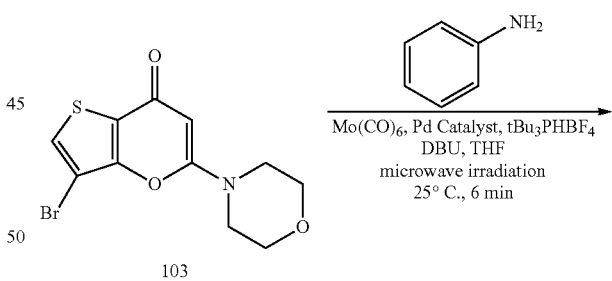

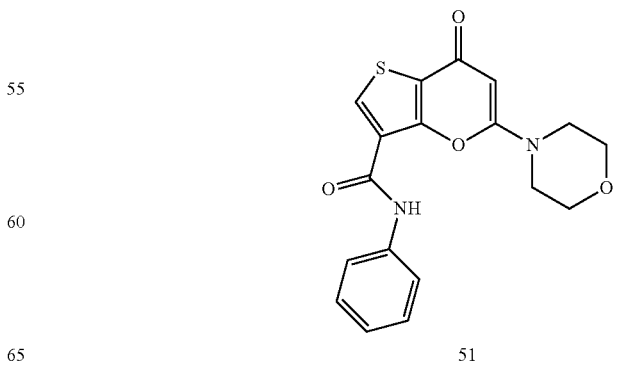

A 2 mL microwave vial was charged with a magnetic stirring bar, 3-bromo-5-morpholino-7H-thieno[3,2-b]pyran-7-one (103) (100 mg, 316 μmol), molybdenumhexacarbonyl (42 mg, 160 μmol), trans-di(μ-acetato)bis[o-(di-o-tolyl-phosphino)benzyl]dipalladium (II) (4.6 mg, 4.9 μmol), tri-tert-butylphosphonium tetrafluoroborate (2.8 mg, 12.0 μmol), tetrahydrofuran (500 μL), aniline (45 μL, 483 μmol) and 1,8-diazabicyclo[5.4.0]undec-7-ene (32 μL, 210 μmol). The vial was immediately sealed, magnetically stirred and heated via microwave irradiation to 125° C. for 6 minutes. The mixture was cooled to room temperature, and loaded onto Isolute functionalized silica column (PE-AX/SCX-2). The column was washed with methanol and the product was eluted with 7N methanolic ammonia. The methanolic ammonia fractions were combined and concentrated in vacuo. The resulting solid was purified using preparative high-pressure liquid chromatography to give 5-morpholino-7-oxo-N-phenyl-7H-thieno[3,2-b]pyran-3-carboxamide (51), (3.88 mg, 10.9 μmol) as a yellow solid.

Reverse Suzuki Coupling Reaction Procedure E

Synthesis of 5-morpholino-7-oxo-7H-thieno[3,2-b]pyran-3-ylboronic acid

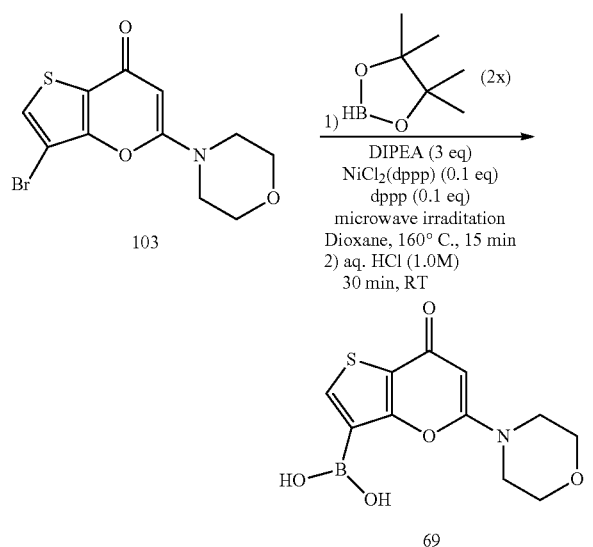

A 20 mL microwave vial was charged with a magnetic stirring bar, 3-bromo-5-morpholino-7H-thieno[3,2-b]pyran-7-one (103) (1.20 g, 3.80 mmol), 1,3-bis(diphenylphosphino)propane (156 mg, 0.38 mmol), 1,3-bis(diphenylphosphino)propane nickel(II) chloride (205 mg, 0.38 mmol), dioxane (8 mL), diisopropylethylamine (1.98 mL, 11.39 mmol), and 4,4,5,5-tetramethyl-1,3,2-dioxaborolane (1.10 mL, 7.59 mmol). The reaction mixture magnetically stirred and heated via microwave irradiation for 15 minutes at 160° C. Upon cooling to room temperature, the reaction was transferred to a reparatory funnel, diluted with dichloromethane (100 mL), and washed three times with saturated aqueous ammonium chloride solution (100 mL). The dichloromethane layer was dried over magnesium sulfate, filtered, and concentrated in vacuo. The resulting brown foam was stirred in aqueous hydrochloric acid (1.0M, 100 mL) for 30 minutes, frozen, and lyophilized to give 5-morpholino-7-oxo-7H-thieno[3,2-b]pyran-3-ylboronic acid (69) (1.51 g, 4.15 mmol) as a brown solid.

Synthesis of methyl 3-hydroxy-4-(5-morpholino-7-oxo-7H-thieno[3,2-b]pyran-3-yl)thiophene-2-carboxylate (21)

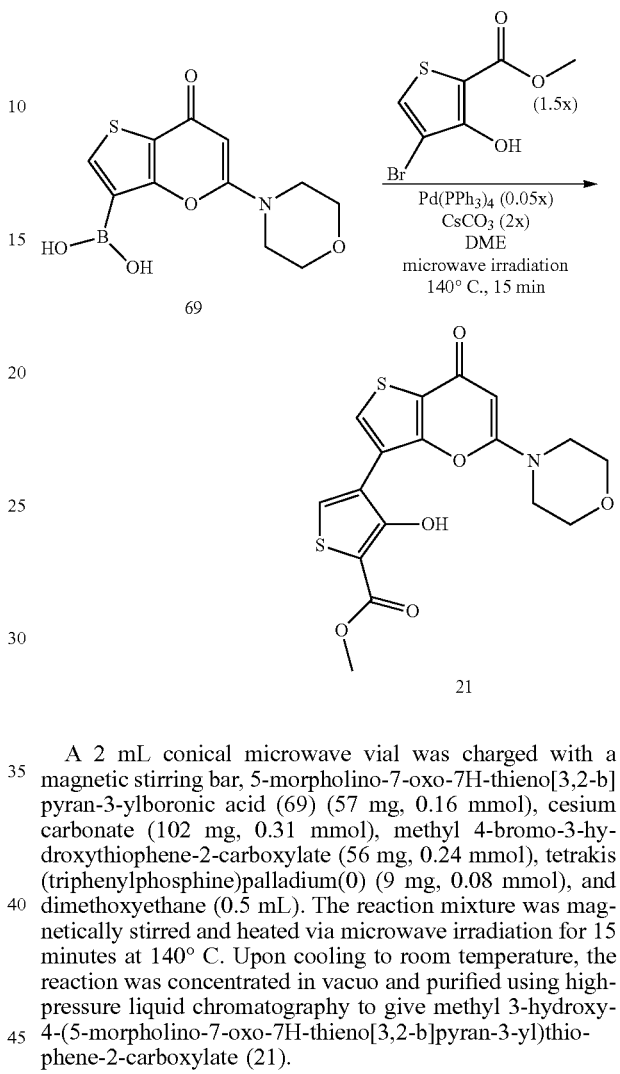

A 2 mL conical microwave vial was charged with a magnetic stirring bar, 5-morpholino-7-oxo-7H-thieno[3,2-b]pyran-3-ylboronic acid (69) (57 mg, 0.16 mmol), cesium carbonate (102 mg, 0.31 mmol), methyl 4-bromo-3-hydroxythiophene-2-carboxylate (56 mg, 0.24 mmol), tetrakis(triphenylphosphine)palladium(0) (9 mg, 0.08 mmol), and dimethoxyethane (0.5 mL). The reaction mixture was magnetically stirred and heated via microwave irradiation for 15 minutes at 140° C. Upon cooling to room temperature, the reaction was concentrated in vacuo and purified using high-pressure liquid chromatography to give methyl 3-hydroxy-4-(5-morpholino-7-oxo-7H-thieno[3,2-b]pyran-3-yl)thiophene-2-carboxylate (21).

Acylation Reaction Procedure F

Synthesis of N-(4-(5-morpholino-7-oxo-7H-thieno[3,2-b]pyran-3-yl)phenyl)nicotinamide (30)

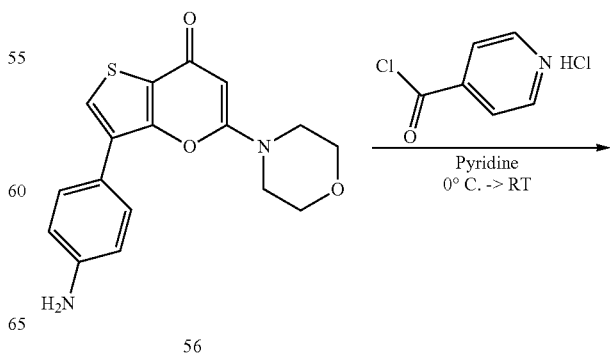

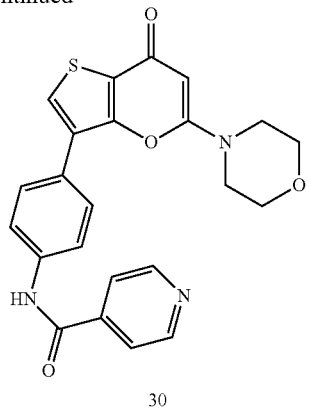

30

A 40 mL vial was charged with a magnetic stirring bar, 3-(4-aminophenyl)-5-morpholino-7H-thieno[3,2-b]pyran-7-one (56) (200 mg, 609 µmol) and pyridine (5 mL). The mixture was magnetically stirred and cooled to 0° C. in an ice bath. Isonicotinoyl chloride hydrochloric acid (669 µmol) was added and the reaction was stirred at room temperature for 30 minutes. The reaction was diluted with dichloromethane (15 mL) and washed three times with saturated aqueous sodium bicarbonate solution (15 mL). The dichloromethane layer was dried over magnesium sulfate, filtered, and concentrated in vacuo to give N-(4-(5-morpholino-7-oxo-7H-thieno[3,2-b]pyran-3-yl)phenyl)nicotinamide (30) (94 mg, 217 µmol) as a yellow solid.

Aminocarbonylation Reaction Procedure G

Synthesis of N-benzyl-4-(5-morpholino-7-oxo-7H-thieno[3,2-b]pyran-3-yl)benzamide (50)

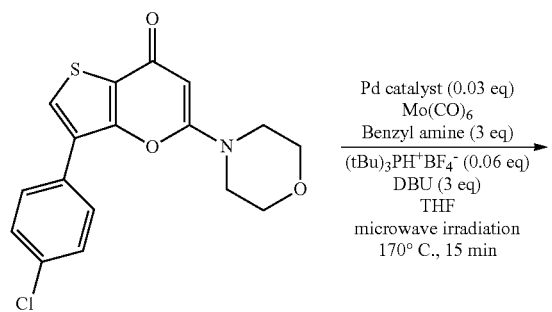

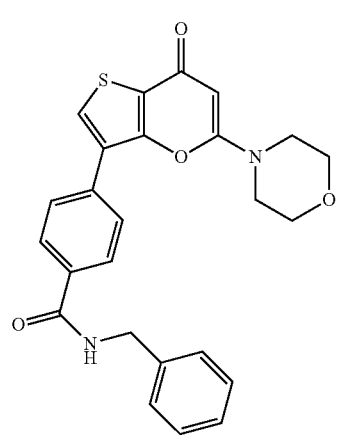

50

A 2 mL conical microwave vial was charged with a magnetic stirring bar, 3-(4-chlorophenyl)-5-morpholino-7H-thieno[3,2-b]pyran-7-one (17) (80 mg, 230 µmol), trans-di(µ-acetato)bis[o-(di-o-tolyl-phosphino)benzyl]dipalladium (II) (6 mg, 7 µmol), tri-tert-butylphosphonium tetrafluoroborate (4 mg, 14 µmol), molybdenumhexacarbonyl (61 mg, 230 µmol), tetrahydrofuran (500 µL), benzyl amine (75 µL, 690 µmol) and 1,8-diazabicyclo[5.4.0]undec-7-ene (103 µL, 690 µmol). The reaction mixture was magnetically stirred and heated via microwave irradiation for 15 minutes at 170° C. Upon cooling to room temperature, the reaction was concentrated in vacuo and purified using high-pressure liquid chromatography to give N-benzyl-4-(5-morpholino-7-oxo-7H-thieno[3,2-b]pyran-3-yl)benzamide (50).

Synthesis of Pyran Analogs Procedure H

Synthesis of 1-(2-Hydroxybiphenyl-3-yl)-3-(tetrahydro-2H-pyran-4-yl)propane-1,3-dione

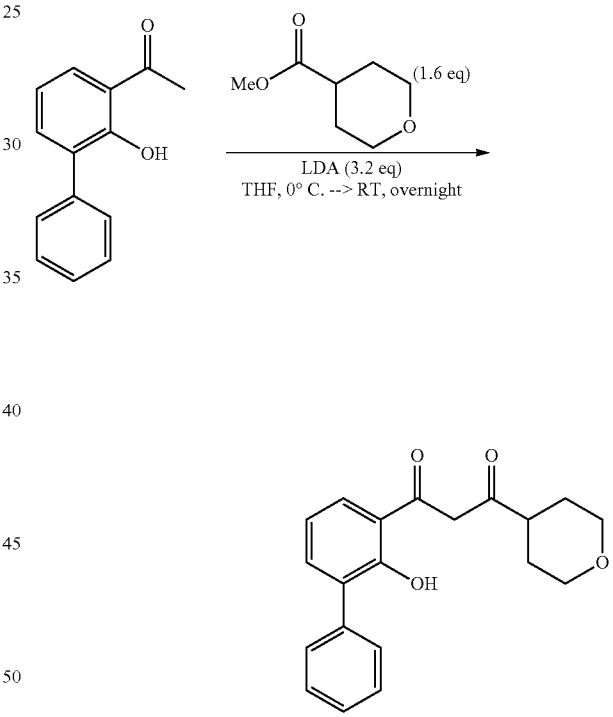

An oven-dried 100 mL round-bottom flask was charged with a magnetic stirring bar, tetrahydrofuran (10 mL) and lithium diisopropylamide (2.0M in hexanes, 6.9 mL, 13.8 mmol). The mixture was magnetically stirred and cooled to 0° C. under argon gas. 1-(2-Hydroxybiphenyl-3-yl)ethanone (0.92 g, 4.34 mmol) was added, and the reaction was stirred at 0° C. for 1 hour. A solution of methyl tetrahydro-2H-pyran-4-carboxylate (1.0 g, 6.94 mmol) in tetrahydrofuran (2 mL) was added dropwise over 5 minutes and the reaction was allowed to warm to room temperature overnight. The reaction was quenched by the addition of aqueous 10% hydrochloric acid solution (20 mL) until pH=3. The resulting solution was transferred to a reparatory funnel, diluted with water (80 mL), and extracted three times with dichloromethane (100 mL). The organic layers were combined, dried over magnesium sulfate, filtered, and concentrated in vacuo to give crude 1-(2-hydroxybiphenyl-3-yl)-3-(tetrahydro-2H-pyran-4-yl)propane-1,3-dione as a brown oil. The crude product was used as is without further purification.

Synthesis of 8-Phenyl-2-(tetrahydro-2H-pyran-4-yl)-4H-chromen-4-one (67)

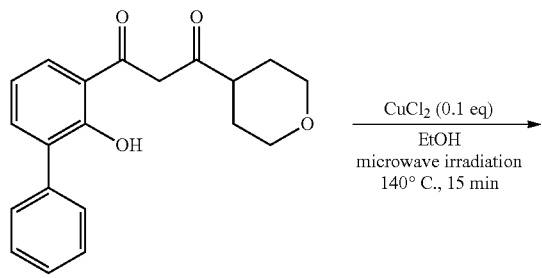

A 5 mL microwave vial was charged with a magnetic stirring bar, crude 1-(2-hydroxybiphenyl-3-yl)-3-(tetrahydro-2H-pyran-4-yl)propane-1,3-dione (320 mg, 1 mmol), ethanol (3 mL), and copper (II) chloride (13 mg, 0.1 mmol). The reaction vial was sealed, the reaction mixture magnetically stirred and heated via microwave irradiation to 140° C. for 10 minutes. The resulting solution was concentrated in vacuo and purified by high-pressure liquid chromatography to give 8-phenyl-2-(tetrahydro-2H-pyran-4-yl)-4H-chromen-4-one (67).

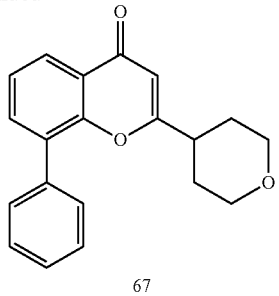

67

Thioketone Synthesis Procedure I

Synthesis of 2-morpholino-8-phenyl-4H-chromene-4-thione (68)

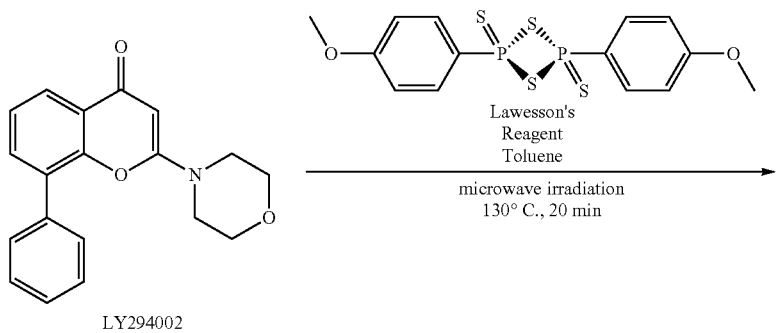

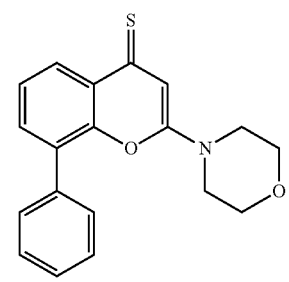

68

A 2 mL conical microwave vial was charged with a magnetic stirring bar, 2-morpholino-8-phenyl-4H-chromen-4-one (LY294002) (150 mg, 488 µmol), Lawesson's reagent (118 mg, 293 µmol), and toluene (2 mL). The reaction mixture was sealed, and the reaction mixture was magnetically stirred and heated via microwave irradiation to 130° C. for 20 minutes. The final mixture was poured onto water (approximately 30 mL), extracted with dichloromethane (3×5 mL), the combined extracts dried over anhydrous magnesium sulfate, filtered and concentrated to dryness. Purification via column chromatography (silica gel; hexanes/ethyl acetate (1:1), then 100% ethyl acetate) afforded pure 2-morpholino-8-phenyl-4H-chromene-4-thione (68) (128 mg, 81% yield).

Carboxylic Acid Synthesis Via Carbonyl Insertion Procedure J

Synthesis of 5-morpholino-7-oxo-7H-thieno[3,2-b]pyran-3-carboxylic acid (70)

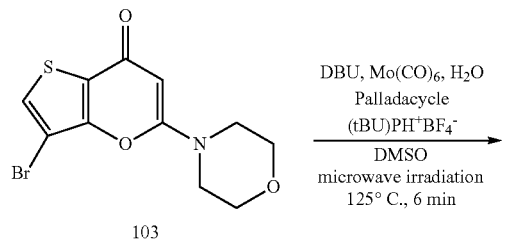

A 2 mL conical microwave vial was charged with a magnetic stirring bar, 3-bromo-5-morpholino-7H-thieno[3,2-b]pyran-7-one (103) (50 mg, 158 µmol), molybdenum hexacarbonyl (42 mg, 158 µmol), trans-di(µ-acetato)bis[o-(di-o-tolyl-phosphino)benzyl]dipalladium (II) (2.0 mg, 2.3 µmol), tri-tert-butylphosphonium tetrafluoroborate (1.4 mg, 4.7 µmol), dimethyl sulfoxide (0.5 mL), water (2.8 µL, 158 µmol), and 1,8-diazabicyclo[5.4.0]undec-7-ene (16 µL, 106 µmol). The reaction mixture was sealed, and the reaction mixture was magnetically stirred and heated via microwave irradiation to 125° C. for 6 minutes to give 5-morpholino-7-oxo-7H-thieno[3,2-b]pyran-3-carboxylic acid (70).

Thiophene Amination Reaction Procedure K

Synthesis of 5-morpholino-3-(piperidin-1-yl)-7H-thieno[3,2-b]pyran-7-one (71)

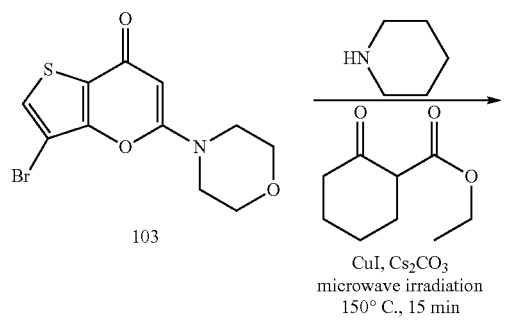

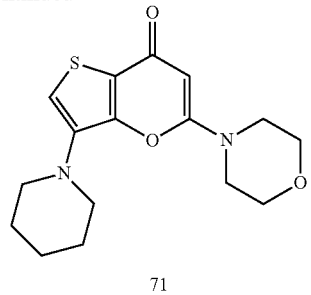

A 0.5 mL microwave vial was charged with a magnetic stirring bar, 3-bromo-5-morpholino-7H-thieno[3,2-b]pyran-7-one (103) (50 mg, 158 µmol), cesium carbonate (103 mg, 316 µmol), copper (I) iodide (3 mg, 31 µmol), ethyl 2-oxo-cyclohexanecarboxylate (10 µL, 63 µmol), and piperidine (200 µL). The reaction mixture was sealed, and the reaction mixture was magnetically stirred and heated via microwave irradiation to 150° C. for 15 minutes to give 5-morpholino-3-(piperidin-1-yl)-7H-thieno[3,2-b]pyran-7-one (71).

Phenyl Amination Reaction Procedure L

Synthesis of 5-morpholino-3-(4-morpholinophenyl)-7H-thieno[3,2-b]pyran-7-one (72)

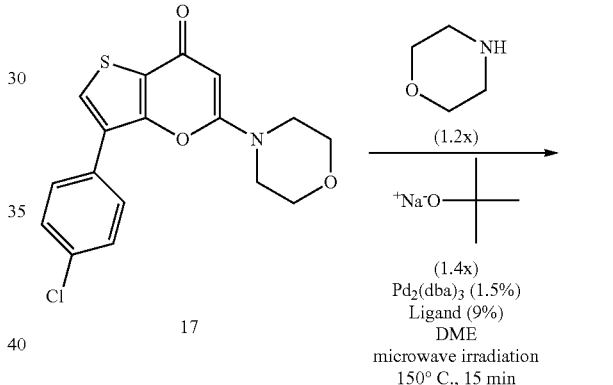

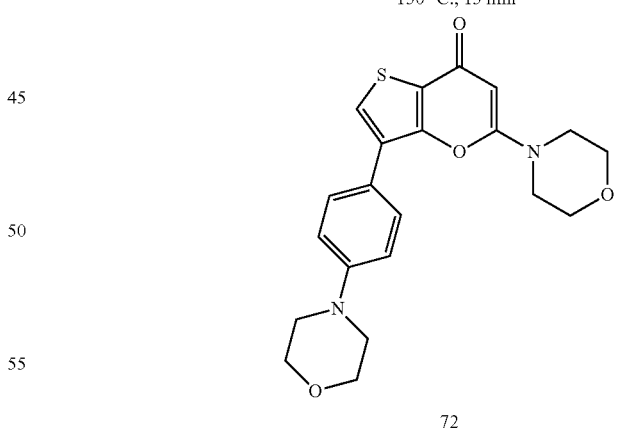

A 2 mL conical microwave vial was charged with a magnetic stirring bar, 3-(4-chlorophenyl)-5-morpholino-7H-thieno[3,2-b]pyran-7-one (17) (80 mg, 230 µmol), sodium tert-butoxide (31 mg, 322 µmol), tris(dibenzylideneacetone)dipalladium(0) (3 mg, 3.5 µmol), 2-dicyclohexylphosphino-2',4',6'-triisopropylbiphenyl (8.8 mg, 21 µmol), dimethoxyethane (0.5 mL), and morpholine (24 µL, 276 µmol). The reaction mixture was sealed, and the reaction mixture was magnetically stirred and heated via microwave irradiation to 150° C. for 15 minutes to give 5-morpholino-3-(4-morpholinophenyl)-7H-thieno[3,2-b]pyran-7-one (72).

Thiophene Carboxylic Ester Synthesis Via Carbonyl Insertion Procedure M

Synthesis of phenyl 5-morpholino-7-oxo-7H-thieno[3,2-b]pyran-3-carboxylate (73)

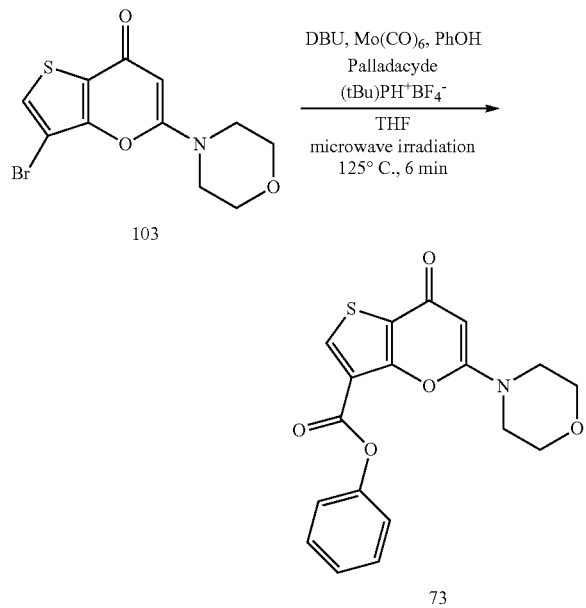 [SMILES: O=c1cc(N2CCOCC2)oc2c(Br)csc12 ; O=C(Oc1ccccc1)c1csc2c(=O)cc(N3CCOCC3)oc12]

A 2 mL conical microwave vial was charged with a magnetic stirring bar, 3-bromo-5-morpholino-7H-thieno[3,2-b]pyran-7-one (103) (50 mg, 158 µmol), phenol (22 mg, 237 µmol), molybdenum hexacarbonyl (42 mg, 158 µmol), trans-di(µ-acetato)bis[o-(di-o-tolyl-phosphino)benzyl]dipalladium (II) (4 mg, 4.7 µmol), tri-tert-butylphosphonium tetrafluoroborate (2.8 mg, 9.5 µmol), tetrahydrofuran (0.5 mL), and 1,8-diazabicyclo[5.4.0]undec-7-ene (71 µL, 474 µmol). The reaction mixture was sealed, and the reaction mixture was magnetically stirred and heated via microwave irradiation to 125° C. for 6 minutes to give phenyl 5-morpholino-7-oxo-7H-thieno[3,2-b]pyran-3-carboxylate (73).

Thiophene Ketone Synthesis Via Carbonyl Insertion Procedure N

Synthesis of 3-acetyl-5-morpholino-7H-thieno[3,2-b]pyran-7-one (74)

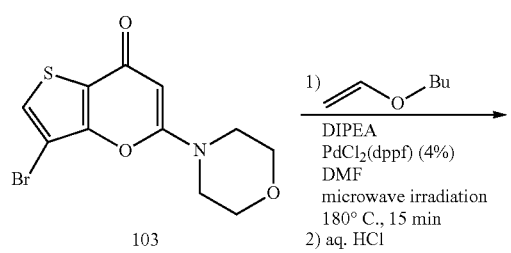

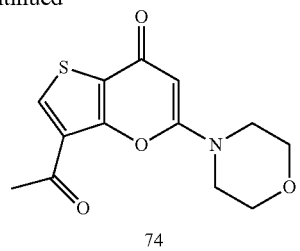

A 2 mL conical microwave vial was charged with a magnetic stirring bar, 3-bromo-5-morpholino-7H-thieno[3,2-b]pyran-7-one (103) (100 mg, 316 µmol), dimethylformamide (0.5 mL), N,N-diisopropylethylamine (165 µL, 949 µmol), butyl vinyl ether (124 µL, 949 µmol), and dichloro[1,1'-bis(diphenylphosphino)ferrocene]palladium(II) dichloromethane adduct (10 mg, 12.6 µmol). The reaction mixture was sealed, and the reaction mixture was magnetically stirred and heated via microwave irradiation to 180° C. for 15 minutes. After cooling to room temperature, the reaction was charged with aqueous hydrochloric acid (1.0 M, 2 mL) and stirred at room temperature for 2 hours to give 3-acetyl-5-morpholino-7H-thieno[3,2-b]pyran-7-one (74).

Phenyl Carboxylic Ester Synthesis Via Carbonyl Insertion Procedure O

Synthesis of butyl 3-(5-morpholino-7-oxo-7H-thieno[3,2-b]pyran-3-yl)benzoate (75)

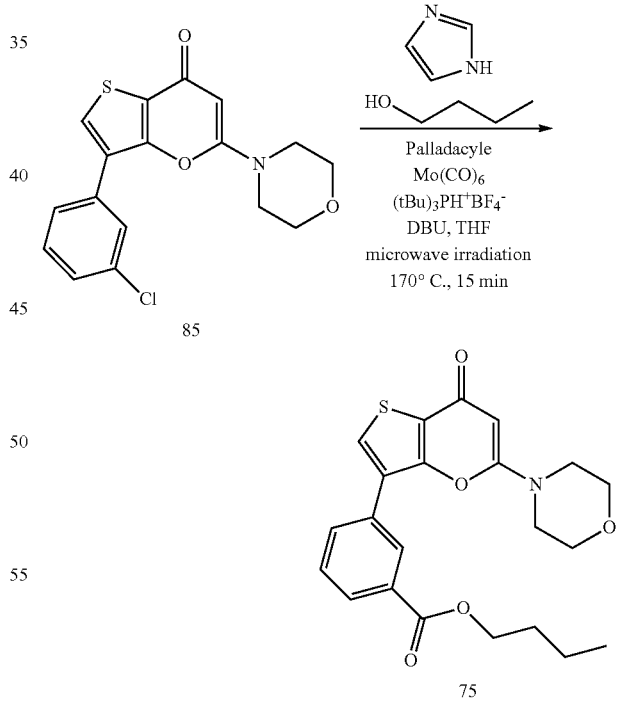

A 2 mL microwave vial was charged with a magnetic stirring bar, 3-(3-chlorophenyl)-5-morpholino-7H-thieno[3,2-b]pyran-7-one (85) (80 mg, 230 µmol), imidazole (47 mg, 690 µmol), molybdenum hexacarbonyl (60 mg, 230 umol), trans-di(t-acetato)bis[o-(di-o-tolyl-phosphino)benzyl]dipalladium (II) (6.5 mg, 6.9 µmol), tri-tert-butylphosphonium tetrafluoroborate (4.0 mg, 13.9 µmol), tetrahydrofuran (500 µL), n-butanol (63 µL, 690 µmol), and 1,8-diazabicyclo[5.4.0]undec-7-ene (103 µL, 690 µmol). The vial was immediately sealed, and the reaction mixture was magnetically stirred and heated via microwave irradiation to 170° C. for 15 minutes in a microwave reactor to give butyl 3-(5-morpholino-7-oxo-7H-thieno[3,2-b]pyran-3-yl)benzoate (75).

Selective Thiophene Carbon-Carbon Coupling Reaction Procedure P

Synthesis of 3-bromo-5-morpholino-2-phenyl-7H-thieno[3,2-b]pyran-7-one (76)

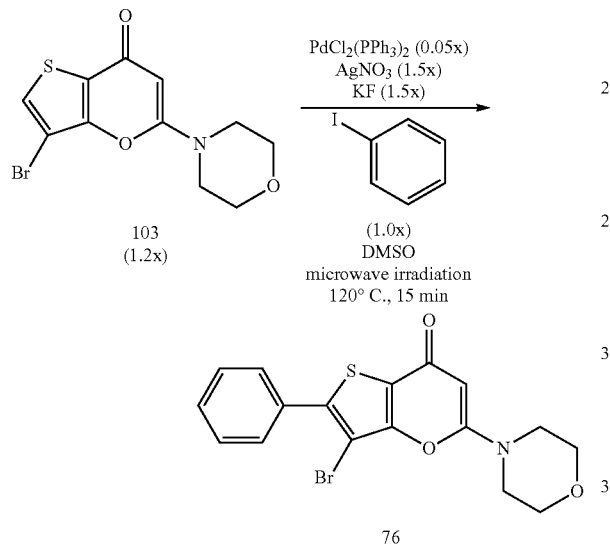

A 2 mL conical microwave vial was charged with a magnetic stirring bar, 3-bromo-5-morpholino-7H-thieno[3,2-b]pyran-7-one (103) (50 mg, 158 µmol), phenyl iodide (27 mg, 132 µmol), potassium fluoride (11.5 mg, 198 µmol), silver nitrate (34 mg, 198 µmol), anhydrous dimethyl sulfoxide (1 mL), and dichlorobis(triphenylphosphine)palladium (II) (4.6 mg, 6.6 µmol). The reaction mixture was sealed, and the reaction mixture was magnetically stirred and heated under microwave irradiation to 120° C. for 15 minutes to give 3-bromo-5-morpholino-2-phenyl-7H-thieno[3,2-b]pyran-7-one (76).

Bis(pinacolato)diboron-mediated Carbon-Carbon Coupling Reaction Procedure R

Synthesis of 2-morpholinoethyl 4-iodobenzoate

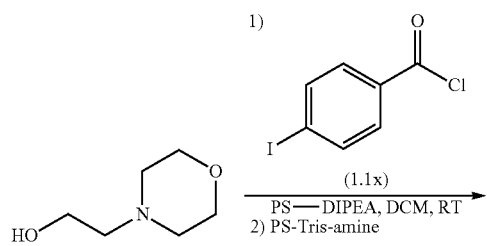

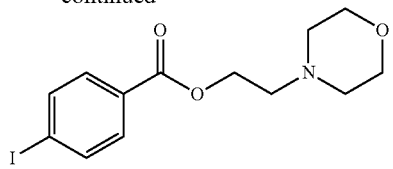

A 8 mL vial was charged with 2-morpholinoethanol (200 µL, 1.63 mmol), dichloromethane (5 mL), polystyrene-linked diisopropylamine (4.90 mmol), and 4-iodobenzoyl chloride (479 mg, 1.80 mmol), and the reaction mixture was shaken at room temperature. After 16 hours, the reaction mixture was charged with polystyrene-linked tris(2-aminoethyl)-amine (1.63 mmol), and shaken at room temperature for 2 hours. The reaction was filtered, and the resin was washed with dichloromethane (3×10 mL), tetrahydrofuran (2×10 mL), and diethyl ether (2×10 mL). The combined filtrates were concentrated in vacuo to give 2-morpholinoethyl 4-iodobenzoate (434 mg, 1.19 mmol) as a white solid.

Synthesis of 2-morpholinoethyl 4-(5-morpholino-7-oxo-7H-thieno[3,2-b]pyran-3-yl)benzoate (77)

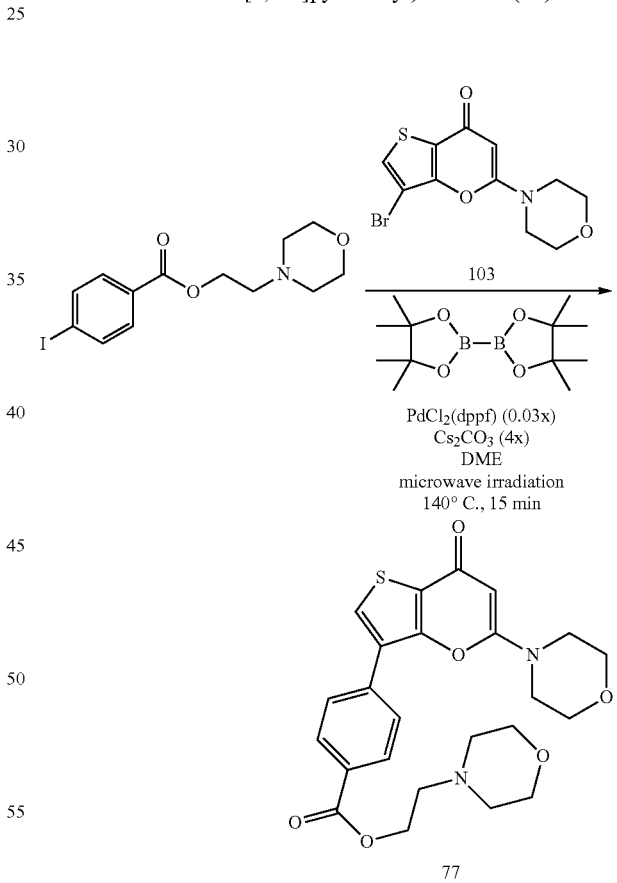

A 2 mL microwave vial was charged with a magnetic stirring bar, 2-morpholinoethyl 4-iodobenzoate (90 mg, 249 µmol), 3-bromo-5-morpholino-7H-thieno[3,2-b]pyran-7-one (103) (79 mg, 249 µmol), bis(pinacolato)diboron (70 mg, 274 µmol), cesium carbonate (325 mg, 997 µmol), dichloro[1,1'-bis(diphenylphosphino)ferrocene]palladium (II) dichloromethane adduct (6 mg, 7 µmol), and 1,2-dimethoxyethane (1 mL). The reaction mixture was sealed, and the reaction mixture was magnetically stirred and heated under microwave irradiation to 140° C. for minutes to give 2-morpholinoethyl 4-(5-morpholino-7-oxo-7H-thieno[3,2-b]pyran-3-yl)benzoate (77).

Conjugates: Chloro Pyrillum Procedure S

Synthesis of 4-chloro-2-morpholino-8-phenylchromenylium chloride (78)

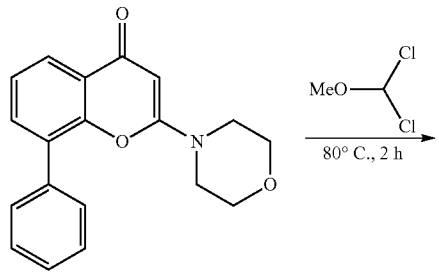

LY294002

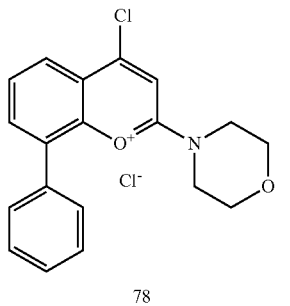

78

A solution of 2-morpholino-8-phenyl-4H-chromen-4-one (LY294002) (1.50 g, 4.93 mmol) and dichloromethyl methyl ether (15 mL) was stirred and heated to 80° C. for 2 hours under argon. The mixture was cooled to room temperature, and then concentrated in vacuo to give 4-chloro-2-morpholino-8-phenylchromenylium chloride (78) (2.06 g, 5.73 mmol).

Conjugates: Pyrillum Ether Procedure T

Synthesis of 4-(3-hydroxypropoxy)-2-morpholino-8-phenylchromenylium chloride (79)

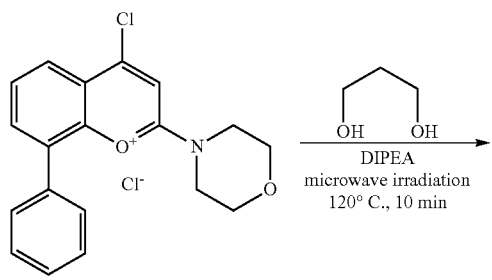

78

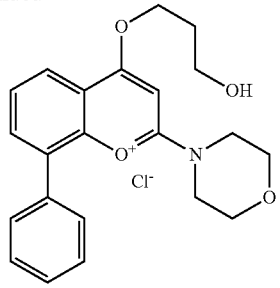

79

A 2 mL microwave vial was charged with a magnetic stirring bar, 4-chloro-2-morpholino-8-phenylchromenylium chloride (78) (50 mg, 138 μmol), 1,3-propanediol (1 mL), and N,N-diisopropylethylamine (48 μL, 276 μmol). The vial was sealed, and the reaction mixture was magnetically stirred and heated under microwave irradiation to 120° C. for 10 minutes in a microwave reactor to give 4-(3-hydroxypropoxy)-2-morpholino-8-phenylchromenylium chloride (79).

Conjugates: Pyrillum Ether Procedure U

Synthesis of 4-ethoxy-2-morpholino-8-phenylchromenylium chloride (80)

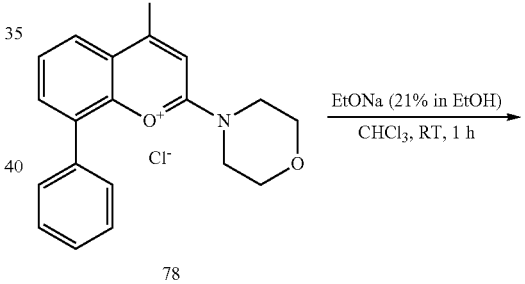

78

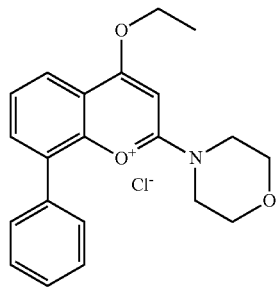

80

A vial was charged with a magnetic stirring bar, 4-chloro-2-morpholino-8-phenylchromenylium chloride (78) (50 mg, 138 μmol), chloroform (1.0 mL), and a solution of sodium ethoxide in ethanol (21%, 108 μL, 290 μmol). The mixture was magnetically stirred at room temperature for 1 hour to give 4-ethoxy-2-morpholino-8-phenylchromenylium chloride (80).

Conjugates: Pyrillum Ether Procedure V

Synthesis of 7-((4-tert-Butoxy-4-oxobutanoyloxy) methoxy)-3-(2,3-dihydrobenzo[b][1,4]dioxin-6-yl)-5-morpholinothieno[3,2-b]pyran-4-ium iodide (81)

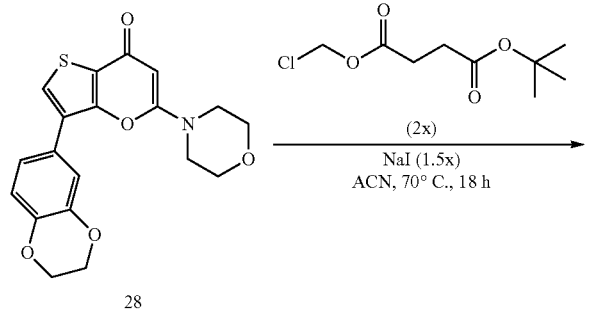

A 10 mL vial was charged with a magnetic stirring bar, tert-butyl chloromethyl succinate (24 mg, 0.107 mmol), acetonitrile (2 mL), 3-(2,3-dihydrobenzo[b][1,4]dioxin-6-yl)-5-morpholino-7H-thieno[3,2-b]pyran-7-one (28) (20 mg, 0.054 mmol) and sodium iodide (12 mg, 0.081 mmol). The reaction mixture was magnetically stirred for 18 hours at 70° C. to give 7-((4-tert-butoxy-4-oxobutanoyloxy) methoxy)-3-(2,3-dihydrobenzo[b][1,4]dioxin-6-yl)-5-morpholinothieno[3,2-b]pyran-4-ium iodide (81).

Conjugates: Pyrillum Acid Chloride Procedure W

Synthesis of 7-((4-chloro-4-oxobutanoyloxy) methoxy)-3-(2,3-dihydrobenzo[b][1,4]dioxin-6-yl)-5-morpholinothieno[3,2-b]pyran-4-ium chloride (82)

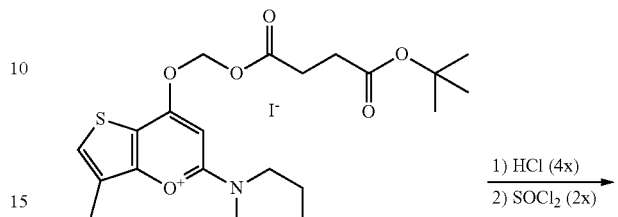

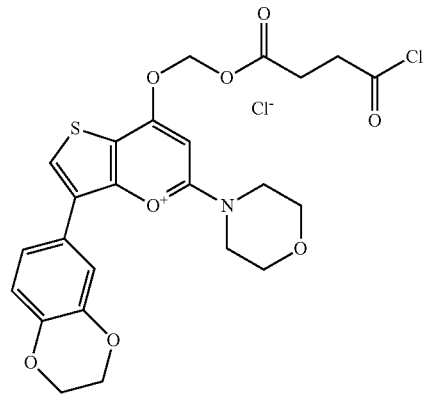

A vial was charged with a magnetic stirring bar, 7-((4-tert-butoxy-4-oxobutanoyloxy)methoxy)-3-(2,3-dihydrobenzo[b][1,4]dioxin-6-yl)-5-morpholinothieno[3,2-b] pyran-4-ium iodide (81) (1.02 g, 1.49 mmol), dichloromethane (4.7 mL) and hydrochloric acid (4 M in dioxane, 1.49 mL, 5.95 mmol). The solution was magnetically stirred at room temperature for 30 minutes. The reaction was charged with thionyl chloride (1.63 mL, 2.98 mmol) and stirred at room temperature overnight. The reaction solution was concentrated in vacuo to give 7-((4-chloro-4-oxobutanoyloxy)methoxy)-3-(2,3-dihydrobenzo [b][1,4]dioxin-6-yl)-5-morpholinothieno[3,2-b]pyran-4-ium chloride (82) (1.12 g, 2.01 mmol) as a crunchy yellow solid.

Conjugates: Pyrillum Protected RGDS Procedure X

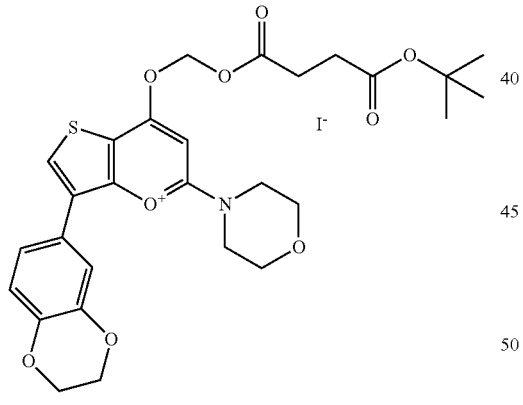

Synthesis of 7-((8S,14S,17S)-14-(2-tert-butoxy-2-oxoethyl)-17-(tert-butoxymethyl)-20,20-dimethyl-3,6,9,12,15,18-hexaoxo-8-(3-(3-(2,2,4,6,7-pentamethyl-2,3-dihydrobenzo furan-5-ylsulfonyl)guanidino)propyl)-2,19-dioxa-7,10,13,16-tetraazahenicosyloxy)-3-(2,3-dihydrobenzo[b][1,4]dioxin-6-yl)-5-morpholinothieno[3,2-b]pyran-4-ium chloride (83)

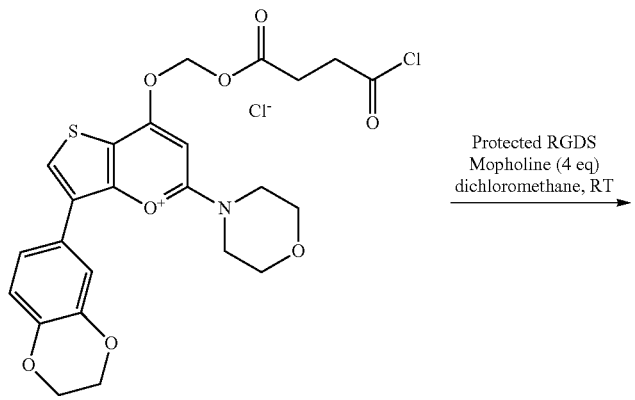

82

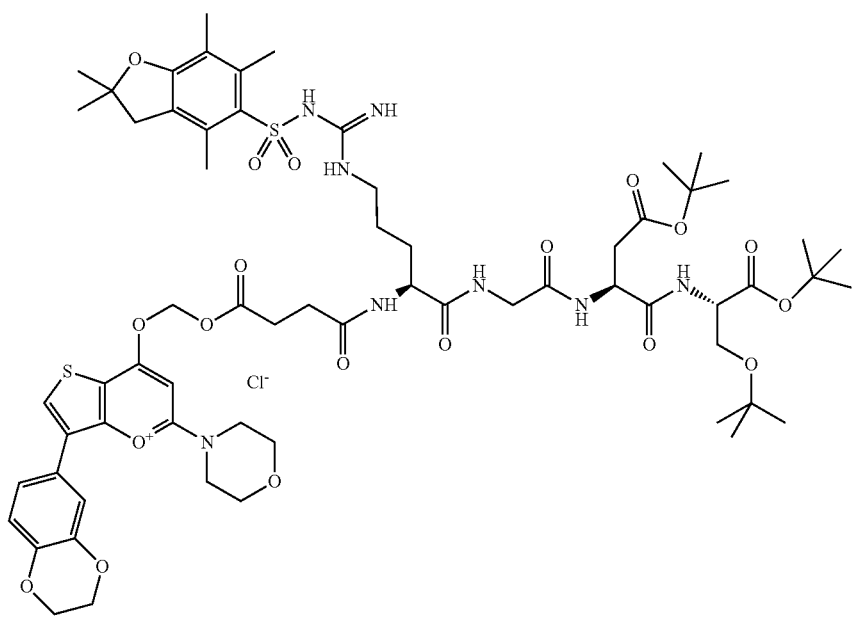

83

A vial was charged with a magnetic stirring bar, H-Arg(Pbf)-Gly-Asp(O'Bu)-Ser('Bu)-O'Bu (854 mg, 1.00 mmol), dichloromethane (10 mL), and N-methylmorpholine (340 µL, 3.09 mmol). The mixture was cooled to 0° C. under magnetic stirring and then charged with 7-((4-chloro-4-oxobutanoyloxy)methoxy)-3-(2,3-dihydrobenzo[b][1,4]dioxin-6-yl)-5-morpholinothieno[3,2-b]pyran-4-ium chloride (82) (500 mg, 0.77 mmol). The reaction solution was allowed to warm to room temperature and stirred for 1 hour. The reaction solution was diluted with dichloromethane (50 mL), washed three times with dilute aqueous citric acid (0.1 M, 50 mL), washed three times with dilute aqueous sodium bicarbonate solution (5%, 50 mL), washed twice with brine solution, dried over magnesium sulfate, filtered, and concentrated in vacuo to give 7-((8S,14S,17S)-14-(2-tert-butoxy-2-oxoethyl)-17-(tert-butoxymethyl)-20,20-dimethyl-3,6,9,12,15,18-hexaoxo-8-(3-(3-(2,2,4,6,7-pentamethyl-2,3-dihydrobenzo furan-5-ylsulfonyl)guanidino)propyl)-2,19-dioxa-7,10,13,16-tetraazahenicosyloxy)-3-(2,3-dihydrobenzo[b][1,4]dioxin-6-yl)-5-morpholinothieno[3,2-b]pyran-4-ium chloride (83) (1.05 g, 0.72 mmol) as a yellow solid.

Conjugates: Pyrillum Unprotected RGDS Procedure Y

Synthesis of 7-((8S,14S,17S)-17-carboxy-14-(carboxymethyl)-8-(3-guanidinopropyl)-18-hydroxy-3,6,9,12,15-pentaoxo-2-oxa-7,10,13,16-tetraazaoctadecyloxy)-3-(2,3-dihydrobenzo[b][1,4]dioxin-6-yl)-5-morpholinothieno[3,2-b]pyran-4-ium trifluoroacetate (84)

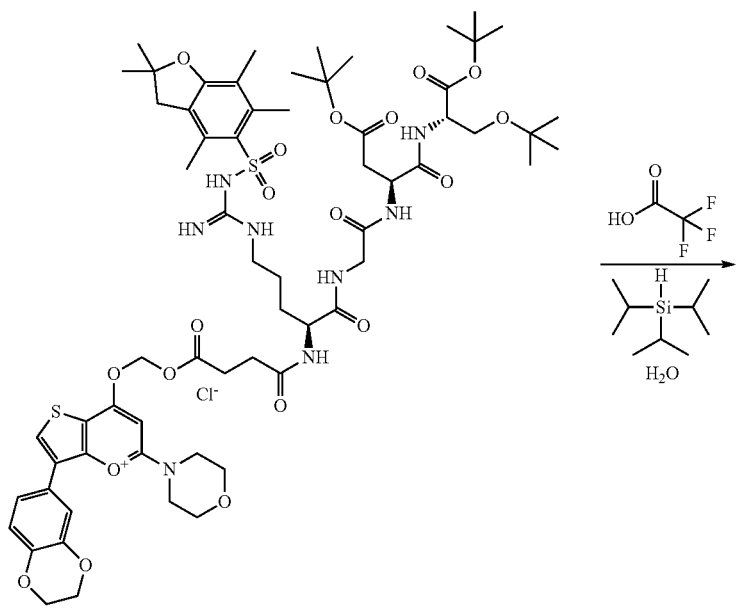

83

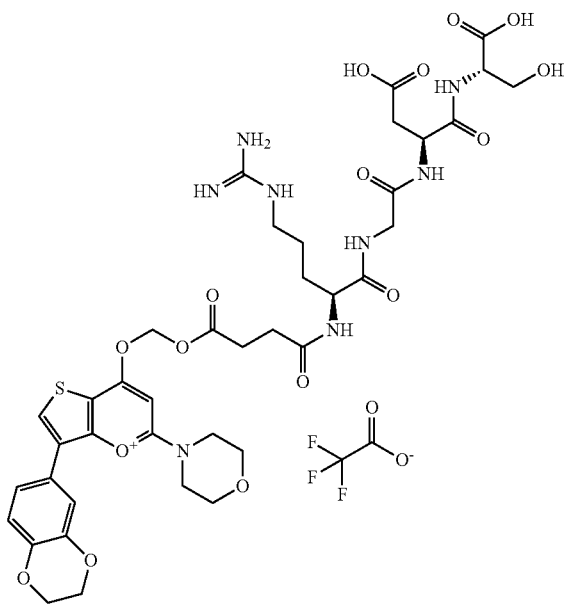

84

A vial was charged with a magnetic stirring bar, 7-((8S,14S,17S)-14-(2-tert-butoxy-2-oxoethyl)-17-(tert-butoxymethyl)-20,20-dimethyl-3,6,9,12,15,18-hexaoxo-8-(3-(3-(2,2,4,6,7-pentamethyl-2,3-dihydrobenzo furan-5-ylsulfonyl)guanidino)propyl)-2,19-dioxa-7,10,13,16-tetraazahenicosyloxy)-3-(2,3-dihydrobenzo[b][1,4]dioxin-6-yl)-5-morpholinothieno[3,2-b]pyran-4-ium chloride (83) (0.500 g, 0.364 mmol) and a solution of water (20 μL, 1.09 mmol) and triisopropyl silane (224 μL, 1.09 mmol) in trifluoroacetic acid (5.19 mL, 70 mmol). The reaction solution was magnetically stirred at room temperature. After 3 hours, the reaction solution was charged with ethyl ether (20 mL). The resulting precipitate was filtered, and purified by high-pressure liquid chromatography to give 7-((8S,14S,17S)-17-carboxy-14-(carboxymethyl)-8-(3-guanidinopropyl)-18-hydroxy-3,6,9,12,15-pentaoxo-2-oxa-7,10,13,16-tetraazaoctadecyloxy)-3-(2,3-dihydrobenzo[b][1,4]dioxin-6-yl)-5-morpholinothieno[3,2-b]pyran-4-ium trifluoroacetate (84) as a white solid.

tert-Butoxycarbonyl (Boc) deprotection Procedure Z

Synthesis of 5-morpholino-3-(1H-pyrrol-2-yl)-7H-thieno[3,2-b]pyran-7-one (97)

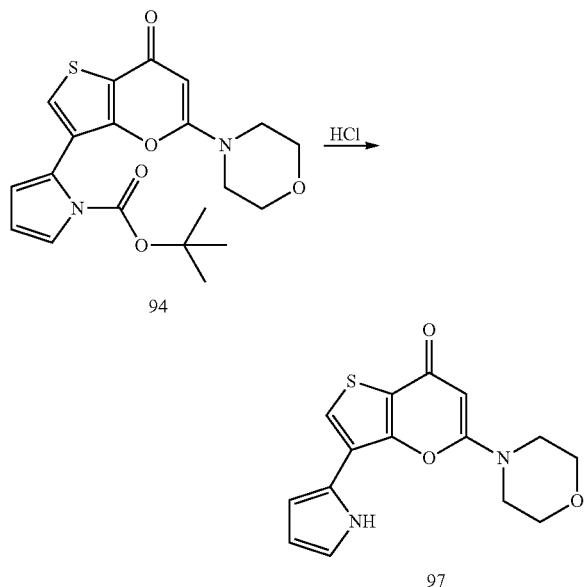

A 20 mL vial was charged with a magnetic stirring bar, tert-butyl 2-(5-morpholino-7-oxo-7H-thieno[3,2-b]pyran-3-yl)-1H-pyrrole-1-carboxylate (94) (50 mg, 124 μmol), and hydrochloric acid (4.0 M in dioxane, 10 mL). The reaction mixture was magnetically stirred overnight at room temperature, concentrated in vacuo, and purified via reverse phase high-pressure liquid chromatography to give 5-morpholino-3-(1H-pyrrol-2-yl)-7H-thieno[3,2-b]pyran-7-one (97).

I. Biological Examples

EXAMPLE A

Effect of Test Compounds on pAKT Status in Prostate Cancer Cells (PC3)

PC3 cells were obtained from the American Type Culture Collection (ATCC, Manassas, Va., Cat.# CRL-1435). Two million cells from the prostate cancer line PC3 were placed into 6 cm culture dishes and allowed to grow in complete RPMI 1640 media (Invitrogen, Calsbad, Calif., Cat.# 22400-105) with 10% fetal bovine serum (Invitrogen, Calsbad, Calif., Cat.# 10438-026). After this time period the cells were serum starved for 5 hours followed by application of the test compound. Test compound was added as a DMSO (dimethyl sulfoxide) solution such that the final DMSO concentration in the cell media was less than or equal to 0.2% by volume After 30 minutes of exposure the growth factor stimulant, human IGF-1 (PeproTech, Inc., Rocky Hill, N.J., Cat.# 100-11), was added to a final concentration of 0.1 μg/ml in each well. After 30 minutes of IGF-1 exposure, cells were removed from the media and cell lysates were prepared using RIPA Lysis buffer (Upstate, Lake Placid, N.Y., Cat.# 20-188), keeping on ice. The pAKT serine 473 level was measured in duplicate samples of the cell lysates using commercially available assays such as the Pathscan® Sandwich ELISA kit for Ser473 pAKT (Cell Signaling, Danvers, Mass., Cat.# 7160). A SpectraMax Plus spectrophotometric plate reader (Molecular Devices, Sunnydale, Calif.) was used to measure the optical density signal for pAKT at 450 nm (OD450 nm). The pAKT OD450 nm readings were normalized by total protein amount in the cell lysates determined by standard methods.

Concentrations of test compounds required to inhibit IGF stimulated pAKT levels to 50% of maximum levels in PC3 cells (termed DM50 for decreased maximum 50%) were calculated by inputting the dose responses in the software package GraphPad Prism4 (GraphPad Software, Inc., San Diego, Calif.).

By these methods a number of compounds of the invention were evaluated and the concentration needed to reduce the detectable pAKT to 50% of the maximal uninhibited signal was calculated. These values (in μMolar units) are listed in Table 8 under the column heading PC3 pAKT IC50 (μMolar).

EXAMPLE B

Effect of Test Compounds on Prostate Cancer Cell (PC3) Proliferation

PC3 cells were obtained from the American Type Culture Collection (ATCC, Manassas, Va., Cat.# CRL-1435) Two thousand cells from the prostate cancer line PC3 were placed in 50 μL of complete RPMI 1640 media (Invitrogen, Calsbad, Calif., Cat.# 22400-105) with 10% fetal bovine serum (Invitrogen, Carlsbad, Calif., Cat.# 10438-026) into each well of 96 well cell culture plates in a hexaplicate sampling pattern. A 50 μL aliquot of test compound (prepared from stock test compounds in DMSO diluted into media) was added to the appropriate well such that the final concentrations of test compound were 200, 40, 8, 1.6, 0.32, 0.064, 0.0128, 0.00256, and 0 μM and the final DMSO concentration was less than or equal to 0.2%.

The plates were incubated for 72 hours 37° C. in an atmosphere of 5% $CO_2$. At the end of this time a 10 μL aliquot of WST solution (Roche Applied Science, Mannheim, Germany) was added into each of the wells. Cells were exposed to the WST solution for 4 hours. A SpectraMax Plus spectrophotometric plate reader (Molecular Devices, Sunnydale, Calif.) was then used to measure the optical density at 450 nm (OD450 nm). Sigmoidal curves were drawn for the dose responses and IC50 values were calculated using the software package GraphPad Prism4 (GraphPad Software, Inc., San Diego, Calif.).

By these methods a number of compounds of the invention were evaluated and the concentration needed to reduce the prostate cancer cell (PC3) proliferation by 50% was calculated. These values (in μMolar units) are listed in Table 8 under the column heading IC50 PC3 Proliferation (μMolar).

EXAMPLE C

Comparison of IC50 Values for LY294002 and Cpd 6

IC50 values for inhibition of PI-3 kinase activity and PC3 cell proliferation were determined for LY294002 and Cpd 6. LY294002 is available commercially (CellSignaling Technology, Cat. No. 9901) and is well described in the literature as a pan-PI-3 kinase inhibitor. IC50 values for LY294002 were obtained and are listed in Table 1 below. Likewise, IC50 values for Cpd 6 were also obtained. The fold improvement in the IC50 values (i.e., increased potency) of Cpd 6 in comparison with LY294002 is calculated and shown in Table 1. For the beta and delta isoforms of PI-3 kinase the increased potency was approximately 2-fold and 4-fold respectively. Additionally, mTOR is a clinically validated target in cancer treatments and Cpd 6 demonstrated almost 2-fold improvement in inhibiting mTOR versus LY294002. Evaluation of the ability of Cpd 6 to block the PI3K pathway and decrease the pAKT activation in PC3 cells by 50% versus LY294002 demonstrated over a 2-fold improvement in activity.

Lastly, the 1050 for inhibition of prostate cancer cell proliferation (PC3 cell line run as described in example A) was determined and is listed in the last row of Table 1. The data clearly shows an almost 2-fold improvement in the cellular activity of Cpd 6 versus LY294002.

TABLE 1

Comparison of IC50 values (nM) for LY294002 versus Cpd 6

| Category | Enzyme | LY294002 | Cpd 6 | Fold Improvement* |
|---|---|---|---|---|
| PI3K Class 1A | p110-alpha | 356 | 297 | 1.2 |
| PI3K Class 1A | p110-beta | 736 | 378 | 1.9 |
| PI3K Class 1A | p110-delta | 3224 | 784 | 4.1 |
| PI3K Class 1B | p110-gamma | 1775 | 1570 | 1.1 |
| PI3K Super Family Enzyme | mTOR | 1060 | 610 | 1.7 |
| Pathway Inhibition | pAKT | 1.3 | 0.55 | 2.4 |
| Cell Proliferation | PC3 IC50 Proliferation | 7,500-12,100 | 4,100 | 1.8-3.0 |

*the value for LY294002 is divided by the value obtained for Cpd 6
Several other compounds of the invention had IC50 values against the panel of enzymes in Table 1 in the range of 1-10 μM, while others had IC50 values of less than 1 μM (data not shown).

EXAMPLE D

Therapeutic Effect of Cpd 9 in a Renal Cell Carcinoma Xenograft Mouse Model

To determine if Cpd 9 has anti-tumor effects, an in vivo study was conducted in a 786-0 renal cell carcinoma xenograft model. 786-0 cells ($2 \times 10^6$) were inoculated subcutaneously into nude mice in the flank area and tumor growth was monitored with calipers via external measurements. Tumor volume was calculated using the formula volume= (length×width$^2$)/2. When the average tumor volume reached 400 mm$^3$, mice were randomly divided into 2 groups and treated with either DMSO (control) or Cpd 9 (25 mg/kg, ip) three times weekly (M, W, F) for two weeks. This renal cell carcinoma (RCC) xenograft experiment with nude mice showed that administration of Cpd 9 (25 mg/kg, ip, 3×/wk) after about two weeks resulted in 93% tumor growth reduction (p<0.05) compared to the control group. No significant body weight change or other abnormalities were observed.

EXAMPLE E

Therapeutic Effect of Cpd 28 in a Renal Cell Carcinoma Xenograft Mouse Model

To determine if Cpd 28 has anti-tumor effects, an in vivo study was conducted in a 786-0 renal cell carcinoma xenograft model. 786-0 cells ($2 \times 10^6$) were inoculated subcutaneously into nude mice in the flank area and tumor growth was monitored with calipers via external measurements. Tumor volume was calculated using the formula volume= (length×width$^2$)/2. Treatment was started when tumors reached an average volume of 300 mm$^3$. Mice were randomized into groups of 5 animals each and were given intraperitoneal administration of either LY294002 (25 mg/kg) or Cpd 28 (25 mg/kg or 50 mg/kg) at a frequency of 3 times weekly for 4 weeks. DMSO was used as control since this was the vehicle the compounds were dissolved in. Tumor size was monitored twice weekly and body weight was monitored once weekly. Means and standard deviations were calculated and the Student t test method was used for statistical comparisons. In the same xenograft model, administration of LY294002 and Cpd 28 at the same dosage (25 mg/kg, ip, 3×/wk) showed that Cpd 28 has a stronger inhibitory tumor growth effect than LY294002 (compared to control) (70% vs. 54% inhibition, respectively) while administration of Cpd 28 at twice the dosage and same administration routine (50 mg/kg, ip, 3×/wk) shows a more potent tumor growth inhibition (compared to control) (81%) also with no significant body weight change or other abnormalities noted.

EXAMPLE F

Apoptotic Effects of Cpd 9 and Cpd 28 in Renal Cell Carcinoma (786-O)

In order to evaluate the mechanism of action of these compounds, 786-0 cell cultures were treated with Cpd 9 or Cpd 28 at different concentrations overnight and then analyzed for apoptotic induction. The cells were stained using standard methods with Annexin V and/or Propedium iodine (PI) at room temperature for 15 minutes. Apoptotic cells at early (Annexin V positive) or late stage (both Annexin V and PI positive) were detected by Flow Cytometry. The results are shown in Table 2 below and demonstrate a dose dependant increase in apoptosis after exposure to either Cpd 9 or Cpd 28 under these conditions:

TABLE 2

Dose dependent increase in apoptosis of cancer cells.

| Apoptotic cells | Un- treated control | Actino- mycin D (200 ng/mL) | Cpd 9 (5 μM) | Cpd 9 (10 μM) | Cpd 28 (5 μM) | Cpd 28 (10 μM) |
|---|---|---|---|---|---|---|
| Early stage apoptotic | 3.97 | 16.93 | 7.76 | 8.31 | 10.4 | 16.45 |
| Late stage apoptotic | 7.35 | 12.63 | 10.5 | 11.62 | 11.56 | 15.43 |
| Total Apoptotic Cells | 11.32 | 29.56 | 18.26 | 19.93 | 21.96 | 31.88 |

EXAMPLE G

Cell Proliferation Effects of Cpd 28 Across a Broad Spectrum of Cancer Cell Lines All cell lines were obtained from ATCC and cultured and plated according to ATCC recommendations. Cells were cultured in complete culture media containing 10% heat-inactivated fetal bovine serum (FBS, Mediatech, Inc.). For adherent cell lines, once cells reached 70% confluency, they were trypsinized and resuspended in phenol red free RPMI media (Mediatech, Inc.) plus 10% heat-inactivated FBS (assay buffer) and 100 μL aliquots were plated into each well of 96-well microtiter plates at a final density of 1,000-2,000 cells/well. Cells were incubated overnight at 37° C. in 5% $CO_2$, and treated with test compounds on the next day. For suspension cell lines, cells were resuspended in assay buffer, plated into 96-well microtiter plates at a density of $10^4$-$10^5$ cells/well/100 μL, and treatment was started on the same day. Cells were treated with vehicle (DMSO) and test compounds for 72 hours at concentration of 100, 70, 40, 20, 10, 5, 2.5, 1.25, 0.5 and 0.2 μM in four replicates at 37° C. in 5% $CO_2$. Following incubation, viable cells were quantified by the MTS assay (MTS is: 3-[4,5-dimethylthiazol-2-yl]-5-(3-carboxymethoxyphenyl)-2-(4-sulfophenyl)-2H-tetrazolium (Promega (Madison, Wis., USA). At the end of a 72-hour treatment, 100 μL of assay buffer was removed and cells were incubated with 20 μL of mixture of MTS and phenazine methosulfate (TCI America) at 37° C. in 5% $CO_2$ for 3 hours. Absorbance values (OD) were measured using a Dynex Opsys MR plate reader at a single wavelength of 490 nm. Data were analyzed by computer-assisted nonlinear regression to fit the data using GraphPad Prism (GraphPad software, San Diego, Calif.). IC50 is the concentration of drug that inhibits cell growth by 50% of the vehicle. Results were expressed as means and are listed in table 3 below.

With the exception of Panc-1 all IC50 values were single digit micromolar or less. This level of potency was true even for cell lines containing KRAS mutations (HCT116-colon, A549 lung, BXPC3 pancreatic and RPMI8226 myeloma cell lines). Colorectal cancer patients with KRAS mutations have been identified as less likely to respond to EGFR inhibitors as reported at ASCO 2008 annual meeting thus representing an unmet medical need. Likewise, Cpd 28 has equal potency on breast cancer cell lines MCF-7 and MDA-MB-468 even though the latter cell line represents "triple negative" breast cancer. This is a subset of breast cancer that are found to be negative for Her-2, progesterone, and estrogen receptors. This set of breast cancer patients currently have few good treatment options and represents an unmet medical need.

TABLE 3

IC50 values for Cpd 28 against various cancer cell types.

| Cell Line (Cancer Type) | IC50 values of Cpd 28 (μM) |
| --- | --- |
| A549 (Lung) | 2.54 |
| H1299 (Lung) | 2.43 |
| BXPC3 (Pancreas) | 3.35 |
| Panc-1 (Pancreas) | 18.42 |
| PC3 (Prostate) | 1.22 |
| DU145 (Prostate) | 2.07 |
| HT29 (Colon) | 2.40 |
| Hela (Colon) | 2.10 |
| HCT116 (Colon) | 2.20 |
| MDA-MB468 (Breast) | 2.71 |
| MCF7 (Breast) | 2.27 |
| U87MG (Brain) | 1.92 |
| OVCAR3 (Ovary) | 1.24 |
| 786-O (Renal) | 2.82 |
| SKMEL2 (Melanoma) | 5.20 |
| RPMI8226 (Myeloma) | 0.73 |
| HL60 (AML) | 3.06 |
| K562 (CML) | 3.20 |
| HUVEC (Endothelial-noncancer) | 1.23 |

EXAMPLE H

Blockage of Signal Transduction by Cpd 28 and Cpd 25 in Cancer Cell Lines

Angiogenesis is a well-described mechanism of cancer progression and several agents are clinically useful due to their ability to inhibit this process in cancer patients. VEGF is one of the most studied angiogenic factors. VEGF is secreted by cancer cells in response to hypoxia leading to nearby endothelial cell surface receptor binding which stimulates the endothelial response resulting in new blood vessels. PI-3 kinase (PI3K) has been shown to be integral to the angiogenic process where inhibition of PI3K blocks hypoxia-induced VEGF production in cancer cells as well as the VEGF-mediated stimulation of endothelial cells. The latter could be due to the ability of PI3K inhibitors to prevent cell-surface receptor mediated activation of AKT to pAKT and thus block downstream signaling elements. Bv8 is a protein that has recently been determined to play a role in angiogenesis and anti-Bv8 antibodies have been shown to inhibit tumor growth in mouse studies (Nature 2007, 450, 825-831). Additionally, recent work (Cancer Res. 2008, 68, 5501-5504 and references therein) has indicated that Bv8 may play a role in resistance of tumors to treatment with antivascular endothelial growth factor treatment such as antibodies to VEGF. Because of this evolving interest in Bv8 we sought to understand the ability of the novel PI3K inhibitors of the invention to block Bv8 signaling down the AKT pathway in comparison to the angiogenic ligand VEGF- and IGF-pathway activation.

To evaluate the effect of Cpd 28 and Cpd 25 on AKT Ser473 phosphorylation, two million cells from the prostate cancer line PC3 and renal carcinoma cell line (786-O) were placed into 6 cm culture dishes and allowed to grow in complete media followed by 5 hours serum starvation followed by the application of test compound to a final concentration of 0, 0.1, 0.5, and 2 μM for 30 minutes. This was followed by the addition of IGF, VEGF and Bv8 to 0.1 μg/mL, 0.1 μg/mL and 2.5 μg/mL respectively for another 30 minutes before harvesting the cells and making cell lysates with RIPA buffer keeping on ice. pAKT levels were measured in duplicate samples with Cell Signaling's Ser473 pAKT ELISA kit. Optical density plate readings of pAKT levels were made at 450 nm (OD450 nm) and were normalized by total protein amount of the cell lysates. The dose of compound at which pAKT levels are reduced to 50% of the non-treatment level was calculated using GraphPad Prism4 software and is listed in Tables 4 and 5 below.

TABLE 4

Concentrations (μM) of Cpd 28 and Cpd 25 Required to Inhibit pAKT to Half-maximal Levels Stimulated by Bv8, VEGF and IGF in PC3 (prostate cancer) Cell Line

| | Compound | |
| --- | --- | --- |
| Stimulant | Cpd 28 | Cpd 25 |
| PBS | 0.229 | 0.564 |
| Bv8 | 0.1164 | 0.9406 |
| VEGF | 0.1523 | 0.3317 |
| IGF | 0.888 | 2.117 |

TABLE 5

Concentrations (μM) of Cpd 28 and Cpd 25 Required to Inhibit pAKT to Half-maximal Levels Stimulated by Bv8, VEGF and IGF in the renal cell carcinoma (786-O) Cell Line

| | Compound | |
| --- | --- | --- |
| Stimulant | Cpd 28 | Cpd 25 |
| PBS | 0.5407 | 0.9176 |
| Bv8 | 0.3799 | 0.6994 |

TABLE 5-continued

Concentrations (μM) of Cpd 28 and Cpd 25 Required to Inhibit pAKT to Half-maximal Levels Stimulated by Bv8, VEGF and IGF in the renal cell carcinoma (786-O) Cell Line

| Stimulant | Compound | |
|---|---|---|
| | Cpd 28 | Cpd 25 |
| VEGF | 0.3434 | 0.4976 |
| IGF | 2.605 | 4.389 |

The above results indicate that in vitro inhibition of PI3K by Cpd 28 or Cpd 25 can impede the angiogenic stimulants VEGF and Bv8 in their ability to activate AKT in a dose dependant manner in cancer cells.

EXAMPLE I

Effect of Test Compounds on pAKT Status in Various Cancer Cell Lines

Several other cancer cell lines were obtained from ATCC and grown according to the supplier's recommendations and treated with test compounds. DM50 values listed in Table 6 below were obtained by the methods described in Example A:

TABLE 6

Effect of test compounds on DM50 of cancer cells.

| Type of Cancer | Cell Line | DM50 | | |
|---|---|---|---|---|
| | | Cpd 6 | Cpd 9 | Cpd 28 |
| Non-small cell lung cancer | H1299 | 3.192 | 3.070 | 0.886 |
| Breast cancer | BT-474 | 1.245 | 0.906 | 0.307 |
| Renal cell carcinoma | 786-O | 4.166 | 2.662 | 1.367 |

EXAMPLE J

Effect of Test Compounds on Cellular Proliferation in Various Cancer Cell Lines

Several other cancer cell lines were obtained from ATCC and grown according to their recommendations and treated with test compounds to obtain the concentration of test compound that inhibited the cellular proliferation by 50% of no-treatment controls. These IC50 values (μM) are listed in Table 7 below obtained by the methods described in Example B:

TABLE 7

Inhibition of cancer cell proliferation.

| Type of Cancer | Cell Line | IC50 | | |
|---|---|---|---|---|
| | | Cpd 6 | Cpd 9 | Cpd 28 |
| Non-small cell lung cancer | H1299 | 5.024 | 3.040 | 0.951 |
| Breast cancer | BT-474 | 11.62 | 5.911 | 3.775 |
| Renal cell carcinoma | 786-O | 9.53 | 6.238 | 3.321 |

EXAMPLE K

Effect of Test Compounds on Oxidative Stress of Prostate Cancer Cells

LNCaP cells were obtained from the American Type Culture Collection (ATCC, Manassas, Va., Cat.# CRL-1740). 3.5 million cells from the prostate cancer line LNCaP were placed into each of three 10 cm culture dishes and allowed to grow overnight in complete RPMI 1640 media (Invitrogen, Calsbad, Calif., Cat.# 22400-105) with 10% fetal bovine serum (Invitrogen, Calsbad, Calif., Cat.# 10438-026). Test compound was added into the dishes to the concentration of 0 and 20 μM and allowed to incubate at 37° C. in a 5% $CO_2$ atmosphere for 2 and 24 hours. Following this the pH of the cell culture media was adjusted down to 3.5 with 2M HCl. After sitting at 4° C. for 15 minutes, the cell culture media from each culture dishes was applied to each of three C18 reverse phase columns (Biotage ISO-LUTE, Part #220-0020-B, Lot #5223506B2A, www.biotage.com) which were prewashed with 10 mL/column of ethanol followed by 10 mL/column of deionized water. The loaded columns were then washed with 10 mL/column of water, followed by 10 mL/column of 15% ethanol, and finally 10 mL/column hexane. The desired samples were then eluted from the columns by addition of 10 mL/column ethyl acetate. The ethyl acetate was then evaporated to dryness using a rotating evaporator. Each sample was then dissolved in 500 μL of Assay Buffer provided in BioMol's Isoprostane Oxidative Stress Assay Kit A (Cat. # AK150-0001, Lot #3-08010825). Using the kit reagents according to the manufacturer's instructions the oxidative product 8-iso-Prostaglandin F2α was quantitated by ELISA. Also, using reagents from the kit a standard curve of oxidation product (8-iso-Prostaglandin F2α) versus optical density reading at 450 nm. From this curve optical density readings from the test samples were converted to pg/mL of the oxidation marker 8-iso-Prostaglandin F2α. This kit from BioMol is designed to determine the amount of the 8-iso-Prostaglandin F2α produced as a marker for the amount of oxidative stress experienced by the cells.

Using this method Cpd 28 gave OD450 nm readings of 1.01 units at 2 hours and 0.96 units at 24 hours exposure (control=1.36 units) which translates to 18.0 and 21.0 pg/mL of 8-iso-Prostaglandin F2α generated respectively (versus control samples of 1.5 pg/mL). Relative to untreated controls Cpd 28 exposure gave an increase of oxidation marker 8-iso-Prostaglandin F2α of 12-fold at 2 hours and 14-fold at 24 hours in prostate cancer cells (LNCaP). These results indicate that Cpd 28 quickly induces a large increase in oxidative stress in prostate cancer cells.

EXAMPLE L

Effect of Test Compounds in Inhibiting Cancer Stem Cells

A mammosphere cancer stem cell inhibition assay was set up using literature methods (T. M. Phillips et al. *J. Natl. Cancer I.* 2006, 98, 1777-1785, "Mammalian target of rapamycin contributes to the acquired apoptotic resistance of human mesothelioma multicellular spheroids") using a subset of MCF7 breast cancer cells that posses the ability to evade anchorage independent apoptosis. Commercially available MCF7 breast cancer cells were cultured in MEM supplemented with 0.01 mg/mL of bovine insulin and 10% FBS at 37° C. in humidified atmosphere (5% $CO_2$). Floating cells in the 2-day cultures were collected, washed, and resuspended in DMEM-F12 (50:50) supplemented with 0.4% BSA, 5 μg/mL bovine insulin, 20 ng/mL bFGF, and 10 ng/mL EGF. Cells were then passed through a 40 μM sieve to remove any cell clusters and adjusted to a density of 10,000 cells/mL. Approximately 500 cells were plated in quadruplicate in a sterile poly-HEMA-treated 96-well plate. Cells were then treated with either control or test solutions consisting of the kinase inhibitor Lapatinib (1 μM), Cpd 28 (1 or 10 μM), Cpd 55 (1 or 10 μM), The numbers of mammospheres (clusters of cells numbering more than 4 or 5 per cluster) were then counted after 5-7 days.

In one experiment for the control sample (no test agent added) a mean of the quadruplicate measurements yielded 38±4 mammospheres whereas the kinase inhibitor Lapatinib, approved for treating breast cancer, at 1 μM gave 26±2 mammospheres. Cpd 28 at 1 μM or 10 μM yielded 15±2 and 5±1 mammospheres respectively. Cpd 55 at 1 μM or 10 μM yielded 16±2 and 5±1 mammospheres respectively. Thus, Cpd 28 and Cpd 55 at 1 μM gave approximately 60% inhibition of mammosphere production versus control whereas Lapatinib at this same concentration only gave 33% inhibition of mammosphere production. At the higher concentration of 10 μM Cpd 28 and Cpd 55 gave approximately 88% and 86% inhibition of mammosphere production versus control, respectively.

In a separate experiment for the control sample (no test agent added) a mean of the quadruplicate measurements yielded 32±6 mammospheres whereas the kinase inhibitor Lapatinib, approved for treating breast cancer, at 1 uM gave 17±4 mammospheres. Cpd 25 at 1 μM or 10 μM yielded 12±3 and 7±2 mammospheres respectively. Cpd 43 at 1 μM or 10 μM yielded 18±6 and 16±6 mammospheres respectively. Thus, Cpd 25 and Cpd 43 at 1 μM gave approximately 69 and 53% inhibition (respectively) of mammosphere production versus control whereas Lapatinib at this same concentration gave 55% inhibition of mammosphere production. At the higher concentration of 10 μM Cpd 25 and Cpd 43 gave approximately 82% and 58% inhibition of mammosphere production versus control, respectively.

Representative compounds of the invention along with NRM spectral data are depicted in Tables 8 and 9 respectively as merely illustrative and not limiting of the scope of the invention in any way.

TABLE 8

Illustrative compounds of formula I.

| Compound number | Structure | PC3 pAKT IC50 (μMolar) | IC50 PC3 Proliferation (μMolar) | Mass Expected | Mass Found | Synthetic Method |
| --- | --- | --- | --- | --- | --- | --- |
| 1 | 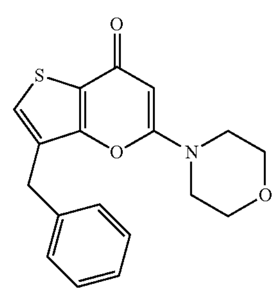 [SMILES: O=c1cc(N2CCOCC2)oc2c(Cc3ccccc3)csc12] | 0.864 | 20.18 | 327 | 328 (M + H) | B |
| 2 | 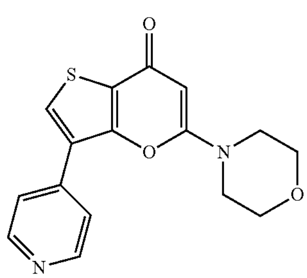 [SMILES: O=c1cc(N2CCOCC2)oc2c(-c3ccncc3)csc12] | 3.031 | 18.5 | 314 | 356 (M + H + CH3CN) | B |
| 3 | 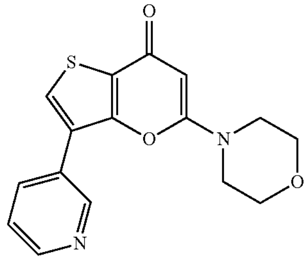 [SMILES: O=c1cc(N2CCOCC2)oc2c(-c3cccnc3)csc12] | 4.872 | 10.88 | 314 | 315 (M + H) | B |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 4 | 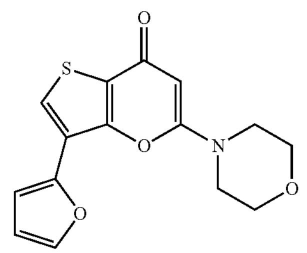 [SMILES: O=c1cc(N2CCOCC2)oc2c(-c3ccco3)csc12] | 0.93 | 5.9 | 303 | 304 (M + H) | A |
| 5 | 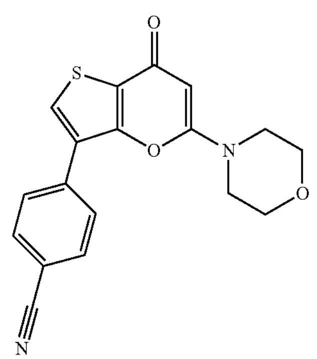 [SMILES: N#Cc1ccc(-c2csc3c(=O)cc(N4CCOCC4)oc23)cc1] | 7.3 | ND | 338 | 339 (M + H) | A |
| 6 | 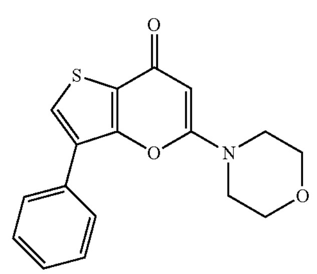 [SMILES: O=c1cc(N2CCOCC2)oc2c(-c3ccccc3)csc12] | 0.55 | 4.11 | 313 | 314 (M + H) | A |
| 7 | 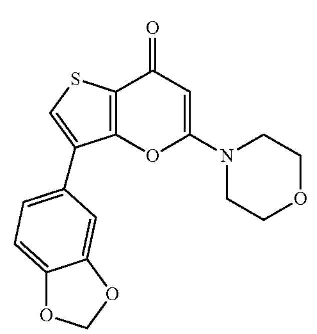 [SMILES: O=c1cc(N2CCOCC2)oc2c(-c3ccc4c(c3)OCO4)csc12] | 0.54 | 1.74 | 357 | 358 (M + H) | A |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 8 | 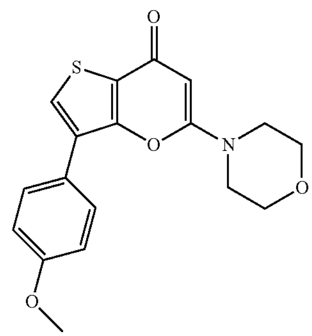 [SMILES: COc1ccc(-c2csc3c(=O)cc(N4CCOCC4)oc23)cc1] | 0.98 | 1.82 | 343 | 344 (M + H) | A |
| 9 | 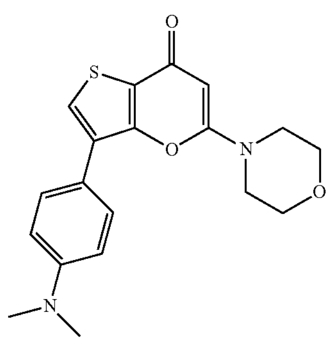 [SMILES: CN(C)c1ccc(-c2csc3c(=O)cc(N4CCOCC4)oc23)cc1] | 0.78 | 2.01 | 356 | 357 (M + H) | A |
| 10 | 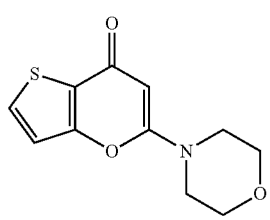 [SMILES: O=c1cc(N2CCOCC2)oc2ccsc12] | ND | ND | 237 | 238 (M + H) | B |
| 11 | 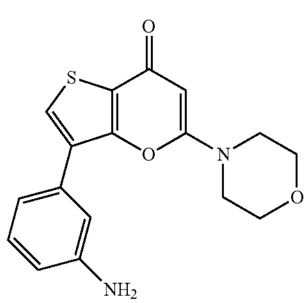 [SMILES: Nc1cccc(-c2csc3c(=O)cc(N4CCOCC4)oc23)c1] | 6.317 | 6.293 | 328 | 329 (M + H) | B |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 12 | 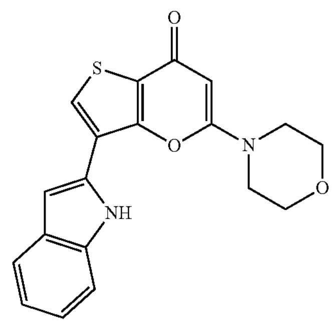 [SMILES: O=c1cc(N2CCOCC2)oc2c(-c3cc4ccccc4[nH]3)csc12] | 1.574 | 8.552 | 352 | 353 (M + H) | B |
| 13 | 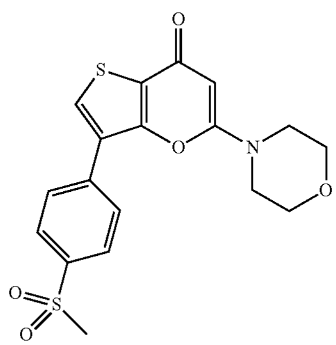 [SMILES: CS(=O)(=O)c1ccc(-c2csc3c(=O)cc(N4CCOCC4)oc23)cc1] | 5.295 | 15.31 | 391 | 392 (M + H) | A |
| 14 | 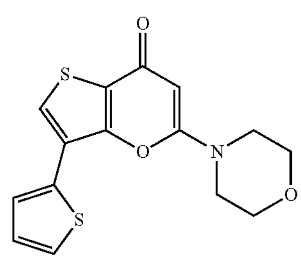 [SMILES: O=c1cc(N2CCOCC2)oc2c(-c3cccs3)csc12] | 1.021 | 4.362 | 319 | 320 (M + H) | A |
| 15 | 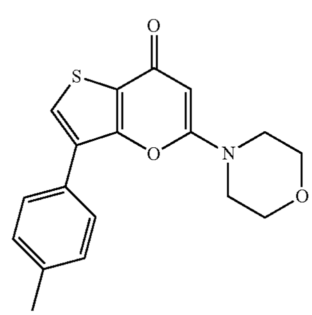 [SMILES: Cc1ccc(-c2csc3c(=O)cc(N4CCOCC4)oc23)cc1] | 0.948 | 4.475 | 327 | 328 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 16 | 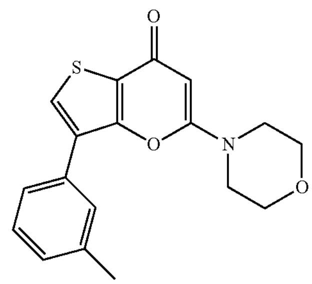 [SMILES: Cc1cccc(-c2csc3c(=O)cc(N4CCOCC4)oc23)c1] | 1.229 | 6.028 | 327 | 328 (M + H) | A |
| 17 | 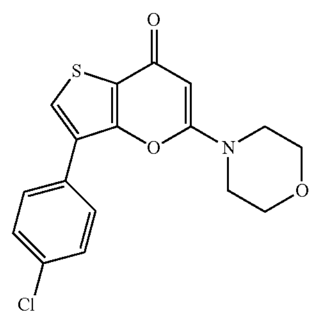 [SMILES: O=c1cc(N2CCOCC2)oc2c(-c3ccc(Cl)cc3)csc12] | 1.41 | 28.96 | 347 | 348 (M + H) | A |
| 18 | 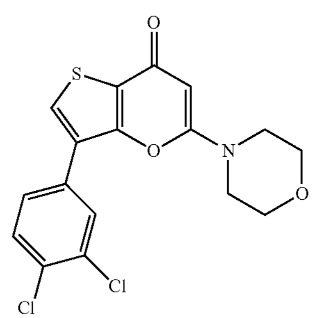 [SMILES: O=c1cc(N2CCOCC2)oc2c(-c3ccc(Cl)c(Cl)c3)csc12] | 0.913 | 37.62 | 381 | 382 (M + H) | A |
| 19 | 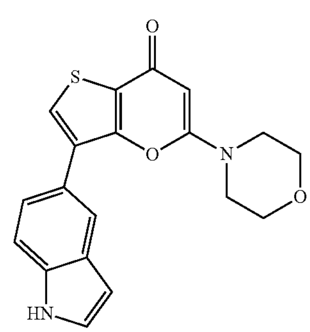 [SMILES: O=c1cc(N2CCOCC2)oc2c(-c3ccc4[nH]ccc4c3)csc12] | 0.901 | 8.132 | 352 | 353 (M + H) | B |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 20 | 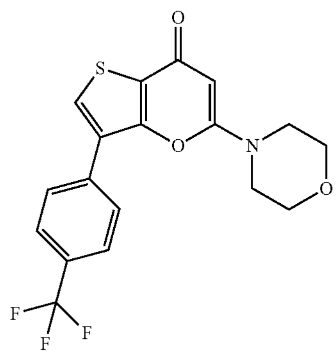 [SMILES: O=c1cc(N2CCOCC2)oc2c(-c3ccc(C(F)(F)F)cc3)csc12] | ND | 774.5 | 381 | 382 (M + H) | B |
| 21 | 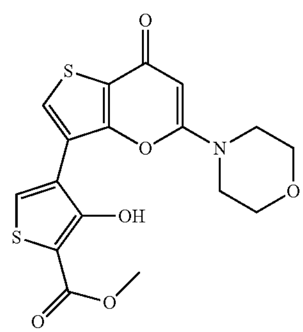 [SMILES: COC(=O)c1scc(-c2csc3c(=O)cc(N4CCOCC4)oc23)c1O] | 1.038 | 34.81 | 393 | 392 (M − H) | E |
| 22 | 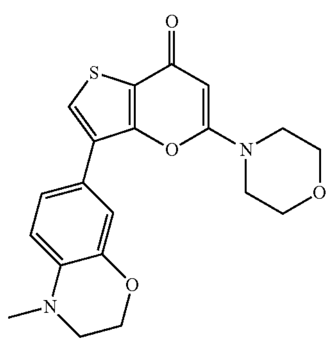 [SMILES: CN1CCOc2cc(-c3csc4c(=O)cc(N5CCOCC5)oc34)ccc21] | 0.609 | 1.054 | 384 | 385 (M + H) | A |
| 23 | 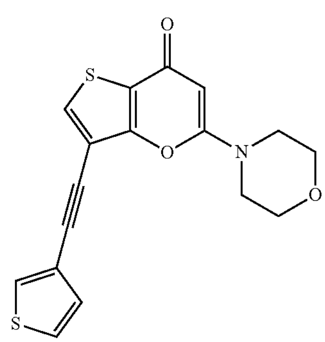 [SMILES: O=c1cc(N2CCOCC2)oc2c(C#Cc3ccsc3)csc12] | 1.274 | 7.347 | 343 | 344 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 24 | 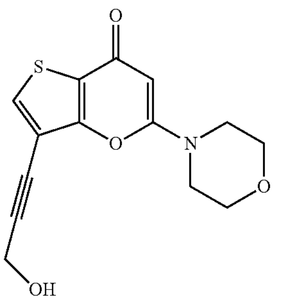 [SMILES: O=c1cc(N2CCOCC2)oc2c(C#CCO)csc12] | 4.606 | 28.17 | 291 | 292 (M + H) | A |
| 25 | 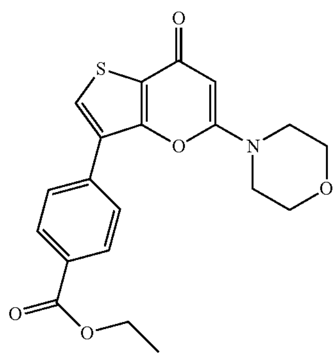 [SMILES: CCOC(=O)c1ccc(-c2csc3c(=O)cc(N4CCOCC4)oc23)cc1] | ND | 1.233-3.141 | 385 | 386 (M + H) | B |
| 26 | 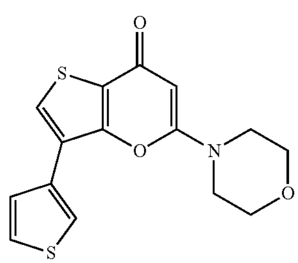 [SMILES: O=c1cc(N2CCOCC2)oc2c(-c3ccoc3)csc12] | 1.558 | 5.597 | 319 | 320 (M + H) | A |
| 27 | 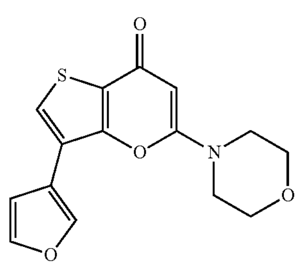 | 3.235 | 9.26 | 303 | 304 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 28 | 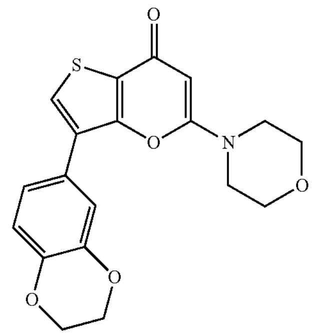 [SMILES: O=c1cc(N2CCOCC2)oc2c(-c3ccc4c(c3)OCCO4)csc12] | 0.161-0.44 | 1.298-1.914 | 371 | 372 (M + H) | A |
| 29 | 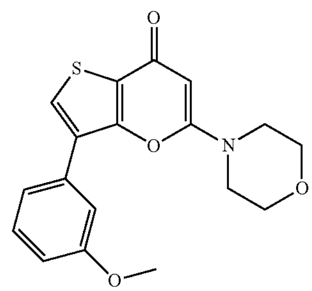 [SMILES: COc1cccc(-c2csc3c(=O)cc(N4CCOCC4)oc23)c1] | 1.067 | 4.759 | 343 | 344 (M + H) | A |
| 30 | 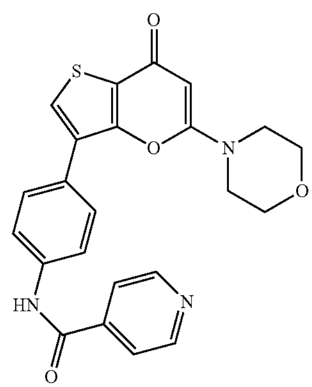 [SMILES: O=C(Nc1ccc(-c2csc3c(=O)cc(N4CCOCC4)oc23)cc1)c1ccncc1] | ND | 5.799 | 433 | 434 (M + H) | F |
| 31 | 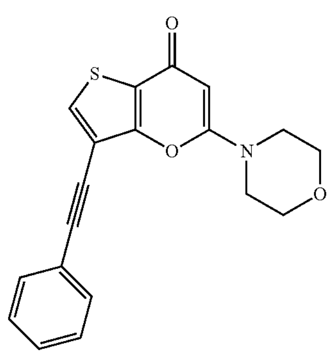 [SMILES: O=c1cc(N2CCOCC2)oc2c(C#Cc3ccccc3)csc12] | ND | 3.689 | 337 | 338 (M + H) | C |

TABLE 8-continued
Illustrative compounds of formula I.
| Compound number | Structure | PC3 pAKT IC50 (μMolar) | IC50 PC3 Proliferation (μMolar) | Mass Expected | Mass Found | Synthetic Method |
|---|---|---|---|---|---|---|
| 32 | 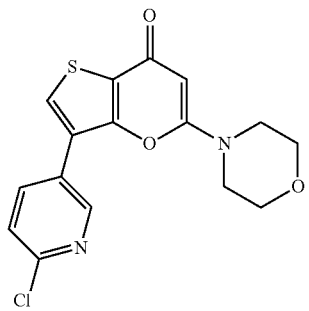 [SMILES: O=c1cc(N2CCOCC2)oc2c(-c3ccc(Cl)nc3)csc12] | ND | 9.008 | 348 | 349 (M + H) | A |
| 33 | 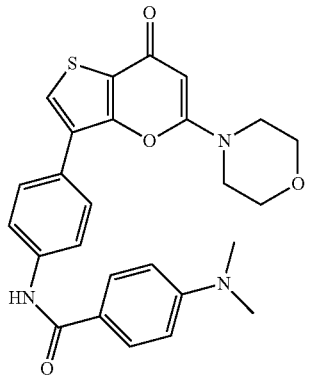 [SMILES: CN(C)c1ccc(C(=O)Nc2ccc(-c3csc4c(=O)cc(N5CCOCC5)oc34)cc2)cc1] | ND | ND | 475 | 474 (M − H) | F |
| 34 | 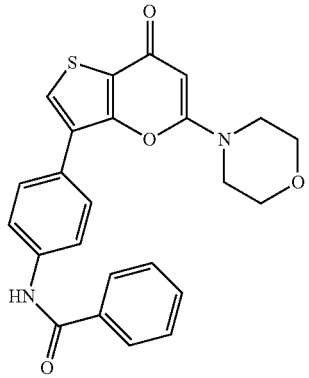 [SMILES: O=C(Nc1ccc(-c2csc3c(=O)cc(N4CCOCC4)oc23)cc1)c1ccccc1] | ND | 2 | 432 | 431 (M − H) | F |
| 35 | 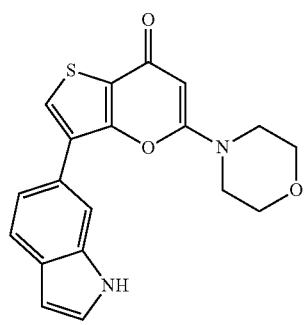 [SMILES: O=c1cc(N2CCOCC2)oc2c(-c3ccc4cc[nH]c4c3)csc12] | ND | 2.699-5.59 | 352 | 353 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 36 | 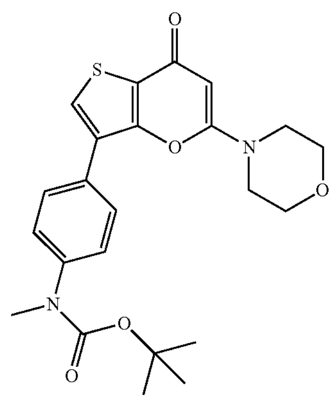 [SMILES: CN(C(=O)OC(C)(C)C)c1ccc(-c2csc3c(=O)cc(N4CCOCC4)oc23)cc1] | ND | 2.694 | 442 | 443 (M + H) | A |
| 37 | 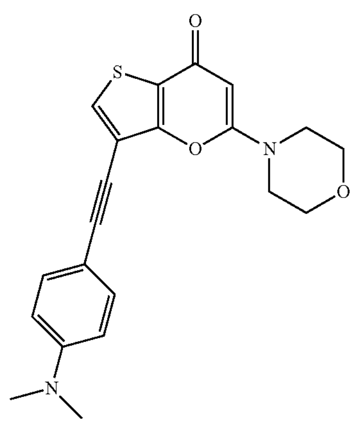 [SMILES: CN(C)c1ccc(C#Cc2csc3c(=O)cc(N4CCOCC4)oc23)cc1] | ND | 2.496 | 380 | 381 (M + H) | C |
| 38 | 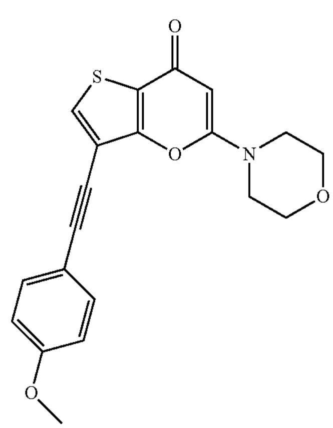 [SMILES: COc1ccc(C#Cc2csc3c(=O)cc(N4CCOCC4)oc23)cc1] | 0.363 | 8.421 | 367 | 368 (M + H) | C |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 39 | 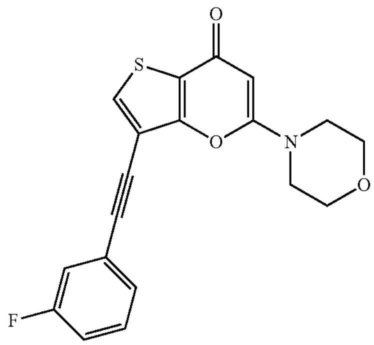 [SMILES: O=c1cc(N2CCOCC2)oc2c(C#Cc3cccc(F)c3)csc12] | ND | 3.31 | 355 | 356 (M + H) | C |
| 40 | 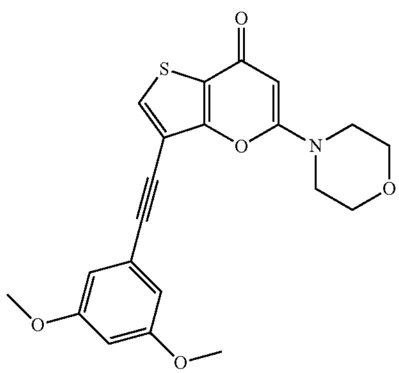 [SMILES: COc1cc(C#Cc2csc3c(=O)cc(N4CCOCC4)oc23)cc(OC)c1] | ND | 1.803 | 397 | 398 (M + H) | C |
| 41 | 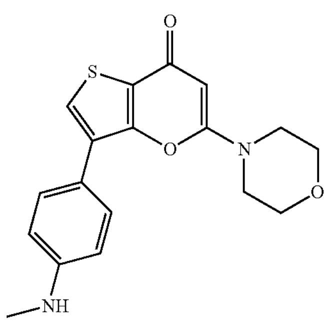 [SMILES: CNc1ccc(-c2csc3c(=O)cc(N4CCOCC4)oc23)cc1] | ND | 2.067 | 342 | 343 (M + H) | A |
| 42 | 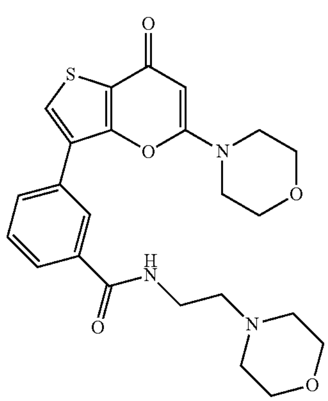 [SMILES: O=C(NCCN1CCOCC1)c1cccc(-c2csc3c(=O)cc(N4CCOCC4)oc23)c1] | ND | 7.844 | 369 | 370 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 43 | 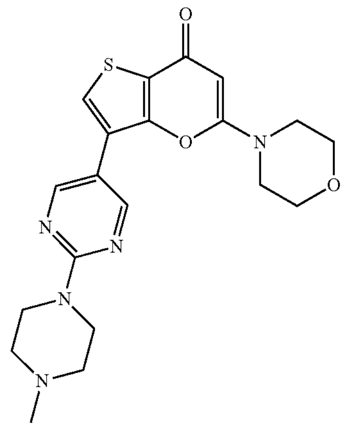 [SMILES: CN1CCN(c2ncc(-c3csc4c(=O)cc(N5CCOCC5)oc34)cn2)CC1] | ND | 9.351 | 413 | 414 (M + H) | A |
| 44 | 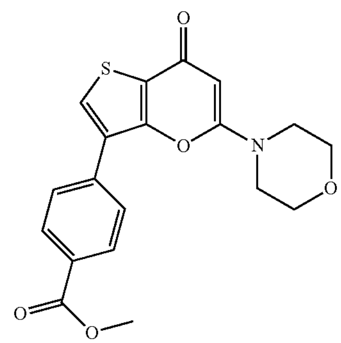 [SMILES: COC(=O)c1ccc(-c2csc3c(=O)cc(N4CCOCC4)oc23)cc1] | ND | 4.394 | 371 | 372 (M + H) | B |
| 45 | 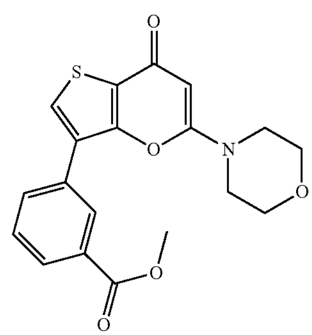 [SMILES: COC(=O)c1cccc(-c2csc3c(=O)cc(N4CCOCC4)oc23)c1] | ND | 4.673 | 371 | 372 (M + H) | B |
| 46 | 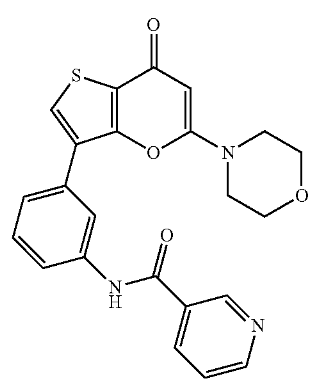 [SMILES: O=C(Nc1cccc(-c2csc3c(=O)cc(N4CCOCC4)oc23)c1)c1cccnc1] | ND | 62.15 | 433 | 434 (M + H) | F |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 47 | 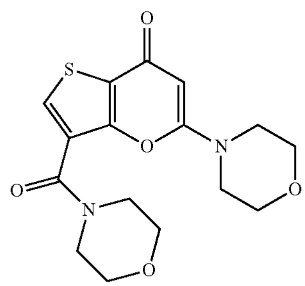 [SMILES: O=C(c1csc2c(=O)cc(N3CCOCC3)oc12)N1CCOCC1] | ND | ND | 350 | 351 (M + H) | D |
| 48 | 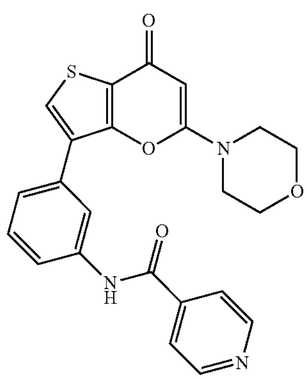 [SMILES: O=C(Nc1cccc(-c2csc3c(=O)cc(N4CCOCC4)oc23)c1)c1ccncc1] | ND | ND | 433 | 434 (M + H) | F |
| 49 | 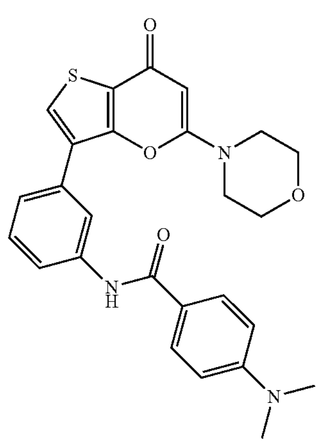 [SMILES: CN(C)c1ccc(C(=O)Nc2cccc(-c3csc4c(=O)cc(N5CCOCC5)oc34)c2)cc1] | ND | 3.181 | 475 | 474 (M − H) | F |

TABLE 8-continued
Illustrative compounds of formula I.
| Compound number | Structure | PC3 pAKT IC50 (μMolar) | IC50 PC3 Proliferation (μMolar) | Mass Expected | Mass Found | Synthetic Method |
|---|---|---|---|---|---|---|
| 50 | 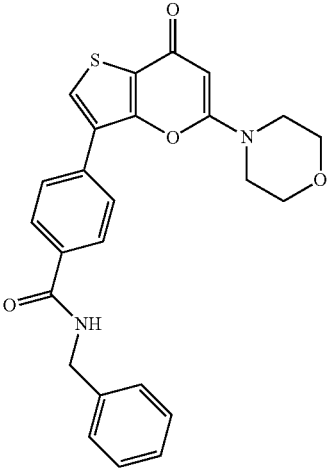 [SMILES: O=C(NCc1ccccc1)c1ccc(-c2csc3c(=O)cc(N4CCOCC4)oc23)cc1] | ND | 4.764 | 446 | 447 (M + H) | G |
| 51 | 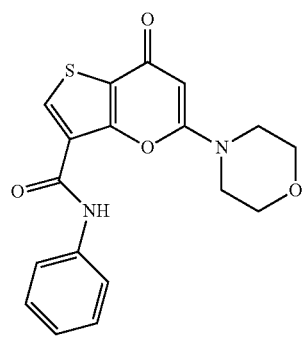 [SMILES: O=C(Nc1ccccc1)c1csc2c(=O)cc(N3CCOCC3)oc12] | ND | 23.77 | 356 | 357 (M + H) | D |
| 52 | 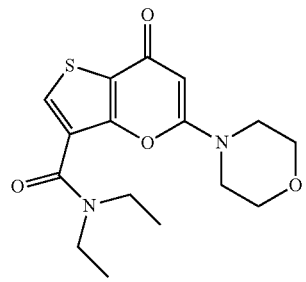 [SMILES: CCN(CC)C(=O)c1csc2c(=O)cc(N3CCOCC3)oc12] | ND | 157.1 | 336 | 337 (M + H) | D |
| 53 | 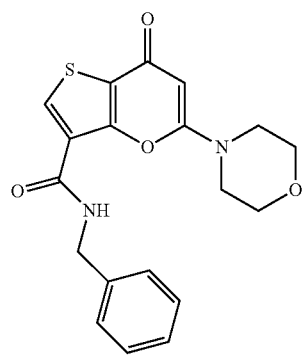 [SMILES: O=C(NCc1ccccc1)c1csc2c(=O)cc(N3CCOCC3)oc12] | ND | 112.8 | 370 | 371 (M + H) | D |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 54 | 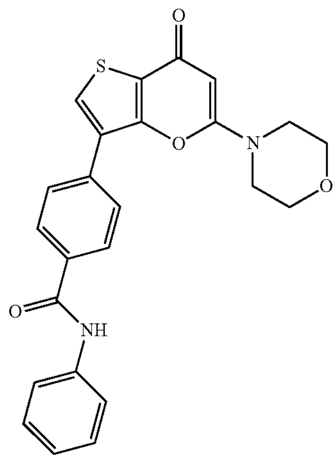 [SMILES: O=C(Nc1ccccc1)c1ccc(-c2csc3c(=O)cc(N4CCOCC4)oc23)cc1] | ND | ND | 432 | 433 (M + H) | G |
| 55 | 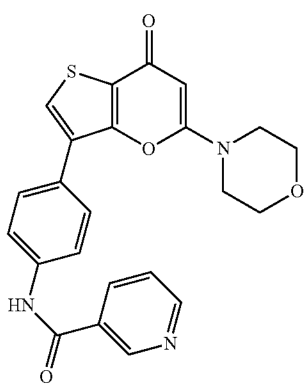 [SMILES: O=C(Nc1ccc(-c2csc3c(=O)cc(N4CCOCC4)oc23)cc1)c1cccnc1] | ND | 1.053-1.504 | 433 | 434 (M + H) | F |
| 56 | 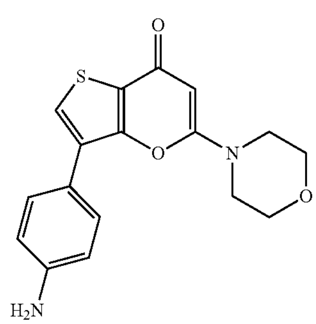 [SMILES: Nc1ccc(-c2csc3c(=O)cc(N4CCOCC4)oc23)cc1] | ND | ND | 328 | 329 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 57 | 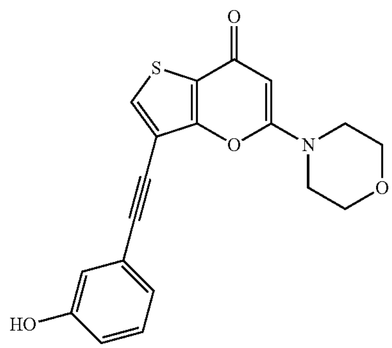 [SMILES: O=c1cc(N2CCOCC2)oc2c(C#Cc3cccc(O)c3)csc12] | ND | ND | 353 | 354 (M + H) | C |
| 58 | 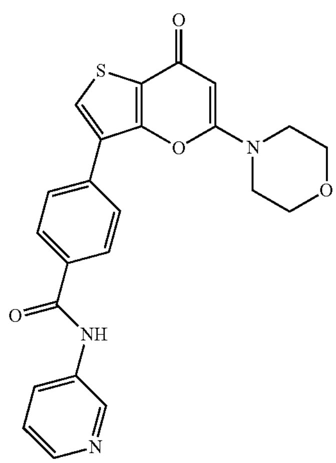 [SMILES: O=C(Nc1cccnc1)c1ccc(-c2csc3c(=O)cc(N4CCOCC4)oc23)cc1] | ND | 16.74 | 433 | 434 (M + H) | G |
| 59 | 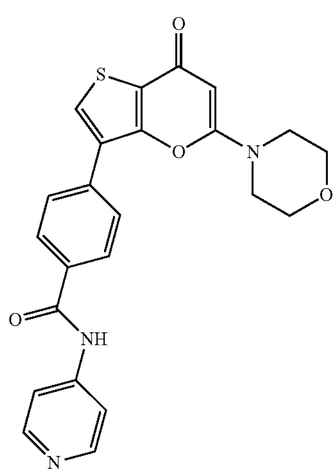 [SMILES: O=C(Nc1ccncc1)c1ccc(-c2csc3c(=O)cc(N4CCOCC4)oc23)cc1] | ND | 17.49 | 433 | 434 (M + H) | G |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 60 | 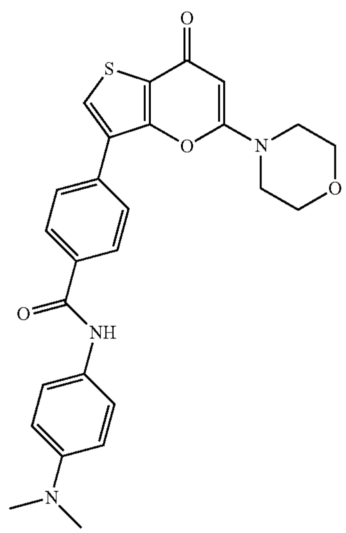 [SMILES: CN(C)c1ccc(NC(=O)c2ccc(-c3csc4c(=O)cc(N5CCOCC5)oc34)cc2)cc1] | ND | ND | 475 | 476 (M + H) | G |
| 61 | 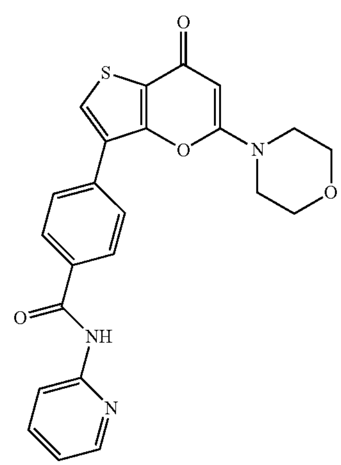 [SMILES: O=C(Nc1ccccn1)c1ccc(-c2csc3c(=O)cc(N4CCOCC4)oc23)cc1] | ND | 4.999 | 433 | 434 (M + H) | G |
| 62 | 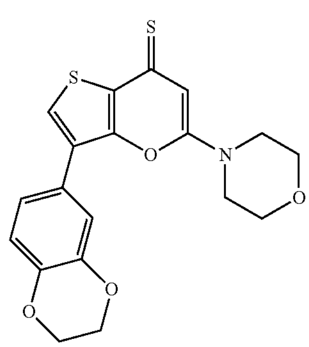 [SMILES: S=c1cc(N2CCOCC2)oc2c(-c3ccc4c(c3)OCCO4)csc12] | ND | ND | 387 | 388 (M + H) | I |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 63 | 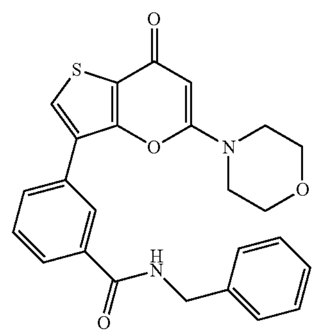 [SMILES: O=C(NCc1ccccc1)c1cccc(-c2csc3c(=O)cc(N4CCOCC4)oc23)c1] | ND | 7.841 | 446 | 447 (M + H) | G |
| 64 | 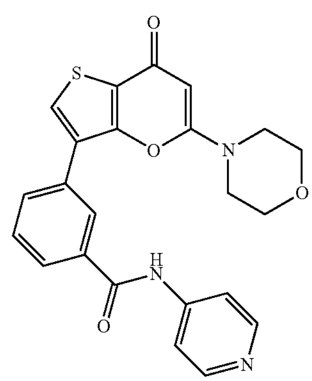 [SMILES: O=C(Nc1ccncc1)c1cccc(-c2csc3c(=O)cc(N4CCOCC4)oc23)c1] | ND | 17.89 | 433 | 434 (M + H) | G |
| 65 | 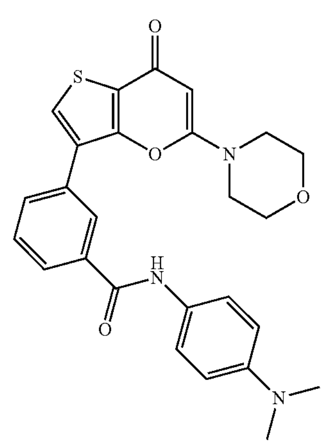 [SMILES: CN(C)c1ccc(NC(=O)c2cccc(-c3csc4c(=O)cc(N5CCOCC5)oc34)c2)cc1] | ND | 12.66 | 475 | 476 (M + H) | G |

TABLE 8-continued
Illustrative compounds of formula I.
| Compound number | Structure | PC3 pAKT IC50 (μMolar) | IC50 PC3 Proliferation (μMolar) | Mass Expected | Mass Found | Synthetic Method |
|---|---|---|---|---|---|---|
| 66 | 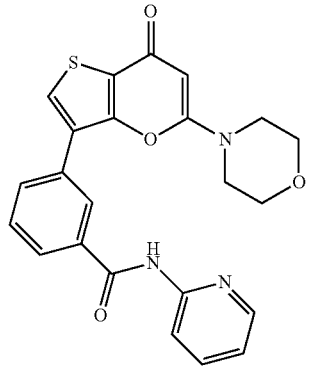 [SMILES: O=C(Nc1ccccn1)c1cccc(-c2csc3c(=O)cc(N4CCOCC4)oc23)c1] | ND | 6.905 | 433 | 434 (M + H) | G |
| 67 | 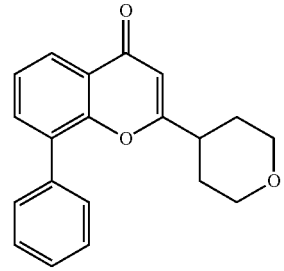 [SMILES: O=c1cc(C2CCOCC2)oc2c(-c3ccccc3)cccc12] | ND | 95.84 | 306 | 307 (M + H) | H |
| 68 | 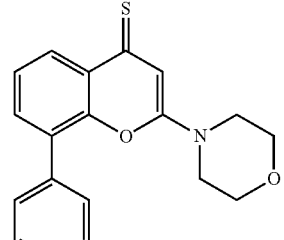 | ND | 34.81 | 323 | 324 (M + H) | I |
| 69 | 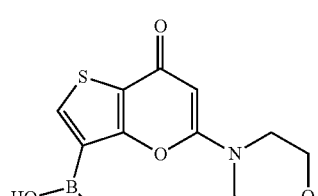 | ND | ND | 282 | 283 (M + H) | E |
| 70 | 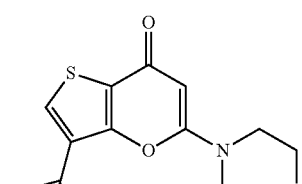 | ND | ND | 281 | 208 (M − H) | J |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 71 | 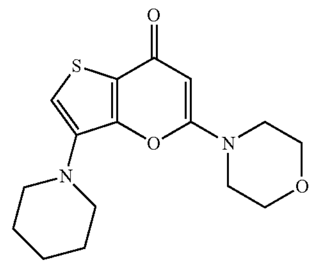 [SMILES: O=c1cc(N2CCOCC2)oc2c(N3CCCCC3)csc12] | ND | ND | 320 | 321 (M + H) | K |
| 72 | 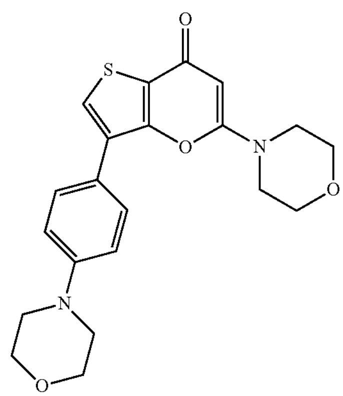 [SMILES: O=c1cc(N2CCOCC2)oc2c(-c3ccc(N4CCOCC4)cc3)csc12] | ND | ND | 398 | 399 (M + H) | L |
| 73 | 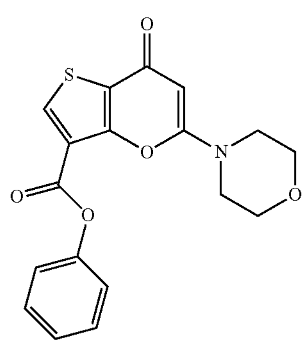 [SMILES: O=C(Oc1ccccc1)c1csc2c(=O)cc(N3CCOCC3)oc12] | ND | ND | 357 | 358 (M + H) | M |
| 74 | 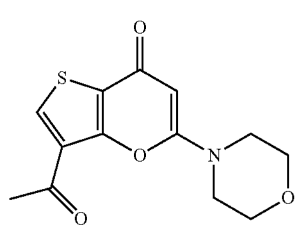 [SMILES: CC(=O)c1csc2c(=O)cc(N3CCOCC3)oc12] | ND | ND | 279 | 280 (M + H) | N |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 75 | 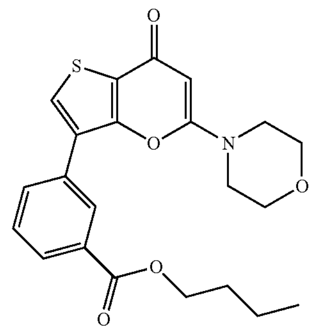 [SMILES: CCCCOC(=O)c1cccc(-c2csc3c(=O)cc(N4CCOCC4)oc23)c1] | ND | ND | 413 | 414 (M + H) | O |
| 76 | 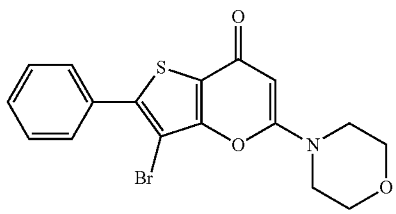 [SMILES: O=c1cc(N2CCOCC2)oc2c(Br)c(-c3ccccc3)sc12] | ND | ND | 391 | 392 (M + H) | P |
| 77 | 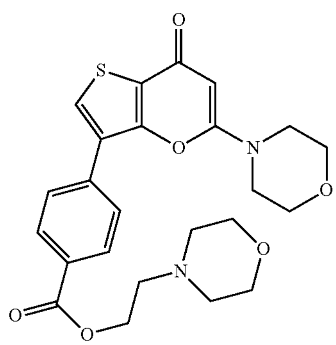 [SMILES: O=C(OCCN1CCOCC1)c1ccc(-c2csc3c(=O)cc(N4CCOCC4)oc23)cc1] | ND | ND | 470 | 471 (M + H) | R |
| 78 | 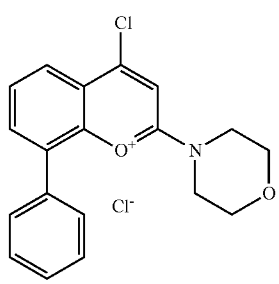 [SMILES: Clc1cc(N2CCOCC2)[o+]c2c(-c3ccccc3)cccc12 ; [Cl-]] | ND | ND | 326 | 326 (M+) | S |
| 79 | 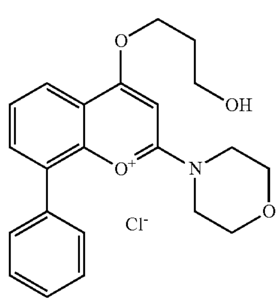 [SMILES: OCCCOc1cc(N2CCOCC2)[o+]c2c(-c3ccccc3)cccc12 ; [Cl-]] | ND | ND | 366 | 366 (M+) | T |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 80 | 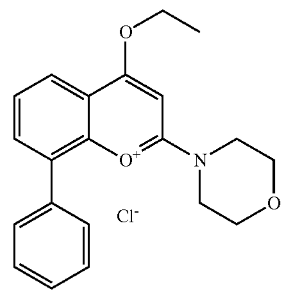 [SMILES: CCOc1cc(N2CCOCC2)[o+]c2c(-c3ccccc3)cccc12 ; [Cl-]] | ND | ND | 336 | 336 (M+) 377 (M + CH3CN) | U |
| 81 | 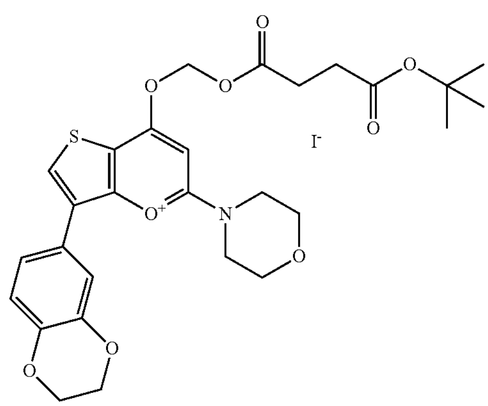 [SMILES: CC(C)(C)OC(=O)CCC(=O)OCOc1cc(N2CCOCC2)[o+]c2c(-c3ccc4c(c3)OCCO4)csc12 ; [I-]] | ND | ND | 558 | 558 (M+) | V |
| 82 | 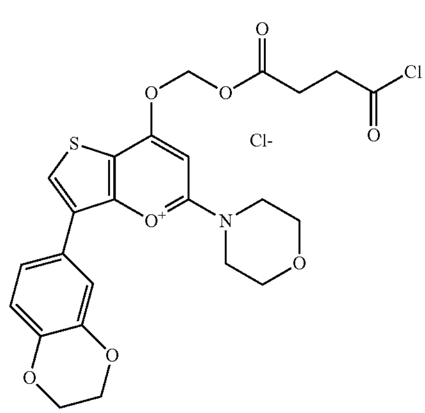 [SMILES: O=C(Cl)CCC(=O)OCOc1cc(N2CCOCC2)[o+]c2c(-c3ccc4c(c3)OCCO4)csc12 ; [Cl-]] | ND | ND | ND | ND | W |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 83 | 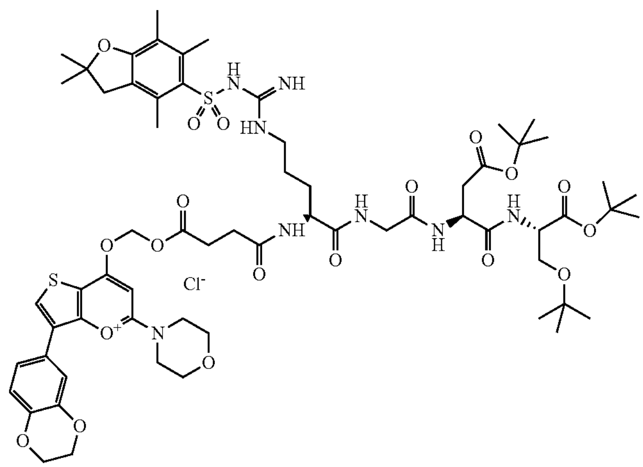 [SMILES: Cc1c(C)c(S(=O)(=O)NC(=N)NCCC[C@H](NC(=O)CCC(=O)OCOc2cc(N3CCOCC3)[o+]c3c(-c4ccc5c(c4)OCCO5)csc23)C(=O)NCC(=O)N[C@@H](CC(=O)OC(C)(C)C)C(=O)N[C@@H](COC(C)(C)C)C(=O)OC(C)(C)C)c(C)c2c1OC(C)(C)C2 ; [Cl-]] | ND | ND | 1337 | 669 ([M/Z] + 1) (Z = 2) | X |
| 84 | 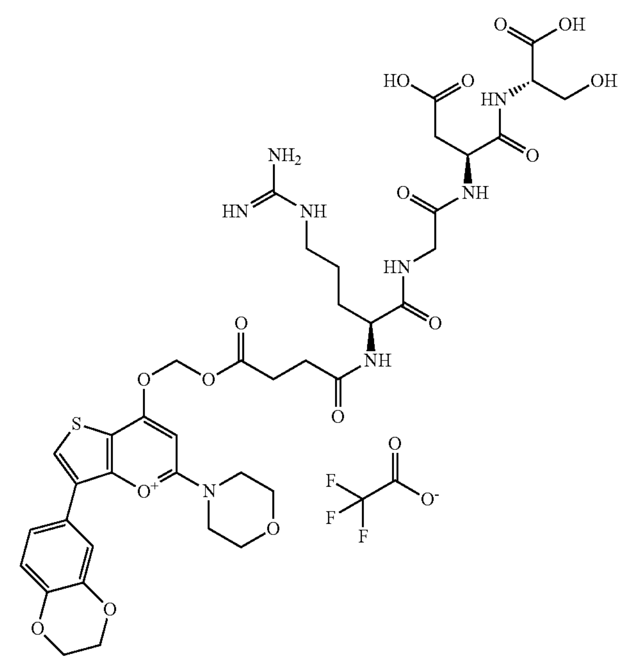 [SMILES: N=C(N)NCCC[C@H](NC(=O)CCC(=O)OCOc1cc(N2CCOCC2)[o+]c2c(-c3ccc4c(c3)OCCO4)csc12)C(=O)NCC(=O)N[C@@H](CC(=O)O)C(=O)N[C@@H](CO)C(=O)O ; O=C([O-])C(F)(F)F] | ND | ND | 917 | 459 ([M/Z] + 1) (Z = 2) | Y |
| 85 | 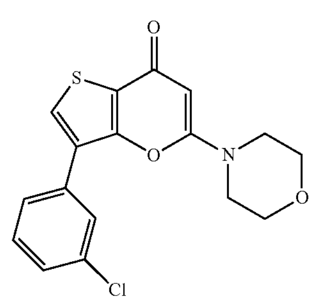 [SMILES: O=c1cc(N2CCOCC2)oc2c(-c3cccc(Cl)c3)csc12] | ND | 3.452 | 347 | 348 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 86 | 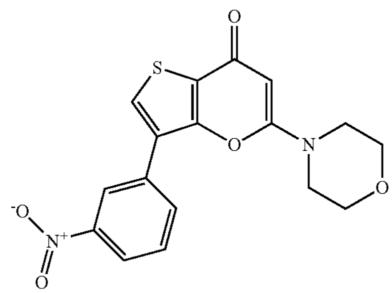 | ND | ND | 358 | 359 (M + H) | B |
| 87 | 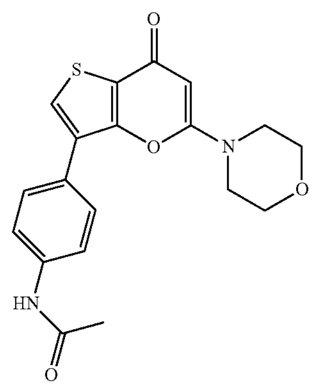 [SMILES: CC(=O)Nc1ccc(-c2csc3c(=O)cc(N4CCOCC4)oc23)cc1] | ND | ND | 370 | 371 (M + H) | F |
| 88 | 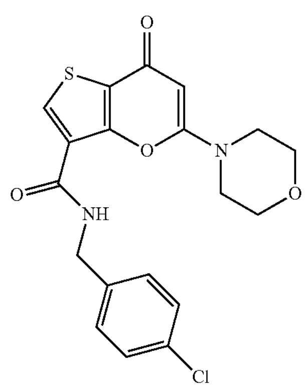 [SMILES: O=C(NCc1ccc(Cl)cc1)c1csc2c(=O)cc(N3CCOCC3)oc12] | ND | 21.97 | 404 | 405 (M + H) | D |
| 89 | 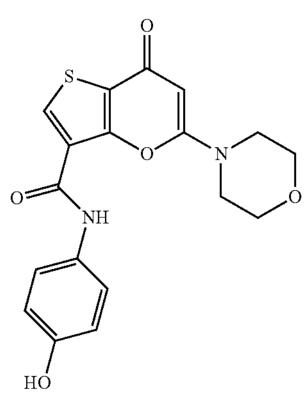 [SMILES: O=C(Nc1ccc(O)cc1)c1csc2c(=O)cc(N3CCOCC3)oc12] | ND | ND | 372 | 373 (M + H) | D |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 90 | 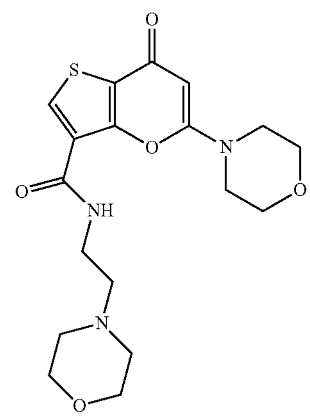 [SMILES: O=C(NCCN1CCOCC1)c1csc2c(=O)cc(N3CCOCC3)oc12] | ND | 19.93 | 393 | 394 (M + H) | D |
| 91 | 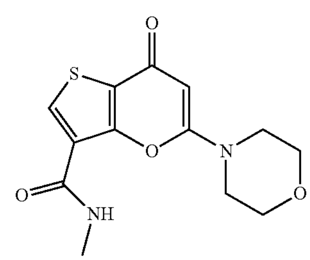 [SMILES: CNC(=O)c1csc2c(=O)cc(N3CCOCC3)oc12] | ND | ND | 294 | 295 (M + H) | D |
| 92 | 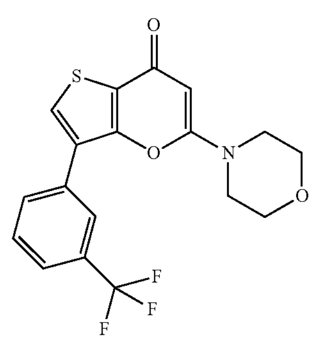 [SMILES: O=c1cc(N2CCOCC2)oc2c(-c3cccc(C(F)(F)F)c3)csc12] | ND | 6.281 | 381 | 382 (M + H) | A |
| 93 | 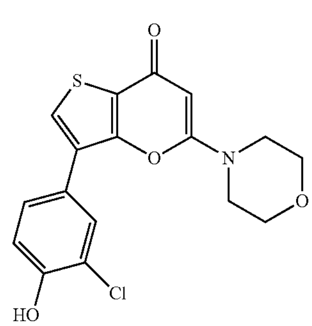 [SMILES: O=c1cc(N2CCOCC2)oc2c(-c3ccc(O)c(Cl)c3)csc12] | ND | 6.14-9.431 | 363 | 364 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 94 | 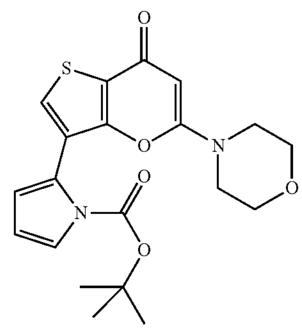 [SMILES: CC(C)(C)OC(=O)n1cccc1-c1csc2c(=O)cc(N3CCOCC3)oc12] | ND | ND | 402 | 403 (M + H) | A |
| 95 | 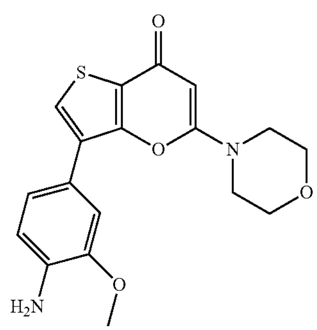 [SMILES: COc1cc(-c2csc3c(=O)cc(N4CCOCC4)oc23)ccc1N] | ND | 81.87 | 358 | 359 (M + H) | A |
| 96 | 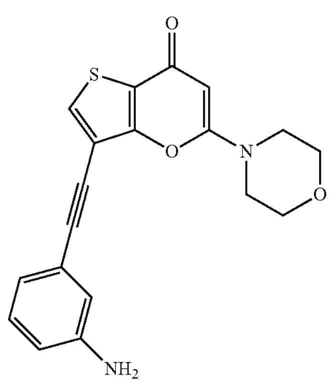 [SMILES: Nc1cccc(C#Cc2csc3c(=O)cc(N4CCOCC4)oc23)c1] | ND | 24.84 | 352 | 353 (M + H) | C |
| 97 | 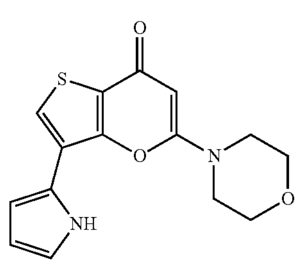 [SMILES: O=c1cc(N2CCOCC2)oc2c(-c3ccc[nH]3)csc12] | ND | ND | 302 | 303 (M + H) | Z |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 98 | 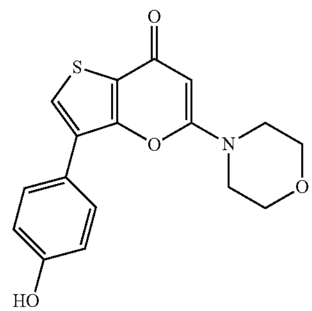 | ND | 6.124 | 329 | 330 (M + H) | A |
| 99 | 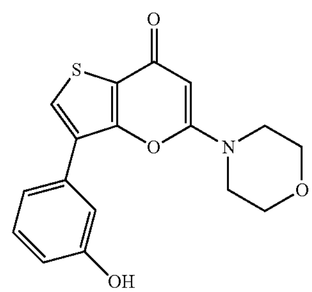 [SMILES: O=c1cc(N2CCOCC2)oc2c(-c3cccc(O)c3)csc12] | ND | 16.6 | 329 | 330 (M + H) | A |
| 100 | 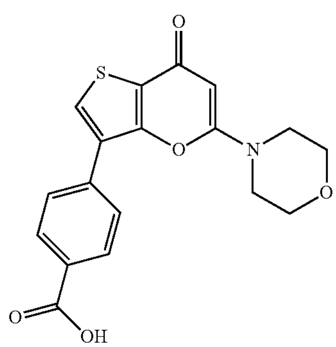 [SMILES: O=C(O)c1ccc(-c2csc3c(=O)cc(N4CCOCC4)oc23)cc1] | ND | 128.9 | 357 | 358 (M + H) 356 (M − H) | B |
| 101 | 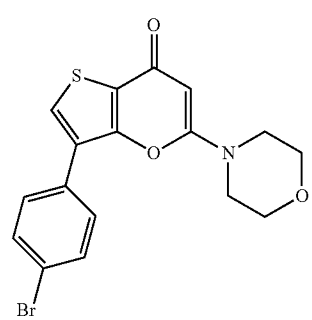 | ND | 21.76 | 392 | 392 (M+) | E |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 102 | 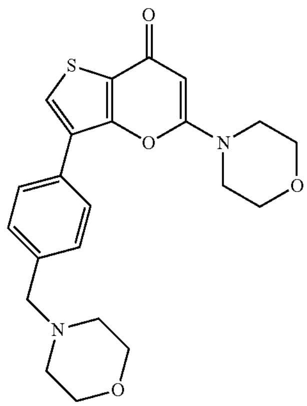 [SMILES: O=c1cc(N2CCOCC2)oc2c(-c3ccc(CN4CCOCC4)cc3)csc12] | ND | ND | 412 | 413 (M + H) | A |
| 103 | 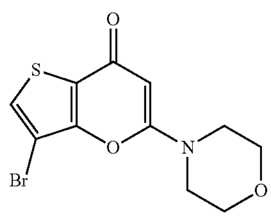 [SMILES: O=c1cc(N2CCOCC2)oc2c(Br)csc12] | ND | ND | 316 | 316 (M+) | A |
| 104 | 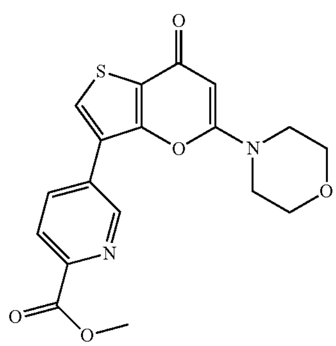 [SMILES: COC(=O)c1ccc(-c2csc3c(=O)cc(N4CCOCC4)oc23)cn1] | ND | ND | 372 | 373 (M + H) | A |
| 105 | 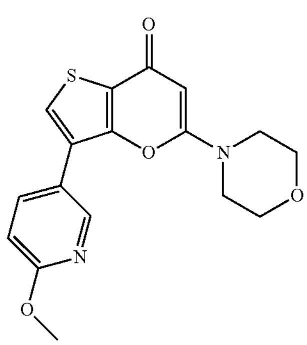 [SMILES: COc1ccc(-c2csc3c(=O)cc(N4CCOCC4)oc23)cn1] | ND | ND | 344 | 345 (M + H) | A |

TABLE 8-continued

Illustrative compounds of formula I.

| Compound number | Structure | PC3 pAKT IC50 (μMolar) | IC50 PC3 Proliferation (μMolar) | Mass Expected | Mass Found | Synthetic Method |
|---|---|---|---|---|---|---|
| 106 | 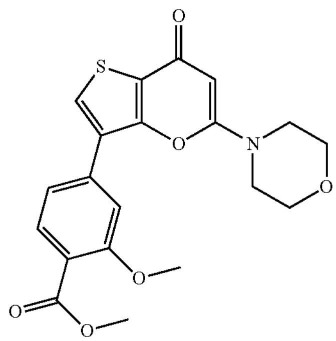 [SMILES: COC(=O)c1ccc(-c2csc3c(=O)cc(N4CCOCC4)oc23)cc1OC] | ND | ND | 401 | 402 (M + H) | A |
| 107 | 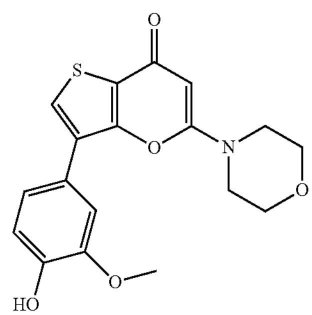 [SMILES: COc1cc(-c2csc3c(=O)cc(N4CCOCC4)oc23)ccc1O] | ND | ND | 359 | 360 (M + H) | A |
| 108 | 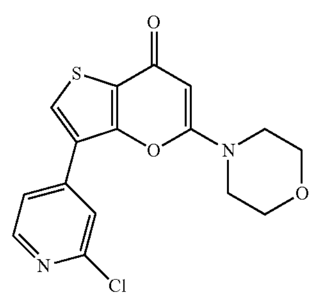 [SMILES: O=c1cc(N2CCOCC2)oc2c(-c3ccnc(Cl)c3)csc12] | ND | ND | 348 | 349 (M + H) | A |
| 109 | 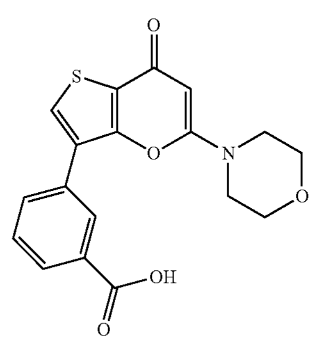 [SMILES: O=C(O)c1cccc(-c2csc3c(=O)cc(N4CCOCC4)oc23)c1] | ND | ND | 357 | 356 (M − H) | B |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 110 | 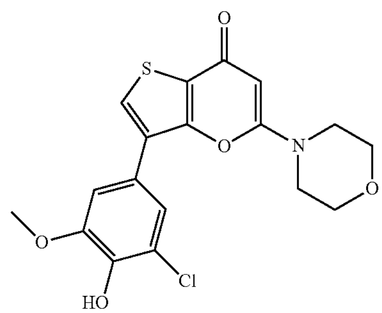 [SMILES: COc1cc(-c2csc3c(=O)cc(N4CCOCC4)oc23)cc(Cl)c1O] | ND | ND | 393 | 394 (M + H) | A |
| 111 | 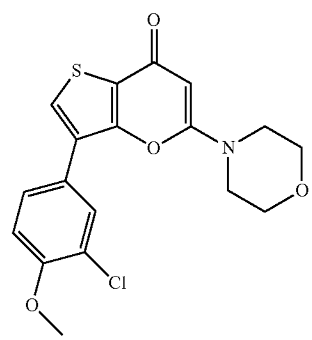 [SMILES: COc1ccc(-c2csc3c(=O)cc(N4CCOCC4)oc23)cc1Cl] | ND | ND | 377 | 378 (M + H) | A |
| 112 | 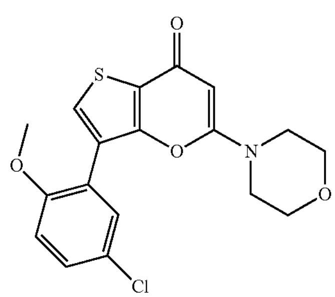 [SMILES: COc1ccc(Cl)cc1-c1csc2c(=O)cc(N3CCOCC3)oc12] | ND | ND | 377 | 378 (M + H) | A |
| 113 | 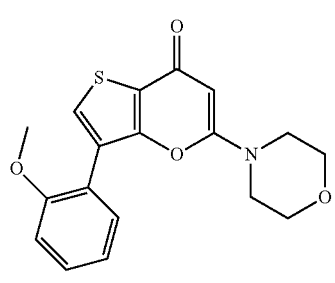 [SMILES: COc1ccccc1-c1csc2c(=O)cc(N3CCOCC3)oc12] | ND | ND | 343 | 344 (M + H) | A |

TABLE 8-continued

Illustrative compounds of formula I.

| Compound number | Structure | PC3 pAKT IC50 (µMolar) | IC50 PC3 Proliferation (µMolar) | Mass Expected | Mass Found | Synthetic Method |
|---|---|---|---|---|---|---|
| 114 | 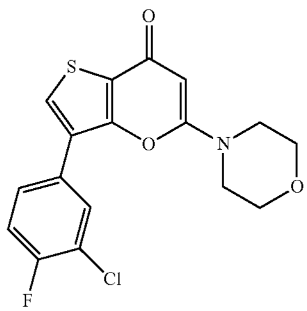 [SMILES: O=c1cc(N2CCOCC2)oc2c(-c3ccc(F)c(Cl)c3)csc12] | ND | ND | 365 | 366 (M + H) | A |
| 115 | 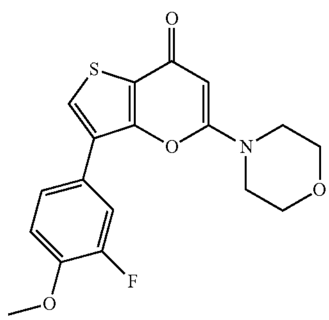 [SMILES: COc1ccc(-c2csc3c(=O)cc(N4CCOCC4)oc23)cc1F] | ND | ND | 361 | 362 (M + H) | A |
| 116 | 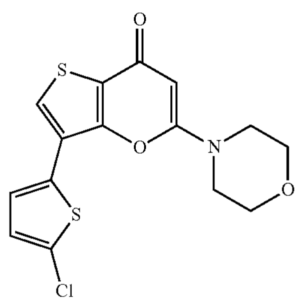 [SMILES: O=c1cc(N2CCOCC2)oc2c(-c3ccc(Cl)s3)csc12] | ND | ND | 353 | 354 (M + H) | B |
| 117 | 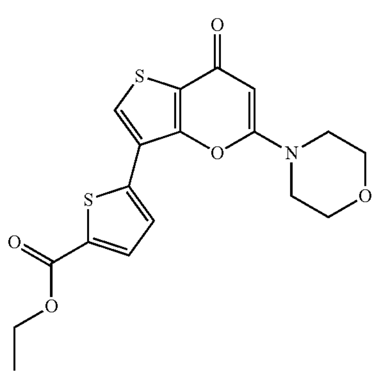 [SMILES: CCOC(=O)c1ccc(-c2csc3c(=O)cc(N4CCOCC4)oc23)s1] | ND | ND | 391 | 392 (M + H) | B |

ND—not determined

TABLE 9

NMR Data of representative compounds

| Cpd No. | NMR Analytical Data |
|---|---|
| 2 | $^1$H NMR (DMSO-d$_6$): 8.70 (dd, J = 4.4, 1.6 Hz, 2H), 8.47 (s, 1H), 7.74 (dd, J = 4.4, 1.6 Hz, 2H), 5.57 (s, 1H), 3.73 (t, J = 5.0 Hz, 4H), 3.45 (t, J = 4.9 Hz, 4H). |
| 3 | $^1$H NMR (DMSO-d$_6$): 8.94 (dd, J = 2.3, 0.9 Hz, 1H), 8.61 (dd, J = 4.9, 1.6 Hz, 1H), 8.33 (s, 1H), 8.14 (ddd, J = 7.8, 2.3, 1.6 Hz, 1H), 7.55 (ddd, J = 7.8, 4.9, 0.9 Hz, 1H), 5.56 (s, 1H), 3.71 (t, J = 4.9 Hz, 4H), 3.42 (t, J = 5.0 Hz, 4H). |
| 4 | $^1$H NMR (DMSO-d$_6$): 8.13 (s, 1H), 7.83 (dd, J = 1.9, 0.7 Hz, 1H), 6.84 (dd, J = 3.4, 0.6 Hz, 1H), 6.66 (dd, J = 3.4, 1.7 Hz, 1H), 5.55 (s, 1H), 3.75 (t, J = 5.0 Hz, 4H), 3.50 (t, J = 4.9 Hz, 4H). |
| 6 | $^1$H NMR (DMSO-d$_6$): 8.18 (s, 1H), 7.72 (dd, J = 8.5, 1.3 Hz, 2H), 7.51 (dd, J = 8.1, 7.0 Hz, 2H), 7.42 (d, J = 7.4 Hz, 1H), 5.54 (s, 1H), 3.71 (t, J = 5.0 Hz, 4H), 3.43 (t, J = 4.9 Hz, 4H). h |
| 7 | $^1$H NMR (DMSO-d$_6$): 8.08 (s, 1H), 7.28 (d, J = 1.6 Hz, 1H), 7.22 (dd, J = 8.0, 1.7 Hz, 1H), 7.04 (d, J = 8.1 Hz, 1H), 6.08 (s, 2H), 5.53 (s, 1H), 3.71 (t, J = 5.0 Hz, 4H), 3.42 (t, J = 5.0 Hz, 4H). |
| 8 | $^1$H NMR (DMSO-d$_6$): 8.06 (s, 1H), 7.65 (d, J = 8.8 Hz, 2H), 7.06 (d, J = 9.0 Hz, 2H), 5.53 (s, 1H), 3.80 (s, 3H), 3.72 (t, J = 4.9 Hz, 4H), 3.43 (t, J = 5.0 Hz, 4H). |
| 9 | $^1$H NMR (DMSO-d$_6$): 7.94 (s, 1H), 7.57-7.53 (m, 2H), 6.81 (d, J = 9.0 Hz, 2H), 5.52 (s, 1H), 3.72 (t, J = 5.0 Hz, 4H), 3.44 (t, J = 4.9 Hz, 4H), 2.50 (s, 6H). |
| 11 | $^1$H NMR (DMSO-d$_6$): 8.01 (s, 1H), 7.12 (t, J = 7.9 Hz, 1H), 6.87 (t, J = 1.9 Hz, 1H), 6.81 (dd, J = 8.5, 0.8 Hz, 1H), 6.59 (ddd, J = 8.0, 2.2, 1.0 Hz, 1H), 5.52 (s, 1H), 5.25 (s, 2H), 3.72 (t, J = 4.9 Hz, 4H), 3.43 (t, J = 5.0 Hz, 4H). |
| 13 | $^1$H NMR (DMSO-d$_6$): 8.40 (s, 1H), 8.08-7.92 (m, 4H), 5.57 (s, 1H), 3.73-3.71 (m, 4H), 3.46-3.43 (m, 4H), 3.28 (s, 3H). |
| 14 | $^1$H NMR (DMSO-d$_6$): 8.23 (s, 1H), 7.62 (ddd, J = 8.8, 4.4, 2.3 Hz, 4H), 7.21 (dd, J = 5.1, 3.7 Hz, 1H), 5.55 (s, 1H), 3.75 (t, J = 5.0 Hz, 4H), 3.52 (t, J = 5.0 Hz, 4H). |
| 15 | $^1$H NMR (DMSO-d$_6$): 8.12 (s, 1H), 7.61 (d, J = 8.1 Hz, 2H), 7.32 (dd, J = 8.5, 0.6 Hz, 2H), 5.53 (s, 1H), 3.71 (t, J = 5.0 Hz, 4H), 3.42 (t, J = 5.0 Hz, 4H), 2.35 (s, 3H). |
| 16 | $^1$H NMR (DMSO-d$_6$): 8.16 (s, 1H), 7.55-7.49 (m, 2H), 7.39 (t, J = 7.5 Hz, 1H), 7.23 (d, J = 8.1 Hz, 1H), 5.54 (s, 1H), 3.72 (t, J = 5.0 Hz, 4H), 3.44 (t, J = 4.9 Hz, 4H), 2.37 (s, 3H). |
| 19 | $^1$H NMR (DMSO-d$_6$): 11.33 (s, 1H), 8.11 (s, 1H), 7.75 (t, J = 0.7 Hz, 1H), 7.65 (d, J = 8.1 Hz, 1H), 7.44 (t, J = 2.8 Hz, 1H), 7.35 (dd, J = 8.2, 1.5 Hz, 1H), 6.48-6.46 (m, 1H), 5.55 (s, 1H), 3.73 (t, J = 4.9 Hz, 4H), 3.46 (t, J = 4.9 Hz, 4H). |
| 26 | $^1$H NMR (DMSO-d$_6$): 8.21 (s, 1H), 7.89 (dd, J = 2.9, 1.3 Hz, 1H), 7.71 (dd, J = 5.0, 2.9 Hz, 1H), 7.57 (dd, J = 5.0, 1.3 Hz, 1H), 5.54 (s, 1H), 3.74 (t, J = 5.0 Hz, 4H), 3.47 (t, J = 5.0 Hz, 4H). |
| 27 | $^1$H NMR (DMSO-d$_6$): 8.12 (s, 2H), 7.83 (t, J = 1.7 Hz, 1H), 7.00 (dd, J = 1.9, 0.9 Hz, 1H), 5.53 (s, 1H), 3.74 (t, J = 5.0 Hz, 4H), 3.46 (t, J = 5.0 Hz, 4H). |
| 28 | $^1$H NMR (DMSO-d$_6$): 8.07 (s, 1H), 7.22-7.19 (m, 2H), 6.98 (dd, J = 8.0, 0.8 Hz, 1H), 5.53 (s, 1H), 4.28 (s, 4H), 3.71 (t, J = 5.0 Hz, 4H), 3.43 (t, J = 4.9 Hz, 4H). |
| 29 | $^1$H NMR (DMSO-d$_6$): 8.20 (s, 1H), 7.42 (t, J = 8.2 Hz, 1H), 7.30-7.28 (m, 2H), 6.98 (ddd, J = 4.6, 2.3, 2.3 Hz, 1H), 5.54 (s, 1H), 3.80 (s, 3H), 3.71 (t, J = 5.0 Hz, 4H), 3.44 (t, J = 4.9 Hz, 4H). |
| 31 | $^1$H NMR (DMSO-d$_6$): 8.31 (s, 1H), 7.59-7.57 (m, 2H), 7.48-7.44 (m, 3H), 5.53 (s, 1H), 3.74 (t, J = 4.9 Hz, 4H), 3.49 (t, J = 4.9 Hz, 4H). |
| 32 | $^1$H NMR (DMSO-d$_6$): 8.79 (dd, J = 2.6, 0.7 Hz, 1H), 8.36 (s, 1H), 8.21 (dd, J = 8.3, 2.5 Hz, 1H), 7.69 (dd, J = 8.5, 0.6 Hz, 1H), 5.56 (s, 1H), 3.72 (t, J = 4.9 Hz, 4H), 3.42 (t, J = 4.9 Hz, 4H). |
| 35 | $^1$H NMR (DMSO-d$_6$): 11.34 (s, 1H), 8.10 (s, 1H), 7.76 (s, 1H), 7.64 (d, J = 8.1 Hz, 1H), 7.44 (t, J = 2.7 Hz, 1H), 7.34 (dd, J = 8.2, 1.5 Hz, 1H), 6.47 (s, 1H), 5.54 (s, 1H), 3.73 (t, J = 4.9 Hz, 4H), 3.46 (t, J = 5.0 Hz, 4H). |
| 36 | $^1$H NMR (DMSO-d$_6$): 8.16 (s, 1H), 7.68 (d, J = 8.8 Hz, 2H), 7.42 (d, J = 8.6 Hz, 2H), 5.54 (s, 1H), 3.71 (t, J = 4.9 Hz, 4H), 3.43 (t, J = 4.9 Hz, 4H), 3.23 (s, 3H), 1.41 (s, 9H). |
| 37 | $^1$H NMR (DMSO-d$_6$): 8.15 (s, 1H), 7.36 (d, J = 8.8 Hz, 2H), 6.72 (d, J = 9.0 Hz, 2H), 5.52 (s, 1H), 3.74 (t, J = 4.9 Hz, 4H), 3.49 (t, J = 4.9 Hz, 4H), 2.96 (s, 6H). |
| 38 | $^1$H NMR (DMSO-d$_6$): 8.24 (s, 1H), 7.51 (d, J = 8.8 Hz, 2H), 7.01 (d, J = 8.8 Hz, 2H), 5.52 (s, 1H), 3.80 (s, 3H), 3.74 (t, J = 4.9 Hz, 4H), 3.48 (t, J = 4.9 Hz, 4H). |
| 39 | $^1$H NMR (DMSO-d$_6$): 8.34 (s, 1H), 7.54-7.30 (m, 4H), 5.54 (s, 1H), 3.74 (t, J = 4.9 Hz, 4H), 3.49 (t, J = 4.9 Hz, 4H). |
| 40 | $^1$H NMR (DMSO-d$_6$): 8.30 (s, 1H), 6.71 (d, J = 2.3 Hz, 2H), 6.60 (t, J = 2.3 Hz, 1H), 5.53 (s, 1H), 3.77 (s, 6H), 3.73 (t, J = 4.9 Hz, 4H), 3.49 (t, J = 4.9 Hz, 4H). |
| 41 | $^1$H NMR (CDCl$_3$): 7.48-7.38 (m, 4H), 6.72-6.62 (m, 2H), 5.50 (s, 1H), 3.79 (s, 4H), 3.38 (s, 4H), 2.85 (s, 3H). |
| 42 | $^1$H NMR (CDCl$_3$): 8.12 (s, 2H), 8.02 (s, 1H), 7.84-7.70 (m, 2H), 7.58-7.48 (m, 1H), 5.58 (s, 1H), 4.15-3.88 (m, 10H), 3.48 (s, 4H), 3.06-2.90 (m, 6H). |
| 43 | $^1$H NMR (CDCl$_3$): 8.59 (s, 2H), 8.32 (s, 1H), 7.57 (s, 1H), 5.54 (s, 1H), 4.03 (s, 4H), 3.82 (s, 4H), 3.41 (s, 4H), 2.78 (s, 4H), 2.54 (s, 3H). |
| 44 | $^1$H NMR (CDCl$_3$): 8.18-8.10 (m, 2H), 7.75-7.71 (m, 3H), 5.50 (s, 1H), 3.96 (s, 3H), 3.80 (s, 4H), 3.42 (s, 4H). |
| 45 | $^1$H NMR (CDCl$_3$): 8.42 (s, 1H), 8.08-8.04 (m, 1H), 7.82-7.78 (m, 1H), 7.72 (s, 1H), 7.62-7.55 (m, 1H), 5.50 (s, 1H), 3.94 (s, 3H), 3.84 (s, 4H), 3.50 (s, 4H). |
| 47 | $^1$H NMR (CDCl$_3$): 7.70 (s, 1H), 5.48 (s, 1H), 3.95-3.30 (m, 16H). |
| 51 | $^1$H NMR (CDCl$_3$): 8.24 (s, 1H), 8.18 (s, 1H), 7.64-7.20 (m, 5H), 5.46 (s, 1H), 3.82 (s, 4H), 3.46 (s, 4H). |
| 52 | $^1$H NMR (CDCl$_3$): 7.62 (s, 1H), 5.48 (s, 1H), 3.94 -3.22 (m, 18H). |
| 53 | $^1$H NMR (DMSO-d$_6$): 8.16 (s, 1H), 7.42-7.23 (m, 5H), 6.48 (s, 1H), 5.40 (s, 1H), 4.60 (s, 2H), 3.58 (s, 4H), 3.14 (s, 4H). |
| 55 | $^1$H NMR (CD$_3$OD): 9.11 (s, 1H), 8.78 (s, 1H), 8.40 (s, 1H), 7.99 (s, 1H), 7.89-7.70 (m, 6H), 5.60 (s, 1H), 3.56 (s, 4H), 3.31 (s, 4H). |
| 56 | $^1$H NMR (DMSO-d$_6$): 7.861 (s, 1H), 7.37 (d, J = 8.6 Hz, 2H), 6.64 (d, J = 86 Hz, 2H), 5.50 (s, 1H), 5.35 (s, 2H), 3.72 (t, J = 4.9 Hz, 4H), 3.42 (t, J = 4.9 Hz, 4H). |
| 57 | $^1$H NMR (DMSO-d$_6$): 9.79 (s, 1H), 8.29 (s, 1H), 7.24 (t, J = 8.0 Hz, 1H), 6.99 (dt, J = 2.3, 1.2 Hz, 1H), 6.91 (t, J = 1.9 Hz, 1H), 6.86 (ddd, J = 5.5, 2.7, 1.5 Hz, 1H), 5.53 (s, 1H), 3.74 (t, J = 4.9 Hz, 4H), 3.49 (t, J = 4.9 Hz, 4H). |
| 58 | $^1$H NMR (DMSO-d$_6$): 10.57 (s, 1H), 8.97 (s, 1H), 8.35 (s, 2H), 8.25-8.13 (m, 3H), 7.93 (d, J = 9 Hz, 2H), 7.48-7.39 (m, 1H), 5.57 (s, 1H), 3.74 (s, 4H), 3.47 (s, 4H). |
| 59 | $^1$H NMR (DMSO-d$_6$): 10.70 (s, 1H), 8.50 (d, J = 6.0 Hz, 2H), 8.35 (s, 1H), 8.14 (d, J = 9.0 Hz, 2H), 7.93 (d, J = 9 Hz, 2H), 7.82 (d, J = 6.0 Hz, 2H), 5.57 (s, 1H), 3.74 (s, 4H), 3.46 (s, 4H). |

TABLE 9-continued

NMR Data of representative compounds

| Cpd No. | NMR Analytical Data |
|---|---|
| 60 | $^1$H NMR (DMSO-$d_6$): 10.12 (s, 1H), 8.32 (s, 1H), 8.11 (d, J = 8.9 Hz, 2H), 7.87 (d, J = 6.0 Hz, 2H), 7.61 (d, J = 9.0 Hz, 2H), 6.74 (d, J = 6.0 Hz, 2H), 5.56 (s, 1H), 3.74 (s, 4H), 3.45 (s, 4H), 2.88 (s, 6H). |
| 61 | $^1$H NMR (DMSO-$d_6$): 10.87 (s, 1H), 8.41 (d, J = 6.0 Hz, 1H), 8.35 (s, 1H), 8.20-8.16 (m, 2H), 7.88 (d, J = 8.2 Hz, 4H), 7.19 (dd, J = 6.6, 4.8 Hz, 1H), 5.57 (s, 1H), 3.74 (s, 4H), 3.46 (s, 4H). |
| 63 | $^1$H NMR (DMSO-$d_6$): 9.15 (t, J = 5.9 Hz, 1H), 8.35 (s, 1H), 8.29 (s, 1H), 8.04-7.85 (m, 2H), 7.62 (t, J = 9.0 Hz, 2H), 7.33 (s, 3H), 7.30-7.17 (m, 1H), 5.55 (s, 1H), 4.51 (d, J = 6.0 Hz, 2H), 3.66 (s, 4H), 3.44 (s, 4H). |
| 64 | $^1$H NMR (DMSO-$d_6$): 10.70 (s, 1H), 8.51 (d, J = 5.6 Hz, 2H), 8.42 (s, 1H), 8.37 (s, 1H), 8.02 (t, J = 6.2 Hz, 2H), 7.81 (d, J = 5.9 Hz, 2H), 7.70 (t, J = 6.0 Hz, 1H), 5.56 (s, 1H), 3.69 (s, 4H), 3.48 (s, 4H). |
| 65 | $^1$H NMR (DMSO-$d_6$): 10.08 (s, 1H), 8.40 (s, 1H), 8.34 (s, 1H), 7.96 (dd, J = 16.5, 7.5 Hz, 2H), 7.65 (t, J = 7.9 Hz, 1H), 7.58 (d, J = 8.5 Hz, 2H), 6.75 (d, J = 8.8 Hz, 2H), 5.56 (s, 1H), 3.68 (s, 4H), 3.48 (s, 4H), 2.88 (s, 6H). |
| 66 | $^1$H NMR (DMSO-$d_6$): 10.92 (s, 1H), 8.51 (s, 1H), 8.47-8.38 (m, 2H), 8.23 (d, J = 9.0 Hz, 1H), 8.07 (d, J = 7.6 Hz, 1H), 7.99 (d, J = 7.3 Hz, 1H), 7.94-7.81 (m, 1H), 7.66 (t, J = 7.8 Hz, 1H), 7.19 (t, J = 6.0 Hz, 1H), 5.57 (s, 1H), 3.69 (s, 4H), 3.48 (s, 4H). |
| 67 | $^1$H NMR (CD$_3$OD): 8.12 (dd, J = 8.1, 1.6 Hz, 1H), 7.78 (dd, J = 7.5, 1.6 Hz, 1H), 7.64-7.40 (m, 6H), 6.29 (s, 1H), 3.97 (dd, J = 11.4, 2.6 Hz, 2H), 3.48 (dt, J = 11.6, 2.3 Hz, 2H), 2.89 (tt, J = 11.5, 4.0 Hz, 1H), 1.89-1.63 (m, 4H). |
| 68 | $^1$H NMR (DMSO-$d_6$): 8.50 (dd, J = 8.0, 1.7 Hz, 1H), 7.69-7.45 (m, 7H), 6.90 (s, 1H), 3.67 (t, J = 4.9 Hz, 4H), 3.50 (t, J = 4.9 Hz, 4H). |
| 81 | $^1$H NMR (CDCl$_3$): 7.82 (s, 1H), 7.45 (s, 1H), 7.04 (s, 1H), 6.58 (s, 2H), 4.43 (s, 2H), 4.32 (s, 6H), 4.08 (s, 2H), 3.92 (s, 4H), 2.73 (t, J = 6.8 Hz, 2H), 2.58 (t, J = 6.8 Hz, 2H), 1.41 (s, 9H). |
| 85 | $^1$H NMR (DMSO-$d_6$): 8.29 (s, 1H), 7.81 (s, 1H), 7.70 (d, J = 7.3 Hz, 1H), 7.57-7.47 (m, 2H), 5.54 (s, 1H), 3.73 (s, 4H), 3.44 (s, 4H). |
| 86 | $^1$H NMR (DMSO-$d_6$): 8.65 (t, J = 2.0 Hz, 1H), 8.48 (s, 1H), 8.26-8.21 (m, 2H), 7.82 (t, J = 8.1 Hz, 1H), 5.58 (s, 1H), 3.73 (t, J = 4.9 Hz, 4H), 3.49 (t, J = 4.9 Hz, 4H). |
| 88 | $^1$H NMR (CDCl$_3$): 8.29 (s, 1H), 7.35-7.30 (m, 4H), 6.46 (s, 1H), 5.43 (s, 1H), 4.60 (d, J = 5.3 Hz, 2H), 3.65 (t, J = 4.5 Hz, 4H), 3.17 (t, J = 4.5 Hz, 4H). |
| 90 | $^1$H NMR (CDCl$_3$): 8.25 (s, 1H), 7.76 (s, 1H), 5.55 (s, 1H), 3.72-3.54 (m, 8H), 2.95-2.73 (m, 12H). |
| 91 | $^1$H NMR (CDCl$_3$): 8.10 (s, 1H), 6.26 (s, 1H), 5.47 (s, 1H), 3.85 (d, J = 3.0 Hz, 3H), 3.47 (s, 4H), 3.03 (d, J = 4.8 Hz, 4H). |
| 92 | $^1$H NMR (CD$_3$OD): 8.16 (s, 1H), 8.09 (s, 1H), 7.96 (s, 1H), 7.72 (s, 2H), 5.59 (s, 1H), 3.80 (s, 4H), 3.54 (s, 4H). |
| 93 | $^1$H NMR (CD$_3$OD): 7.92 (s, 1H), 7.85 (s, 1H), 7.48 (s, 1H), 7.05 (s, 1H), 5.58 (s, 1H), 3.84 (s, 4H), 3.59 (s, 4H). |
| 94 | $^1$H NMR (CDCl$_3$): 7.46 (d, J = 11.6 Hz, 2H), 6.31 (d, J = 6.9 Hz, 2H), 5.49 (s, 1H), 3.76 (s, 4H), 3.31 (s, 4H), 1.30 (s, 9H). |
| 95 | $^1$H NMR (CDCl$_3$): 7.48 (s, 1H), 7.04-6.99 (m, 2H), 6.78 (d, J = 7.8 Hz, 1H), 5.51 (s, 1H), 3.95-3.78 (m, 7H), 3.44 (s, 4H). |
| 96 | $^1$H NMR (CDCl$_3$): 7.55 (s, 1H), 7.27 (s, 2H), 7.22-7.18 (m, 1H), 6.95-6.65 (m, 1H), 5.46 (s, 1H), 3.85 (s, 4H), 3.51 (s, 4H). |
| 97 | $^1$H NMR (CDCl$_3$): 8.96 (s, 1H), 7.55 (s, 1H), 6.93 (s, 1H), 6.53 (s, 1H), 6.33 (s, 1H), 5.48 (s, 1H), 3.85 (s, 4H), 3.49 (s, 4H). |
| 98 | $^1$H NMR (CDCl$_3$): 7.52-7.45 (m, 2H), 6.97-6.92 (m, 2H), 5.60 (s, 1H), 5.50 (s, 1H), 3.80 (s, 4H), 3.42 (s, 4H). |
| 99 | $^1$H NMR (CDCl$_3$): 7.60 (s, 1H), 7.40-7.25 (m, 3H), 7.15 (s, 1H), 5.49 (s, 1H), 3.80 (s, 4H), 3.50 (s, 1H), 3.43 (s, 4H). |
| 100 | $^1$H NMR (DMSO-$d_6$): 8.30 (s, 1H), 8.05 (d, J = 8.2 Hz, 2H), 7.81 (d, J = 7.9 Hz, 2H), 5.55 (s, 1H), 3.72 (s, 4H), 3.44 (s, 4H). |
| 101 | $^1$H NMR (DMSO-$d_6$): 8.24 (s, 1H), 7.82-7.65 (m, 4H), 5.55 (s, 1H), 3.72 (s, 4H), 3.43 (s, 4H). |
| 102 | $^1$H NMR (DMSO-$d_6$): 8.16 (d, J = 6.0 Hz, 2H), 7.69 (d, J = 8.2 Hz, 2H), 7.45 (d, J = 7.9 Hz, 2H), 5.53 (s, 1H), 3.73 (s, 4H), 3.61 (s, 4H), 3.57 (s, 2H), 3.42 (s, 4H), 2.40 (s, 4H). |
| 104 | $^1$H NMR (DMSO-$d_6$): 9.10 (s, 1H), 8.52-8.48 (m, 1H), 8.34-8.28 (m, 1H), 8.18-8.10 (m, 1H), 5.55 (s, 1H), 3.95 (s, 3H), 3.75 (s, 4H), 3.46 (s, 4H). |
| 105 | $^1$H NMR (DMSO-$d_6$): 8.53 (s, 1H), 8.18 (s, 1H), 8.06 (d, J = 6.6 Hz, 1H), 6.98 (d, J = 9.0 Hz, 1H), 5.55 (s, 1H), 3.91 (s, 3H), 3.72 (s, 4H), 3.42 (s, 4H). |
| 106 | $^1$H NMR (CDCl$_3$): 7.91 (d, J = 6.0 Hz, 1H), 7.69 (s, 1H), 7.27-7.18 (m, 2H), 5.50 (s, 1H), 3.96 (s, 3H), 3.93 (s, 3H), 3.82 (s, 4H), 3.43 (s, 4H). |
| 107 | $^1$H NMR (CDCl$_3$): 7.52 (s, 1H), 7.12-7.00 (m, 3H), 5.88 (s, 1H), 5.49 (s, 1H), 3.93 (s, 3H), 3.81 (s, 4H), 3.43 (s, 4H). |

What is claimed is:

1. A compound of Formula VIII or IX

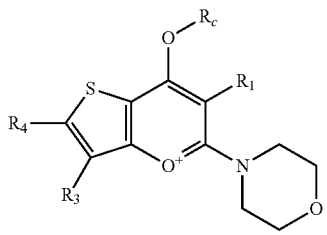

produced by a process compromising reacting a compound of Formula I

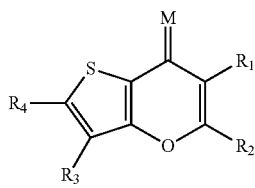

Formula I (a) with a halomethylester of the formula:
Hal-Rc
wherein Hal is a halogen and Rc is a hydrolysable linker of the formula Q

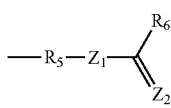

Q

R5 is $CH_2$, $CH(CH_3)$, $CH(Ph)$, $C(CH_3)(COOH)$, or $CH(CH(CH_3)_2)$;
Z1 and Z2 are independently S or O;
R6 is hydrogen optionally substituted aliphatic, optionally substituted aryl, alkoxy, carboxy, amino, heterocycle, aryloxy, and optionally substituted therewith a targeting agent (T) to from R6-T;
wherein M is O; R1 is selected from H, F, Cl, Br, I, alkenyl, alkynyl, carbocycle, aryl, heterocycle, heteroaryl, formyl, nitro, cyano, amino, carboxylic acid, carboxylic ester, carboxyl amide, reverse carboxyamide, substituted alkyl, substituted alkenyl, substituted alkynyl, substituted carbocycle, substituted aryl, substituted heterocycle, substituted heteroaryl, phosphonic acid, phosphinic acid, phosphoramidate, phosphonic ester, phosphinic ester, ketone, substituted ketone, hydroxamic acid, N-substituted hydroxamic acid, O-substituted hydroxamate, N- and O-substituted hydroxamate, sulfoxide, substituted sulfoxide, sulfone, substituted sulfone, sulfonic acid, sulfonic ester, sulfonamide, N-substituted sulfonamide, N,N-disubstituted sulfonamide, boronic acid, boronic ester, azo, substituted azo, azido, nitroso, imino, substituted imino, oxime, substituted oxime, alkoxy, substituted alkoxy, aryloxy, substituted aryloxy, thioether, substituted thioether, carbamate, substituted carbamate;
R2 is

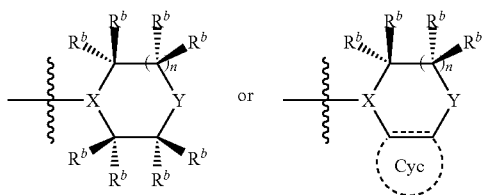

Where X is N;
n is 1;
Y is O;
$R^b$ is hydrogen (H) or independently at each instance any group defined in R1;
R3 is selected from R1;
R4 is selected from R1;

Cyc is selected from aryl, substituted aryl, heterocycle, substituted heterocycle, carbocycle, and substituted carbocycle and (b) when R6 is substituted with a targeting agent (T) to form R6-T, R6-T is selected from:

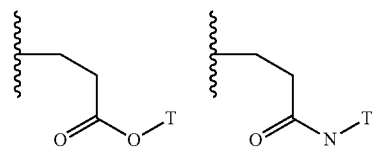

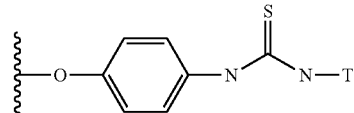

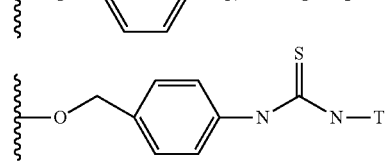

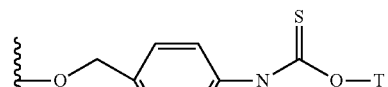

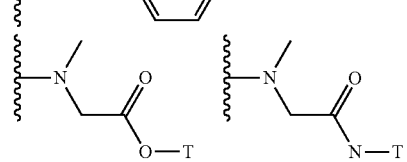

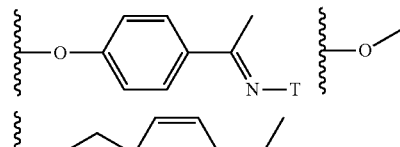

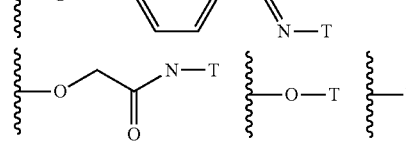

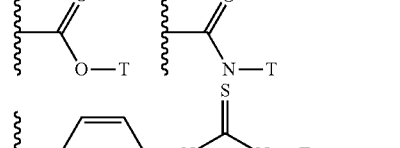

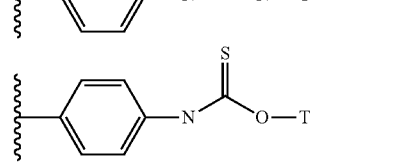

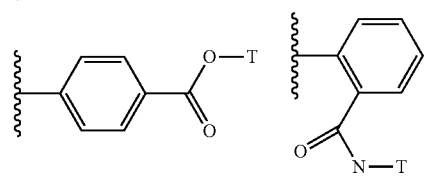

-continued
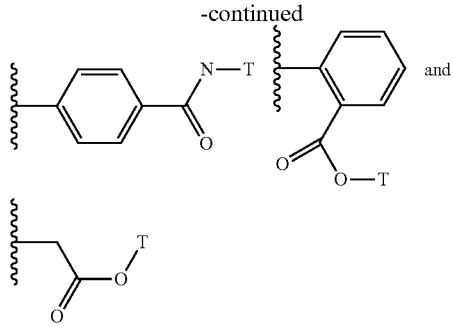
wherein T is selected from a carbohydrate, vitamin, peptide, protein, nucleoside, nucleotide, nucleic acid, liposome, lipid, bone-seeking agent, and cartilage seeking agent.
* * * * *